(12) United States Patent
Wang et al.

(10) Patent No.: US 7,537,803 B2
(45) Date of Patent: May 26, 2009

(54) POLYMER COATING/ENCAPSULATION OF NANOPARTICLES USING A SUPERCRITICAL ANTISOLVENT PROCESS

(75) Inventors: Yulu Wang, Harrison, NJ (US); Robert Pfeffer, Teaneck, NJ (US); Rajesh Dave, Short Hill, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 468 days.

(21) Appl. No.: 10/820,091

(22) Filed: Apr. 7, 2004

(65) Prior Publication Data
US 2005/0191491 A1    Sep. 1, 2005

Related U.S. Application Data

(60) Provisional application No. 60/461,506, filed on Apr. 8, 2003.

(51) Int. Cl.
| B05D 7/00 | (2006.01) |
| C08J 7/16 | (2006.01) |
| B01J 19/10 | (2006.01) |
| B29B 9/08 | (2006.01) |

(52) U.S. Cl. .................... 427/212; 427/214; 427/215; 427/220; 427/532; 427/560; 264/4.1; 264/5; 264/7; 264/9; 264/11

(58) Field of Classification Search .......... 264/7, 264/9, 4.1, 5, 11; 427/212, 213.3, 214, 215, 427/220, 532, 560
See application file for complete search history.

(56) References Cited

U.S. PATENT DOCUMENTS 5,766,637 A    6/1998  Shine et al.
5,833,891 A * 11/1998 Subramaniam et al. ........ 264/7
6,596,206 B2 *  7/2003  Lee ............................... 264/9
6,620,351 B2 *  9/2003  Gupta et al. .................... 264/7
7,087,197 B2 *  8/2006  Palakodaty et al. .......... 264/12
2002/0160109 A1 10/2002 Yeo et al.
2003/0031784 A1 * 2/2003 Perrut ........................ 427/212
2003/0146529 A1 * 8/2003 Chen et al. ................... 264/4.1

OTHER PUBLICATIONS

Bertucco et al., "Drug Encapsulation Using a Compressed Gas Antisolvent Technique," The four Italian Conference on Supercritical Fluids and their Application, E. Reverchon Supercritical fluids and their Application, E. Reverchon IEd.), Sep. 7-10, Capri, 1997, 327-334.*
PCT International Search Report dated Jan. 20, 2005.

(Continued)

*Primary Examiner*—William Phillip Fletcher, III
*Assistant Examiner*—Cachet I Sellman
(74) *Attorney, Agent, or Firm*—McCarter & English, LLP

(57) ABSTRACT

A process, method and/or system for preparing polymer-coated nanoparticles and/or other ultrafine particles utilizing a supercritical fluid, e.g., supercritical carbon dioxide (SC $CO_2$), as an antisolvent that may be added to a solution of a polymer and an organic solvent in which insoluble nanoparticles or the like are suspended. The coating process occurs when the supercritical fluid (e.g., SC $CO_2$) and the nanoparticle-containing suspension are combined to cause the suspended nanoparticles to precipitate as coated nanoparticles. Processing parameters for optimizing and/or enhancing the efficacy and/or efficiency of the coating process, method and/or system and for controlling the coating and/or agglomeration of coated particles are also described. The process, method and/or system has wide ranging applicability, e.g., for coating and/or encapsulation of pharmaceuticals, cosmetics, food products, chemicals, agrochemicals, pesticides, polymers, coatings, catalysts and the like.

24 Claims, 41 Drawing Sheets

OTHER PUBLICATIONS

Dorski, et al., Preparation and Characterization of Glucose-sensitive P(MMA-g-EG) Hydrogels, Polym. Mater. Sci. Eng. Proceed., 76, 1997, 281-282.

Luo, et al., In-Situ Optical Studies On Drop/Particle Formation in Supercritical Fluids, NATO Science Series, E 366, Kluwer Academic Publishers, 2000, pp. 1-8.

J.W. Tom and P.G. Denbedetti, Precipitation of Poly (L-lactic acid) and Composite Poly (L-lactic acid)-Pyrene Particles by Rapid Expansion of Supercritical Solutions, Journal of Supercritical Fluids 7 (1994), pp. 9-29.

K. Mishima, et al., Microencapsulation of Proteins by Rapid Expansion of Supercritical Solution with a Non solvent, *AIChE* Journal, vol. 46 (No. 4); (Apr. 2000), pp. 857-865.

C.J. Chang and A.D. Randolph, Precipitation of Microsize Organic Particles from Supercritical Fluids, *AIChE* Journal, vol. 35 (No. 11) (Nov. 1989); pp. 1876-1882.

D.W. Matson, et al., Rapid Expansion of Supercritical Fluid Solutions: Solute Formation of Powders, Thin Films, and Fibers, Ind. Eng.Chem. Res., vol. 26 (No. 11), (1987), pp. 2298-2306.

J.W. Tom and et al., Formation of Bioerodible Polymeric Microspheres and Micropracticles by Rapid Expansion of Supercritical Solutions, Biotechnol. Prog., vol. 7, (No. 5), (1991), pp. 403-411.

T.J. Young, et al., Encapsulation of Lysozyme in a Biodegradable Polymer by Preciptiation with a Vapor-over-Liquid Antisolvent, Journal of Pharmaceutical Sciences, Vo. 88, (Jun. 1999), pp. 640-645.

W. Stöber, et al., Controlled Growth of Monodisperse Silica Spheres in the Micron Size Range, Journal of Colloid and Interface Science, vol. 26, (1968), pp. 62-69.

D. Y. Peng, et al., A New Two-Constant Equation of State, Ind. Eng. Chem. Fundam., vol. 15 No. 1, (1976) pp. 59-64.

T. Katayama, et al., Isothermal Vapor-Liquid Equilibria of Acetone-Carbon Dioxide and Methanol-Carbon Dioxide Systems at High Pressures, Journal of Chemical Engineering Of Japan, vol. 8, (No. 2), (1975), pp. 89-92.

S.M. Walas, Phase Equilibria in Chemical Engineering, Butterworth Publishers, Boston, ch. 2, (1985) pp. 109-137.

C.J. Chang, et al., Solvent Expansion and Solute Solubility Predictions in Gas-Expanded Liquids, AIChE Journal, vol. 36 (No. 6), (Jun. 1990), pp. 939-942.

J. Xu, et al., Thickening Carbon Dioxide With the Fluoroacrylate-Styrene Copolymer, SPE Journal, vol. 8 (No. 2), (Jun. 2003), pp. 85-91.

T.A. Hoefling, et al., Design and Synthesis of Highly $CO_2$-Soluble Surfactants and Chelating Agents, Fluid Phase Equilibria, 83 (1993), pp. 203-212.

H. Liu, et al, Development of a Carbon Dioxide-Based Microencapsulation Technique for Aqueous and Ethanol-Based Latexes, Langmuir, vol. 18 (No. 16), 2002, pp. 6066-6070.

Bertucco, A., et al., "Drugs Encapsulation Using a Compressed Gas Antisolvent Technique", *The Fourth Italian Conference on Supercritical Fluids and their Applications*, Ed. E. Reverchon, Sep. 7-10, Capri, Italy, 1997, pp. 327-334.

Bleich, J., et al., "Production of drug loaded microparticles by the use of supercritical gases with the Aerosol Solvent Extraction System (ASES) process", J. *Microencapsulation*, vol. 13, 1996, pp. 131-139.

Brannon-Peppas, "Recent advances on the use of biodegradable microparticles and nanoparticles in the controlled drug delivery", International Journal of Pharmaceutics, 116, 1995, pp. 1-9.

Dillow, et al. "Production of Polymeric Support Materials Using Supercritical Fluid Gas Anti-Solvent Process", *The 4th International Symposium on Supercritical Fluids*, May 11-14, 1997, Sendai, Japan , pp. 247-250.

Gallagher, et al., "Gas Anti-Solvent Recystallization of RDX: Formation of Ultra-fine Particles of a Difficult-to-Comminute Explosive", Journal of Supercritical Fluids, 1992, vol. 5, pp. 130-142.

Krukonis, "Supercritical Fluid Nucleation of Difficult-to-Comminute Solids", paper 140f, *AIChE* annual meeting, San Francisco, Nov. 1984, pp. 25-30.

Lim, et al., "Gas Anti-solvent Recrystallization of Molecular Explosives Under Subcritical to Supercritical Conditions" (abstract only), Proceedings of the 5th *Meeting on Supercritical Fluids*, Tome1; ISBN 2-905-267-28-3, Mar. 23-25, Nice, France, 1998, p. 271.

McHugh, et al., Supercritical Fluid Extraction: Principles and Practice (Table of Contents only), 2nd Edition, Stoneham, MA: Butterworths-Heinemann, 1994.

Winters, et al., "Protein Purification with Vapor-Phase Carbon Dioxide" Biotechnol, Bioeng., 62, 1999, pp. 247-258.

Yeo, et al., "Formation of Microparticulate Protein Powders Using a Supercritical Fluid Antisolvent", Biotechnology and Bioengineering, vol. 41, 1993, pp. 341-346.

Vollath, et al., Coated nanoparticles: A new way to improved nanocomposites, Journal of Nanoparticle Research 1, 1999, pp. 235-242.

Takeo, et al., Formation of carbon nanocapsules with SiC nanoparticles prepared by polymer pyrolsis, J. Mater, Chem., vol. 8, No. 6, 1998, pp. 1323-1325.

Sglavo, et al., Fabrication and characterization of polymer-derived $Si_2N_2O$-$ZrO_2$ nanocomposite ceramics, Jounal of Matererials Science, vol. 28, 1993, pp. 6437-6440.

Kiran, et al., Supercritical Fluids: Fundamentals and Applications (Table of Contents only), NATO Science Series, E 366, Kluwer Academic Publishers, 2000.

D. Wang, D.R. Robinson, G.S. Kwon, J. Samuel, Encapsulation of Plasmid DNA in Biodegradable Poly(D,L-Lactic-co-Glycolic Acid) Microspheres as a Novel Approach for Immunogene Delivery, J. Control. Rel., 57 (1999) 9.

K.S. Soppimath, A.R. Kulkarni, T.M. Aminabhavi, Encapsulation of Antihypertensive Drugs in Cellulose-Based Matrix Microspheres: Characterization and Release Kinetics of Microspheres and Tableted Microspheres, J. Microencapsulation 18 (3)(2001) 397-409.

J.H. Kim, T.E. Paxton, D.L. Tomasko, Microencapsulation of Naproxen Using Rapid Expansion of Supercritical Solutions, *Biotechnol. Prog. 12* (1996) 650-661.

Y. Wang, D. Wei, R. Dave, R. Pfeffer, M. Sauceau, J.-J. Letourneau, J. Fages, Extraction and precipitation particle coating using supercritical $CO_2$, Powder Technology 127 (2002) 32-44.

M.L. O'Neill, Q. Cao, M. Fang, K.P. Johnston, S.P. Wilkinson, C. Smith, J.L. Kerchner, S.H. Jereller, Solubility of Homopolymers and Copolymers in Carbon Dioxide, Ind. Eng. Chem. Res. 37 (1998) 3067-3079.

V. Pessey, D. Mateos, F. Weill, F. Cansell, J. Etourneau, B. Chevalier, $SmCo_5$/Cu Particles Elaboration Using A supercritical Fluid Process, J. of Alloys and Compounds 323 (2001)412-416.

V. Pessey, R. Garriga, F. Weill B. Chevalier, J. Etourneau, F. Cansell, Core-shell Materials Elaboration in Supercritical Mixture $CO_2$/Ethano, Industrial & Engineering Chemistry Research 39 (12)(2000) 4714-4719.

Y. Wang, R. Dave, R. Pfeffer, Nanoparticle Encapsulation with Heterogeneous Nucleation in A Supercritical Antisolvent Process, Journal of Supercritical Fluids, In Press (2003).

A. Kordikowski, A.P. Schenk, R.M. Van Nielen, C.J. Peters, Volume Expansions and Vapor-Liquid Equilibria of Binary Mixtures of a Variety of Polar Solvents and Certain Near-Critical Solvents, Journals of Supercrit. Fluids 8 (1995) 205-216.

T.W. Randoph, A.J. Randolph, M. Mebes, S. Young. Sub-Micrometer-Sized Biodegradable Particles of Poly (L-Lactic Acid) via the Gas Antisolvent Spray Precipitation Proces. Biotechnol. Progress 9 (1993) 429.

S. Mawson, K.P. Johnston, D.E. Betts, J.B. McClain, J.M. DeSimone, Stablized Polymer Microparticles by Precipitation with a Compress Fluid Antisolvent: 1. Poly (Fluoro Acrylates), Macromoecules 30 (1997) 71-77.

P.D. Condo, D.R. Paul and K.P. Johnston, Glass Transition of Polymers with Compressed Fluid Diluents: Type II and III Behavior, Macromolecules, 27 (1994) 365-371.

E. Reverchon, G. Della Porta, A. Di Trolio, S. Pace, Supercritical Antisolvent Preparation of Nanoparticles of Superconductor Precursors, Ind. Eng. Chem. Res. 37 (1998) 952-958.

P. Chattopadhyay and R.B. Gupta, Supercritical $CO_2$ based on Production of Fullerence Nanoparticles,Ind. Eng. Chem. Res. 39 (2000) 2281-2289.

L.S. Tu, F. Dehghani, N.R. Foster, Micronisation and Microencapsulation of Pharmaceuticals Using a Carbon Dioxide Antisolvent, Powder Technol.126 (2002) 134-149.

A. Blasig, C. Shi, R.M. Enick, M.C. Thies, Effect of Concentration and Degree of Saturation on RESS of a $CO_2$-soluble Fluoropolymer, *Ind. Eng. Chem. Res.*, 41 (20), (2002), 4976-4983.

K.A. Shaffer, T.A. Jones, D.A. Canelas, J.M. DeSimone, Dispersion Polymerizations in Carbon Dioxide Using Siloxane-Based Stablizers, Macromolecules, 29 (7), 1996, 2704-2706.

D.A. Canelas, D.E. Betts, J.M. DeSimone, Poly (vinyl acetate) and Poly (vinyl acetate-co-ethylene) Latexes via Dispersion Polymerizations in Carbon Dioxide, Macromolecules, 31 (20), 1998, 6794-6805.

M.Z. Yates, G. Li, J.J. Shim, S. Maniar, K.P. Johnston, K.T. Lim, S. Webber, Ambidextrous Surfactants for Water-Dispersible Polymer Powder from Dispersion Polymerization in Supercritical $CO_2$, *Macromoleculres*, 32 (4), 1999, 1018-1026.

H. Shiho and J.M. DeSimone, Dispersion Polmerization of Acrylonitrile in Supercritical Carbon Dioxide, *Macromolecules*, 33 (5), 2000, 1565-1569.

S. Mawson, M.Z. Yates, M.L. O'Neill, K.P. Johnston, Stablized Polymer Microparticles by Precipitation with a Compressed Fluid Antisolvent. 2. Poly (propylene oxide)- and Poly (butyelen oxide)-Based Copolymers, *Langmuir*, 13 (6), 1997, 1519-1528.

Charoenchaitrakool, M; Dehghani, F; Foster, N.R., "Micronization by rapid expansion of supercritical solution to enhance the dissolution rate of poorly water-soluable pharmaceuticals", *Ind. Eng. Chem. Res.* 39, 2000, 4794-4802.

Elvassore, N.; Bertucco, A.; Caliceti, P., "Production of protein-loaded polymeric microcapsules by compressed $CO_2$ in a mixed solvent", *Ind. Eng. Chem. Res.* 40, 2001, 795-800.

Falk, R.: Randolph, T.W.; Meyer, J.D.; Kelly, R.M.; Manning, M.C., "Controlled release of ionic compounds from poly (L-lactide) microspheres produced by precipitation with a compressed antisolvent", *J. Control. Rel.*, 44, 1997, 77-85.

Ghaderi, R.; Artursson, P.; Carlfors, J., "A new method for preparing biodegradable microparticles and entrapment of hydrocortisone in D,L-PLG microparticles using supercritical fluids", *European J. of Pharm. Sci.*, 10, 2000, 1-9.

Thies, J. and Müller, B. W., "Size controlled production of biodegradable microparticles with supercritical gases", *European J. Pharm. Biopharm.*, 45, 1998, 67-74.

Tu, L. Sze,; Dehghani, F.; Foster, N.R., "Micronisation and encapsulation of pharmaceuticals using a carbon dioxide antisolvent", *Powder Technol.* 126, 2002, 134-149.

J.X. Zhang, L.Q. Gao, Nanocomposite powders from coating with heterogeneous nucleation processing, Ceram. Int. 27 (2001) 143.

S.Y. Chang, L. Liu, S.A. Asher, Preparation and properties of tailored morphology, monodisperse colloidal silica-cadmium sulfide nonocomposites, J. Am Chem. Soc. 116 (1994) 6739.

J.C. Leroux, E. Allémann, R.D. Jaeghere, E. Doelker, R. Gurny, Biodegradable nonoparticles—from sustained release formulations to improved site specific drug delivery, J. Control. Rel. 39 (1996) 339.

H. Cohen, R.J. Levy, J. Gao, V. Kousev, S. Sosnowski, S. Slomkowski, G. Golomb, Sustained delivery and expression of DNA encapsulated in polymeric nonoparticles, Gene Ther. 7 (2000) 1896.

Y. Zhang, Q Zhang, Y. Li, N. Wang, J. Zhu, Coating of carbon nontubes with tungsten by physical vapor deposition, Solid State Comm. 115 (2000) 51.

D. Shi, S.X. Wang, W.J. Ooij, L.M. Wang, J.G. Zhao, Z, Yu, Uniform deposition of ultra thin polymer films on the surface of $Al_2O_3$ nonparticles by a plasma treatment, Appl. Phys. Lett. 78 (2001) 1243.

J.S. Hrkach, M.T. Peracchia, A. Domb, N. Lotan, R. Langer, Nonotechology for biomaterials engineering: structural characterization of amphiphilic polymeric nonoparticles by $^1H$ NMR spectroscopy, Biomaterials 18 (1997) 27.

K.W. Leong, H.-Q. Mao, V.L. Truong-Le, K. Roy, S.M. Walsh, J.T. August, DNA-polycation nonospheres as non-viral gene delivery vehicle, J. Control. Rel. 53 (1998) 183.

Y.S. Jong, J.S. Jacob, K.-P. Yip, G Gardner, E. Seitelman, M. Whitney, S. Montgomery, E. Mathiowitz, Controlled release of plasmid DNA, J. Control. Rel. 47 (1997) 123.

K. Fu, K. Griebenow, L. Hseih, V.M. Klibanov, R. Langer, FTIR characterization of the secondary structure of proteins encapsulated within PLGA microspheres, J. Control. Rel. 58 (1999) 357.

A.J. Ruys, Y.W. Mai, The nonoparticle-coating process; a potential sol-gel route to homogenous nanocomposites, Mater, Sci. Eng. A 265 (1999) 202.

A. Tsutsumi, S. Nakamato, T. Mineo, K. Yoshida, A novel fluidized-bed coating of fine particles by rapid expansion of supercritical fluid solutions, Powder Technol. 85 (1995) 275.

T.J. Wang, A. Tsutsumi, H. Hasegawa, T. Mineo, Mechanism of particle coating granulation with RESS process in a fluidized bed, Power Tecnol. 118 (2001) 229.

E. Reverchon, G. Della Porta, I. De Rosa, P. Subra, D. Letourneur, Supercritical antisolvent microinzation of some biopolymers, J. Supercrit, Fluids 18 (2000) 239.

C.S. Lengsfeld, J.P. Delplangue, V.H. Barocas, T.W. Randolph, Mechansim governing microparticle morphology during precipitation by a compressed antisolvent: atomization vs. nucleation and growth, J. Phys. Chem. 104 (2000) 2725-2735.

S. Bristow, T. Shekunov, B. Yu. Shekunov, P. York, Analysis of the supersaturation and precipitation process with supercritical $CO_2$, J. Supercrit, Fluids 21 (2001) 257-271.

E. Reverchon, Supercritical antisolvent precipitation of micro- and non-particles, J. Supercrit, Fluids 15 (1999) 1.

\* cited by examiner

**EXPERIMENTAL CONDITIONS IN SAS COATING
AND CO-PRECIPITATION PROCESS**

| Parameters / Experiments | Solvent | Polymer Conc. (g/ml) | Ratio of polymer to particles (g/g) |
|---|---|---|---|
| Coating of drug particles | DCM | 1.0 | 1:4 |
| | | | 1:2 |
| | | | 1:1 |
| Co-precipitation of drug and PLGA | Acetone | 1.0 | 1:1 |
| | Methanol and DCM | 1.0 | 1:1 |

FIG. 17

ENCAPSULATION EFFICIENCY (EE) OF COATED DRUG PARTICLES AND CO-PRECIPITATED PARTICLES.

| Ratio of PLGA to HC | SAS Process | Encapsulation Efficiency (EE) (%) | Average (%) | SD |
|---|---|---|---|---|
| 1:4 | *Coating | 0 | 0 | 0 |
| 1:2 | Coating | 8.4 | 6.7 | ± 1.4 |
| | | 6.3 | | |
| | | 5.4 | | |
| 1:1 | Coating | 21.5 | 22.6 | ± 2.3 |
| | | 25.2 | | |
| | | 21.2 | | |
| 1:1 | *Co-precipitation from methanol and DCM | 0 | 0 | 0 |
| 1:1 | *Co-precipitation from acetone | 0 | 0 | 0 |

* Analysis was performed in three replicates on each sample.

FIG. 23

Poly lactide-co-glycolide (PLGA)

Poly fluoroacrylate-styrene (PFS)

Poly fluoroacrylate (PFA)

Perfluoropolyether (PFPE)

| Run No. | T (°C) | P (MPa) | PLGA Conc. (mg/ml) | PLGA Weight Fraction | Flow rate (ml/min) | Observation |
|---|---|---|---|---|---|---|
| 1 | 33.0 | 8.96 | 10.0 | 25.0 | 0.8 | Fairly Loose agglomerates |
| 2 | 33.0 | 8.96 | 10.0 | 16.7 | 0.8 | Very loose agglomerates |
| 3 | 33.0 | 8.96 | 10.0 | 12.5 | 0.8 | Very loose agglomerates |
| 4 | 33.0 | 11.03 | 10.0 | 25.0 | 0.8 | Heavily agglomerated (Sintering) |
| 5 | 38.0 | 8.96 | 10.0 | 16.7 | 0.8 | Very loose agglomerates |
| 6 | 42.5 | 8.96 | 10.0 | 16.7 | 0.8 | Fairly loose agglomerates (Some sintering) |
| 7 | 33.0 | 8.96 | 4.0 | 16.7 | 0.8 | No agglomerates observed |
| 8 | 33.0 | 8.96 | 13.0 | 16.7 | 0.8 | Loose agglomerates |
| 9 | 33.0 | 8.96 | 10.0 | 16.7 | 1.8 | Loose agglomerates |
| 10 | 33.0 | 8.96 | 10.0 | 16.7 | 2.8 | Loose agglomerates |

FIG. 27

| T (°C) | P (MPa) | Surfactant | Surfactant Conc. (wt.%) in SC $CO_2$ | Observation |
|---|---|---|---|---|
| 32.0 | 9.65 | PFS | 0.018 | Dense film coating on the surface of vessel and stirrer. |
| 32.0 | 9.65 | PFA | 0.018 | Dense film coating on the surface of vessel and stirrer. |
| 32.0 | 9.65 | PFPE | 0.018 | Dense film coating on the surface of vessel and stirrer. |

FIG. 28

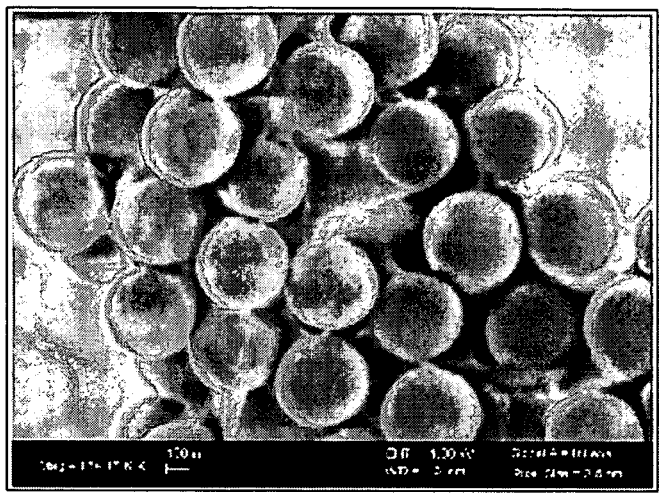
FIG. 34(a)
FIG. 34(b)
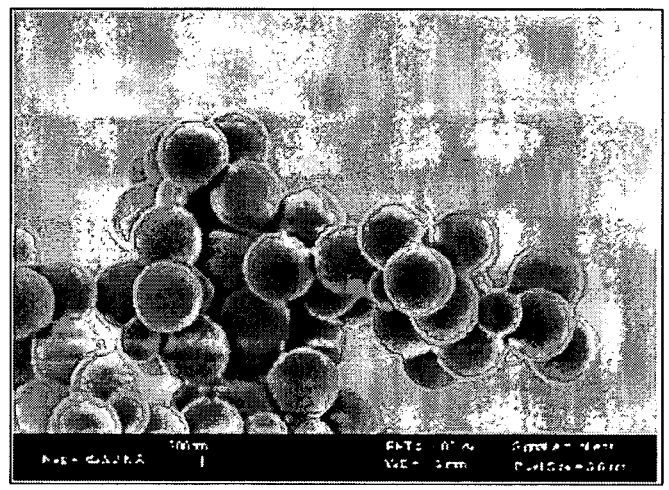
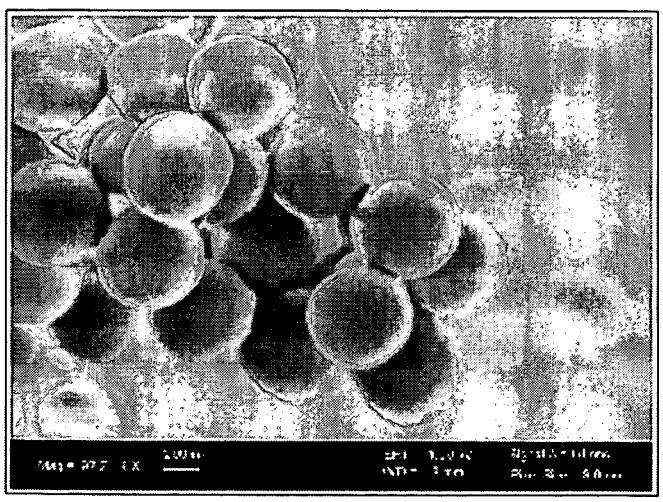
FIG. 34(c)

POLYMER COATING/ENCAPSULATION OF NANOPARTICLES USING A SUPERCRITICAL ANTISOLVENT PROCESS

CROSS-REFERENCE TO RELATED APPLICATION

The present application claims the benefit of a provisional patent application entitled "Nanoparticle Coating Using a Supercritical Antisolvent Process," filed on Apr. 8, 2003 and assigned Ser. No. 60/461,506. The contents of the foregoing provisional patent application are incorporated herein by reference.

The U.S. Government has a paid-up license in this invention and the right in limited circumstances to require the patent owner to license others on reasonable terms as provided for by the terms of Grant No. NSF-CTS-9985618 awarded by the National Science Foundation.

BACKGROUND

1. Technical Field

The present disclosure relates to a process, method and/or system for preparing polymer coated nanoparticles/ultrafine particles and the coated nanoparticles/ultrafine particles produced thereby. More particularly, the present disclosure relates to a process, method and/or system for preparing polymer-coated nanoparticles/ultrafine particles using a supercritical fluid, e.g., supercritical carbon dioxide, as an antisolvent in to which a solution or system that includes the polymer and an organic solvent is introduced. The nanoparticles/ultrafine particles are typically suspended in the organic solvent. Processing parameters for optimizing and/or enhancing the efficacy and/or efficiency of the disclosed coating process, method and/or system and for controlling the coating and/or agglomeration of coated particles are also described.

2. Background of Related Art

The rapid development of nanotechnology and nanomaterials has led to a need for nanoparticle surface modification for a variety of applications. The surface can be tailored to specific physical, optical, electronic, chemical and biomedical properties by coating a thin film of material on the surface of the nanoparticles. Conventional nanoparticle coating methods include dry and wet approaches. Dry methods include: (a) physical vapor deposition [Y. Zhang, Q. Zhang, Y. Li, N. Wang, J. Zhu, *Coating of carbon nanotubes with tungsten by physical vapor deposition*, Solid State Commun. 115 (2000) 51], (b) plasma treatment [D. Shi, S. X. Wang, W. J. Ooij, L. M. Wang, J. G. Zhao, Z. Yu, *Uniform deposition of ultrathin polymer films on the surfaces of $Al_2O_3$ nanoparticles by a plasma treatment*, Appl. Phys. Lett. 78 (2001) 1243; D. Vollath, D. V. Szabó, *Coated nanoparticles: a new way to improved nanocomposites*, J. Nanoparticle Res. 1 (1999) 235], (c) chemical vapor deposition [O. Takeo, N. Koichi, S. Katsuaki, *Formation of carbon nanocapsules with SiC nanoparticles prepared by polymer pyrolysis*, J. Mater. Chem. 8 (1998) 1323], and (d) pyrolysis of polymeric or non-polymeric organic materials for in situ precipitation of nanoparticles within a matrix [V. M. Sglavo, R. Dal Maschio, G. D. Soraru, A. Bellosi, *Fabrication and characterization of polymer-derived silicon nitride oxide Zirconia ($Si_2N_2O$—$ZrO_2$) nanocomposite ceramics*, J. Mater Sci. 28 (1993) 6437]. Wet methods for coating nanoparticles include: (a) sol-gel processes and (b) emulsification and solvent evaporation techniques [H. Cohen, R. J. Levy, J. Gao, V. Kausaev, S. Sosnowski, S. Slomkowski, G. Golomb, *Sustained delivery and expression of DNA encapsulated in polymeric nanoparticles*, Gene Ther. 7 (2000) 1896; J. S. Hrkach, M. T. Peracchia, A. Domb, N. Lotan, R. Langer, *Nanotechnology for biomaterials engineering: structural characterization of amphiphilic polymeric nanoparticles by $^1H$ NMR spectroscopy*, Biomaterials 18 (1997) 27; D. Wang, D. R. Robinson, G. S. Kwon, J. Samuel, *Encapsulation of plasmid DNA in biodegradable poly(D,L-lactic-co-glycolic acid) microspheres as a novel approach for immunogene delivery*, J. Control. Rel. 57 (1999) 9].

The coating or encapsulation of nanoparticles has been found to be of particular interest for the controlled release of drugs, genes, and other bioactive agents. Controlled release systems provide the benefits of protection from rapid degradation, targeting delivery, control of the release rate, and prolonged duration of bioactive agents.

Leroux et al. studied the surface modification of nanoparticles of poly D,L-lactic acid (D,L-PLA) loaded with drugs to improve site-specific drug delivery. [See, J. C. Leroux, E. Allémann, F. D. Jaeghere, E. Doelker, R. Gurny, *Biodegradable nanoparticles—from sustained release formulations to improved site specific drug delivery*, J. Control. Rel. 39 (1996) 339]. The drug delivery system was prepared using the emulsion method. Results indicated that drug loaded nanoparticles of D,L-PLA, which were coated with polyethylene glycol (PEG), provided protection from uptake by human monocytes. The findings revealed that surface modified nanoparticles with PEG could temporarily avoid the mono-nuclear phagocyte system and substantially prolong the circulation time of the nanoparticles.

Bertucco et al. did a preliminary study of particle encapsulation by polymer using a GAS process. In their study, particles of KCl were suspended in a solution of polymers (hydroxypropyl methylcellulose phthalate, Eudragit® E 100, ethylcellulose) in various organic solvents (toluene, acetone, 1,4-dioxane, ethylacetate). Compressed $CO_2$ was introduced into a high-pressure vessel, in which the suspension was charged. The compressed $CO_2$ was dissolved in the organic solution, leading to the loss of solvent strength of the organic solvent. As a result, the polymer precipitated out and deposited on the surface of suspended KCl particles. [Bertucco et al., "Drugs encapsulation using a compressed gas antisolvent technique," *The Fourth Italian Conference on Supercritical Fluids and their Application*, E. Reverchon (Ed.), September 7-10, Capri, 1997, 327-334.]

Cohen et al. prepared a sustained gene delivery system of DNA encapsulated in polymeric nanoparticles using a double emulsion approach. [See, Cohen et al., *Sustained delivery and expression of DNA encapsulated in polymeric nanoparticles*, Gene Ther. 7 (2000) 1896]. In their research, the gene delivery system was found to offer increased resistance to nuclease degradation since the polymeric coating provides protection from serum nuclease. The activity of plasmid DNA administration was found to be in the sustained duration mode. The gene delivery system is a potential formulation for the application of gene therapy.

The emulsion techniques used above are associated with the following four steps: (a) preparing the solution of polymer and bioactive agent in an organic solvent, (b) dispersing the solution in another phase under vigorous stirring, (c) stabilizing under certain temperature and pH conditions, and (d) evaporating the organic solvent. However, during the emulsion preparation, the organic solvent and the strong shearing force, temperature, pH, and the interface between the oil and water phases may affect and/or alter the structure of the bioactive agents. In addition, these processes require large amount of organic solvents, surfactants, and other additives, leading to volatile organic compound (VOC) emissions and other waste streams. Other drawbacks include low encapsulation efficiency and further processing of the products such as down-stream drying, milling and sieving, which are usually necessary. In addition, residual toxic solvent in the end products, temperature and pH requirements, and strong shear forces are big challenges for maintaining the fragile protein structure in the encapsulation of pharmaceutical ingredients.

There are a number of prior art publications dealing with particle coating or encapsulation using supercritical carbon dioxide ["SC $CO_2$"]. For example, Kim et al. reported the microencapsulation of naproxen using rapid expansion of supercritical solutions (RESS). [See, J. H. Kim, T. E. Paxton, D. L. Tamasko, *Microencapsulation of naprozen using rapid expansion of supercritical solutions*, Biotechnol. Prog. 12 (1996) 650]. The RESS process was also used to coat/encapsulate particles by Mishima et al. [See, K. Mishima, K. Matsuyama, D. Tanabe, S. Yamauchi, T. J. Young, K. P. Johnston, *Microencapsulation of proteins by rapid expansion of supercritical solution with a nonsolvent*, AIChE J. 46 (4) (2000) 857-865]. In the RESS coating process, the material to be coated and the coating material (polymer) are both dissolved in SC $CO_2$ with or without a cosolvent. The solution is then released from a nozzle (de-pressurized), generating microparticles with a polymer coating on the surface. In RESS, the rapid de-pressurization of the supercritical solution causes a substantial lowering of the solvent power of $CO_2$ leading to very high supersaturation of solute, precipitation, nucleation and particle growth. However, the application of the RESS process is severely limited by the fact that polymers, in general, have very limited solubility in SC $CO_2$ at temperatures below 80° C. Also, the operating pressure in RESS is usually above 200 bars so that the process is less attractive economically.

Tsutsumi et al. used a combination of the RESS process and a fluidized bed for coating particles. [See, A. Tsutsumi, S. Nakamoto, T. Mineo, K. Yoshida, *A novel fluidized-bed coating of fine particles by rapid expansion of supercritical fluid solutions*, Powder Technol. 85 (1995) 275]. In their research, a solution of coating material in SC $CO_2$ (rather than in an organic solvent) is sprayed into the fluidized bed of particles to be coated. However, particles less than 30-50 µm fall into Geldart's Group C particle classification and are very difficult to fluidize. Hence, this method cannot be used to coat ultrafine particles.

Pessey et al. also demonstrated particle coating using a supercritical fluid process. [See, V. Pessey, D. Mateos, F. Weill, F. Cansell, J. Etoumeau, B. Chevalier, *SmCo$_5$/Cu particles elaboration using a supercritical fluid process*, J. Alloys Compounds 323 (2001) 412]. Their research involved the thermal decomposition of an organic precursor and the deposition of copper onto the surface of core particles in SC $CO_2$ under conditions of temperature up to 200° C. and pressure up to 190 MPa. However, their methods are less attractive from the point of view of safety and cost and probably cannot be applied to the pharmaceutical industry since high temperature could adversely effect or even destroy most drug powders.

Tom and Debenedetti investigated a SC $CO_2$ process for the formation of drug loaded microspheres for controlled drug release. In this work, a model system of biopolymer PLA and pyrene was chosen for the composite powder formation study. PLA and pyrene were dissolved in SC $CO_2$ with acetone as a cosolvent in two different units. The two resulting supercritical solutions were mixed and were pumped to an expansion device (orifices or capillaries, 25-50 µm). When the solution flowed through the expansion device, it underwent a rapid decompression, resulting in co-precipitation of the solutes. It was found that the pyrene was uniformly incorporated into the produced polymer microspheres. [See, Tom et al., *Precipitation of poly (L-lactic acid) and composite poly (L-lactic acid)-pyrene particles by rapid expansion of supercritical solutions*, J. Supercrit. Fluids, 7, 1994, 9-29.]

Recently, Wang et al. used a modified RESS process of extraction and precipitation to coat particles with polymer. [See, Wang et al., *Extraction and precipitation particle coating using supercritical $CO_2$*, Powder Technology 127 (2002) 32-44.] The coating polymer and particles to be coated (host particles) were placed in two different high-pressure vessels, respectively. The coating polymer was first extracted by SC $CO_2$. The resulting supercritical polymer solution was then introduced into the host particle vessel. By adjusting the temperature and pressure, the polymer solubility in SC $CO_2$ was lowered and nucleation and precipitation of polymer took place on the surface of the host particles and a fairly uniform polymer coating was formed. However, potential application of RESS for particle coating or encapsulation is limited because the solubility of polymers in SC CO2 is generally very poor. [See, O'Neill et al., *Solubility of Homopolymers and Copolymers in Carbon Dioxide*, Ind. Eng. Chem. Res. 37 (1998) 3067-3079.] As an alternative, antisolvent processes (GAS/SAS/ASES/SEDS) for drug delivery system design have attracted attention because of their flexibility in choosing a suitable solvent which is miscible with SC $CO_2$.

The use of SC $CO_2$ as an antisolvent (SAS process), however, can usually be performed at a pressure lower than 10 MPa and at a temperature just above the critical temperature (304.1° K). Also the SAS process is quite flexible in terms of solvent choice. Thus, the synthesis of ultrafine particles using SAS has been reported in a number of studies [E. Reverchon, G. Della Porta, I. De Rosa, P. Subra, D. Letourneur, *Supercritical antisolvent micronization of some biopolymers*, J. Supercrit. Fluids 18 (2000) 239; D. J. Dixon, K. P. Johnston, R. A. Bodmeier, *Polymeric materials formed by precipitation with a compressed fluid antisolvent*, AIChE J. 39 (1993) 127; R. Falk, T. W. Randolph, J. D. Meyer, R. M. Kelly, M. C. Manning, *Controlled release of ionic compounds from poly (L-lactide) microspheres produced by precipitation with a compressed antisolvent*, J. Control. Release 44 (1997) 77; T. J. Young, K. P. Johnston, K. Mishima, H. Tanaka, *Encapsulation of lysozyme in a biodegradable polymer by precipitation with a vapor-over-liquid antisolvent*, J. Pharmaceut. Sci. 88 (1999) 640].

Falk et al. investigated the production of composite microspheres by the SAS process. [See, Falk et al., *Controlled release of ionic compounds from poly (L-lactide) microspheres produced by precipitation with a compressed antisolvent*, J. Control. Release 44 (1997) 77]. In their study, drugs of gentamycin, naloxone and naltrexone and PLA were dissolved in methylene chloride using the hydrophobic ion-pairing (HIP) complexation method, which improved the solubility of the drugs considerably, to make a homogeneous solution. The prepared solutions were sprayed into SC $CO_2$ through an ultrasonic nozzle vibrating at 120 kHz. The drug loaded microspheres (0.2-1.0 µm) formed due to the co-precipitation of the drugs and the PLA. Drug release tests showed that gentamycin was successfully incorporated into a PLA matrix, exhibiting diffusion controlled drug release. However, naltrexone and rifampin were found to be poorly incorporated because these two drugs were more lipophilic and somewhat soluble in SC $CO_2$, resulting in drug surface bonding on the microspheres. Recently, Young et al. investigated the encapsulation of lysozyme with a biodegradable polymer by precipitation with a vapor-over-liquid antisolvent, which is a modified precipitation with a compressed antisolvent process. [See, Young et al., *Encapsulation of lysozyme in a biodegradable polymer by precipitation with a vapor-over-liquid antisolvent*, J. Pharmaceut. Sci. 88 (1999) 640]. In their research, the vapor-over-liquid antisolvent coating process was used to encapsulate 1-10 μm lysozyme particles.

Drug loaded microspheres can be produced by alternative techniques, e.g., phase separation, spray-drying, freeze-drying, and interfacial polymerization techniques. All of these methods involve the dissolution of the polymer and the drug in an organic solvent, dispersion of the solution under a strong force, and stabilization under certain temperature and pH conditions. However, as was the case for emulsion techniques, problems of residual organic solvent in the final product and low encapsulation of drugs due to partitioning of the pharmaceutical components between two immiscible liquid phases are frequently encountered. Moreover, harsh conditions, such as temperatures, pH conditions and strong shear forces, may denature some bio-active agents. Also, extensive downstream processing is usually required when using these conventional methods.

Bleich and Müller have studied drug-loaded particle formation using an ASES process. PLA was used as the carrier and several different drugs, such as hyoscine butylbromide, indomethacin, piroxicam and thymopentin, were selected as model drugs. The drugs and PLA were dissolved in methylene chloride and the solution was atomized into SC $CO_2$ through a 400 μm nozzle at a flow rate of 6 ml/min. The solvation of SC $CO_2$ in the organic solvent resulted in the formation of drug loaded microparticles. It was found that, with decreasing polarity of the incorporated drug, drug loading was lowered as a result of an increase in extraction by SC $CO_2$, with the organic solvent acting as a cosolvent. Polar drugs, such as proteins and peptides, were successfully encapsulated by the ASES process, whereas non-polar drugs failed to be encapsulated and were completely extracted by the SC $CO_2$ and the organic solvent. [Bleich et al., *Production of drug loaded microparticles by the use of supercritical gases with the aerosol solvent extraction system (ASES) process*, J. Microencapsulation, 13, 1996, 131-139.]

Elvassore et al. studied the formation of protein loaded polymeric microcapsules in the SAS process. A model system of insulin and PLA was dissolved in a mixture of DMSO and dichloromethane. The prepared solution was then sprayed into SC $CO_2$ through a 50 μm fused silica nozzle. The results showed that insulin-loaded microspheres with particle size from 0.5 to 2 μm were produced and the incorporation efficiency was as high as 80%. [Elvassore et al., *Production of protein-loaded polymeric microcapsules by compressed $CO_2$ in a mixed solvent*, Ind. Eng. Chem. Res., 40, 2001, 795-800.]

Ghaderi et al. studied the formation of microparticles with hydrocortisone loaded in DL-PLA polymer using a combination of SC $N_2$ and $CO_2$ as the antisolvent in a SEDS process. It was shown that microparticles of size less than 10 μm were produced. Hydrocortisone was successfully entrapped in DL-PLA microparticles with a loading efficiency up to 22%. The combination of SC $N_2$ and $CO_2$ was found to facilitate a more efficient dispersion of the polymer solutions than SC $CO_2$ alone. [Ghaderi et al., *A new method for preparing biodegradable microparticles and entrapment of hydrocortisone in D,L-PLG microparticles using supercritical fluids*, European J. of Pharm. Sci., 10, 2000, 1-9.]

More recently, Tu et al. attempted the microencapsulation of para-hydroxybenzoic acid (β-HBA) and lysozyme with PLA in an ASES process. The drug solution, polymer solution and SC $CO_2$ were delivered through a specially designed coaxial multiple nozzle. Higher loading efficiency of 15.6% was achieved for lysozyme encapsulation, while the β-HBA was poorly encapsulated with an efficiency of 9.2%. [Tu et al., *Micronisation and encapsulation of pharmaceuticals using a carbon dioxide antisolvent*, Powder Technol. 126, 2002, 134-149.]

Most of the reported research on the formation of drug loaded microspheres for controlled drug release has focused on the co-precipitation of the solute of interest (drug) and the carrier polymer using an antisolvent process. However, since a SAS co-precipitation process requires the dissolution of both the drug and the polymer in a solvent, this creates a challenge for proteins since many proteins are insoluble in organic solvents. Also, many organic solvents can denature the protein's bioactivity. Moreover, the co-precipitation of two different solutes is difficult to achieve except when the two solutes have similar thermodynamic properties and undergo similar precipitation pathways.

Thus, despite efforts to date, a need remains for effective and reliable systems and/or methods for coating and/or encapsulating nanoparticles and other ultrafine particles. In addition, a need remains for effective and reliable systems and/or methods for coating and/or encapsulating nanoparticles and other ultrafine particles, while controlling agglomeration levels. Moreover, an ability to optimize operating conditions and/or operating parameters in implementation of SAS coating processes is highly desirable. These and other objectives are met by the systems and methods disclosed herein.

SUMMARY OF THE DISCLOSURE

The present disclosure is directed to a method, process and system for producing polymer coated nanoparticles and/or other ultrafine particles through the use of a supercritical fluid, e.g., supercritical carbon dioxide, as an antisolvent. According to an exemplary embodiment of the present disclosure, a solution that includes a polymer and an organic solvent in which nanoparticles/ultrafine particles are suspended is added to the supercritical fluid. The nanoparticles/ultrafine particles are typically substantially insoluble in the organic solvent.

The polymeric coating of the nanoparticles/ultrafine particles is generally effected when the particle-containing suspension is added to the supercritical fluid or otherwise combined therewith. Combination of the particle-containing suspension with the supercritical fluid advantageously causes the suspended nanoparticles/ultrafine particles to precipitate as coated nanoparticles/ultrafine particles. The disclosed system/method is effective to coat or encapsulate ultrafine particles (sub-micron and nanoparticles) so as to modify their surface properties by using a supercritical fluid, e.g., supercritical carbon dioxide (SC $CO_2$), in an enhanced supercritical antisolvent (SAS) process. In an exemplary embodiment of the present disclosure, SC $CO_2$ is employed as the supercritical fluid to effect the desired coating/encapsulation, thereby benefiting from properties associated therewith, e.g., relatively mild critical conditions (T c=304.1 K, Pc=7.38 MPa), non-toxicity, non-flammability, recyclability and cost effectiveness.

The advantageous SAS process of the present disclosure generally employs principles associated with SC $CO_2$ induced phase separation. Thus, according to the present disclosure, the solute precipitates due to a high super-saturation produced by the mutual diffusion of organic solvent into SC $CO_2$ (and vice versa) when an organic liquid solution comes into contact with SC $CO_2$. Of note, the organic solvent can be almost completely removed by simply flushing with a pure gas, e.g., pure $CO_2$ in the case of a SC $CO_2$-based method and/or system. Thus, dry particles may be produced after a $CO_2$ extraction step (flushing) following feeding of the organic solution.

According to exemplary implementations of the present disclosure, submicron particles are successfully coated or encapsulated in the form of loose agglomerates. It was found that the polymer weight fraction and polymer concentration play a critical role in the agglomeration of the coated particles. A high polymer weight fraction favors agglomeration of the coated particles and an uneven distribution of the polymer coating. A low polymer concentration, e.g., on the order of 4.0 mg/ml, appears to prevent and/or minimize agglomeration among the coated particles. The operating pressure and temperature were also found to influence agglomeration. A higher pressure facilitates the agglomeration of coated particles due to sintering because the glass transition temperature of the polymer, $T_g$, is depressed. The operating temperature appeared to have little effect on the agglomeration of the coated particles when the temperature is below the glass transition temperature; however, when the operating temperature is above $T_g$, the polymer coating on the surface of particle appears to be sintered causing strong agglomeration. The flow rate of the polymer suspension was found to have little effect on agglomeration. The inclusion of a surfactant in the disclosed system (PFA, PFS, Krytox, PDMS, and Pluronic 25R2) did not function to suppress agglomeration and, in the case of PFA, PFS, and Krytox surfactants, agglomeration of the coated nanoparticles/ultrafine particles was promoted.

The system and method of the present disclosure is particularly useful in the field of pharmaceuticals, where controlled release systems in association with drugs, genes, and other bioactive agents provide multiple benefits, e.g., protection from rapid degradation, targeted delivery, control of the release rate, and prolonged duration of bioactive agents. Other fields utilizing nanoparticle technology also stand to benefit from the system and method of the present disclosure, including the food industry and food-related applications, the chemical industry and chemical-related applications, the pesticide industry and pesticide-related applications, the polymer industry and polymer-related applications, the coating industry and coating-related applications and the catalyst industry and catalyst-related applications.

A further exemplary application for the disclosed coating/encapsulation system and method of the present disclosure involves processing of conductive inks and/or coatings that contain metallic nanoparticles. Such nanoparticles generally require and/or benefit from passivation by a polymer film for protection, but when exposed to conventional heats of application, can melt away, allowing for a conductive sub-structure of the coatings. An additional exemplary application for the disclosed coating/encapsulation system and method of the present disclosure involves the processing of energetic materials (e.g., propellants and explosives) that employ or include nanosized metallic particle (e.g., aluminum or magnesium) that require and/or benefit from passivation to avoid oxidation.

Additional advantageous features and functionalities associated with the disclosed system and method for nanoparticle/ultrafine particle processing will be apparent from the detailed description which follows.

BRIEF DESCRIPTION OF THE FIGURES

So that those having ordinary skill in the art to which the present disclosure pertains will more readily understand the disclosure described herein and methods, processes and systems for implementation thereof, exemplary embodiments thereof will be described with reference to the appended figures, wherein:

FIG. 17 is a table setting forth processing conditions associated with (i) an exemplary SAS coating process according to the present disclosure, and (ii) a control co-precipitation process;

FIG. 23 is a table setting forth encapsulation efficiency data for coated drug particles and co-precipitated particles;

FIG. 27 is a table setting forth operating conditions according to exemplary aspects of the present disclosure (without surfactant);

FIG. 28 is an additional table setting forth operating conditions according to exemplary aspects of the present disclosure (with surfactant);

FIGS. 34(a), 34(b) and 34(c) are exemplary SEM micrographs of coated silica particles at different polymer weight fractions: (a) 25.0% (Run 1; ×134,170), (b) 16.7% (Run 2; ×62,900), and (c) 12.5% (Run 3; ×97,210);

DETAILED DESCRIPTION OF EXEMPLARY EMBODIMENT(S)

Figure 1:
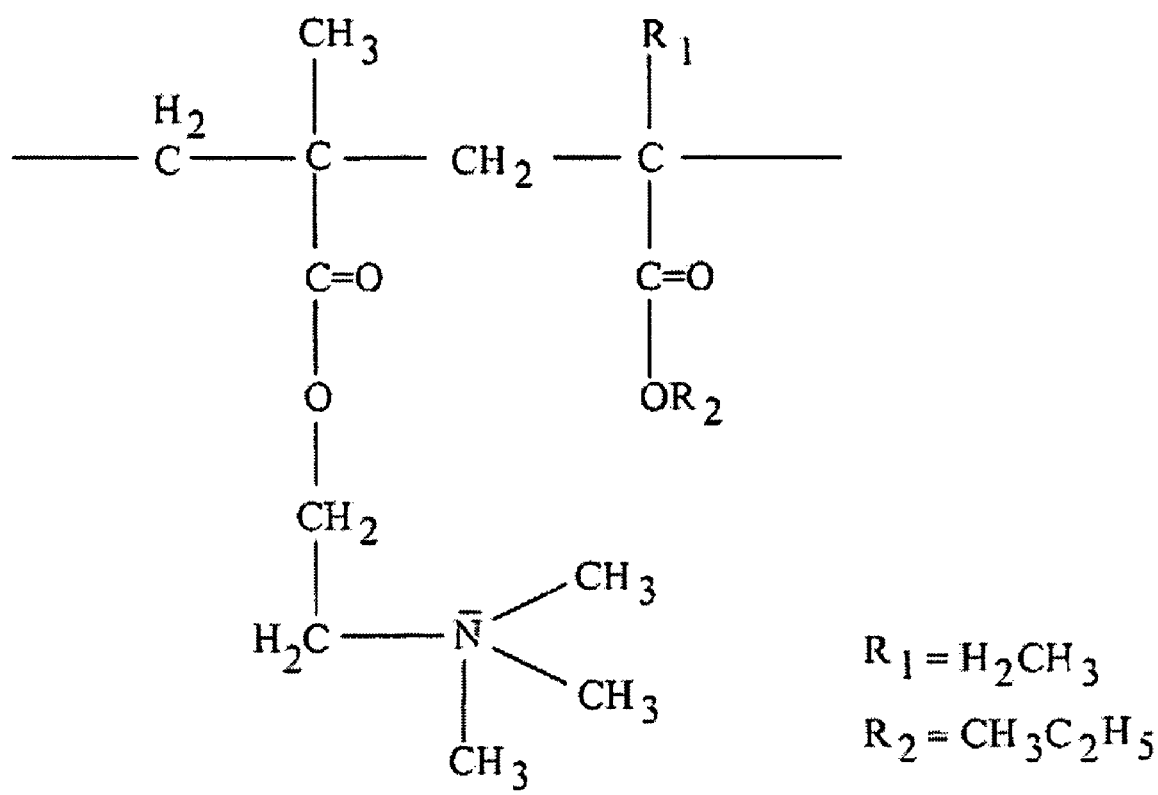
FIG. 1 is a schematic diagram of the chemical structure for a coating material in accordance with an exemplary aspect of the present disclosure.

The present disclosure provides an advantageous system and method for producing polymer coated nanoparticles and/or other ultrafine particles through the use of a supercritical fluid, e.g., supercritical carbon dioxide, as an antisolvent. Coating or encapsulation of nanoparticles and/or other ultrafine particles as disclosed herein advantageously facilitates control and/or management of physical properties of the particles processed thereby. Through control, management and/or modulation of such particle properties, numerous particle attributes and/or functionalities may be improved and/or enhanced, e.g., flowability, dissolution rate, dispersability, chemical reactivity, bio-efficacy and/or hydrophilicity. The system and method of the present disclosure has wide ranging applicability, e.g., for coating and/or encapsulation of pharmaceuticals, cosmetics, food products, chemicals, agrochemicals, pesticides, polymers, coatings, catalysts and the like.

Exemplary applications of the system and method of the present disclosure include the preparation of acrylate-methacrylate copolymer coated silica. The nonoparticles may be used for making pharmaceutical, for cosmetics such as sunscreen vehicles or for making coated pharmaceutical products such as for inhalation therapy, for controlled release products or for the formulation of slightly soluble or insoluble pharmaceuticals. In addition, the disclosed system and method may be advantageously used in processing of conductive inks and/or coatings that contain metallic nanoparticles, e.g., wherein the nanoparticles require and/or benefit from passivation by a polymer film for protection, and in processing of energetic materials (e.g., propellants and explosives) for passivation of nanosized metallic particle (e.g., aluminum and/or magnesium) avoid and/or minimize oxidation thereof. Other polymers and/or other nanoparticles may also be used in accordance with other aspects of the present disclosure to provide any of a variety of different effects.

Preferably, any solid pharmaceutical may be prepared as a polymer coated nanoparticle using the system and/or process of the present disclosure. Polymers which provide for the immediate, delayed or continuous release of pharmaceuticals may preferably be applied to solid nanoparticles of the pharmaceutical using the process of the present disclosure. Useful polymers which may preferably be applied to nanoparticles include, for example, acrylic and methacrylic acid polymers and copolymers, polylactic acid copolymers (PLA) and polylactic glycolic acid (PLGA) and polymers specified on the FDA GRAS list, which is incorporated by reference. For products to be used as industrial products, film forming polymers which are soluble or dispersible in solvents may preferably be used.

Preferably, it is possible to apply a polymer coating to a nanoparticle wherein the total weight of polymer based on the weight of the coated nanoparticle is from 1-100 weight percent. The coated nanoparticle may comprise all of the active pharmaceutical or it may include from 1-50 weight percent of a suitable diluent or filler such as lactose, dextrose, microcrystalline cellulose, and the like based on the total weight of the nanoparticle. The polymer may be dissolved in an organic solvent that is soluble in a supercritical fluid. Any supercritical fluid may be utilized including, for instance, ammonia and/or carbon dioxide.

To illustrate the efficiency and efficacy of the SC $CO_2$ SAS coating process in accordance with the present disclosure, both hydrophobic and hydrophilic silica nanoparticles of different sizes from Degussa, USA and Catalysts & Chemicals Ind. Co., Japan, may, for example, be used as host particles. The following silica nanoparticles were employed in experimental runs:

| | CATALYSTS & CHEMICALS (JAPAN) | DEGUSSA (USA) | DEGUSSA (USA) |
| --- | --- | --- | --- |
| TRADE NAME | COSMO 55 | AEROSIL 90 | AEROSIL R972 |
| PARTICLE SIZE (nm) | 600 | 20 | 16 |
| SURFACE PROPERTY | Hydrophilic | Hydrophilic | Hydrophilic |

Eudragit® RL 100 (Rohm America LLC, USA), a copolymer of acrylate and methacrylate, with an average molecular weight of 150,000, may, for example, be used as a polymer or coating material. The chemical structure of Eudragit® RL 100 is shown in FIG. 1. Bone-dry grade liquid $CO_2$ provided by Matheson Gas, USA, may, for example, be used as an antisolvent. While HPLC grade acetone provided by Fisher, USA may, for example, be used as an organic solvent into which the coating material may preferably be added. All of the materials may preferably be used as received requiring no further treatment.

Figure 2:
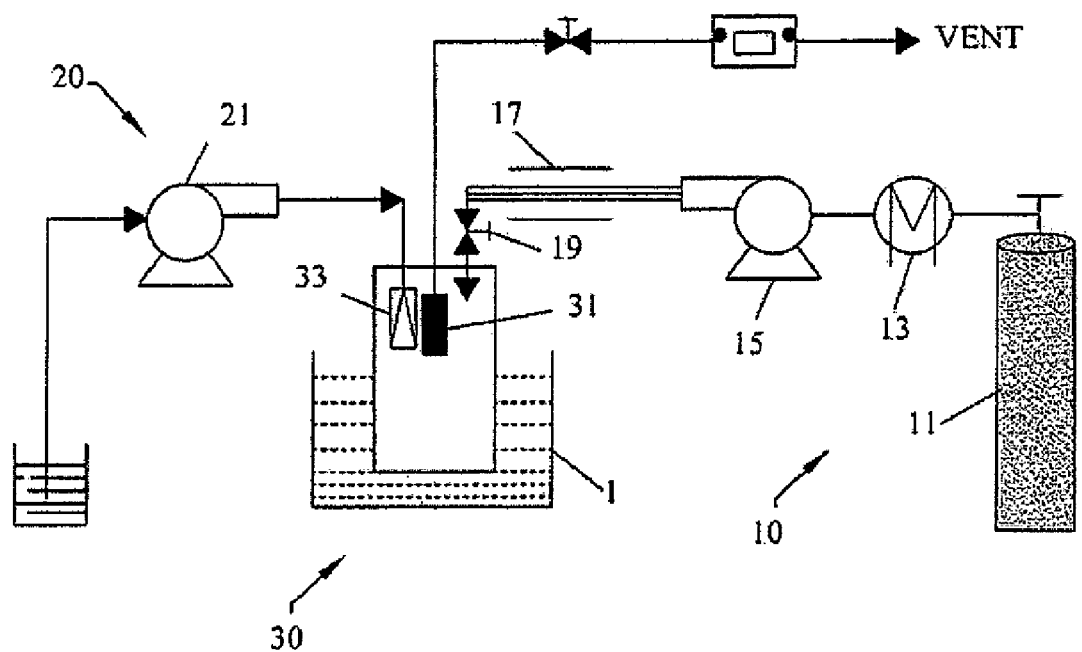
FIG. 2 is a schematic diagram of an experimental set-up for a nanoparticle coating process using SAS in accordance with an exemplary aspect of the present disclosure.

Referring to FIG. 2, a set-up in accordance with an illustrative aspect of the present disclosure preferably has a $CO_2$ supply system 10, a solution delivery system 20, and at least one high-pressure vessel 30, such as a high pressure vessel provided by Parr Instruments, USA, preferably with capacity of 1,000 ml. The $CO_2$ supply system 10 preferably has a $CO_2$ storage container 11, a cooling means 13, a $CO_2$ pump 15, a heating means 17, and a control valve 19. Other components may be added to and identified components may be removed from the $CO_2$ supply system 10 as needed in order to obtain a desired result. Further, the solution delivery system 20 preferably has at least a high pressure pump 15 operatively connected to a solution storage container 11. As with the $CO_2$ supply system, other components may be added to and identified components may be removed from the solution delivery system 20, as needed in order to obtain a desired result. The high-pressure vessel 30 is preferably operatively associated with a filter 31 and a capillary tube 33.

In operation, the high-pressure vessel 30 is preferably immersed in a water-bath to keep the temperature constant during the process. The $CO_2$ pump 15, which may be, for example, a Model EL-IA metering pump, by AMERICAN LEWA®, USA, is preferably used to deliver liquefied $CO_2$ from the $CO_2$ storage container 11 to the high-pressure vessel 30. However, before entering the pump head the liquefied $CO_2$ is preferably cooled down to around zero degrees Centigrade by cooling means 13 (e.g., a refrigerator (NESLAB, RTE-111) or the like) to preferably minimize cavitation. After leaving the pump head, the liquefied $CO_2$ is then preferably pre-heated via heating means 17 (e.g., a heating tape (Berstead Thermolyne, BIH 171-100), a conductive wire or the like).

A polymer solution of, for example, a dissolved Eudragit RL-100 in acetone with silica nanoparticles suspended therein to produce the desired ratio of polymer to silica particles by weight may be used by way of illustration. Since the 600 nm silica particles possess less surface area than 16-20 nm silica, less polymer is required to coat the 600 nm silica nanoparticles. Therefore, 14-20% by weight of polymer may be used for coating the 600 nm silica as compared with 33-50% for coating the 16-20 nm silica. An ultrasonicator may be used to break up the nanoparticle agglomerates in the silica-acetone suspension. During the process the temperature and pressure are preferably kept constant at, for example, 305.5 K and 8.27 MPa, respectively. When steady state conditions are reached in the high-pressure vessel 30, i.e., the pressure and temperature of the $CO_2$ become stable, the suspension (i.e., the polymer solution with nanoparticles suspended throughout) may be delivered by the high-pressure pump 21 (e.g., a Beckman, 110B pump) at a rate of 0.7 ml/min, for example, and sprayed through the capillary tube 33 (e.g., a stainless steel capillary nozzle (125 μm ID)) into the high-pressure vessel 30. The spraying may last about 20 min followed by another 30 min for settling. However, different spraying durations may also be used as appropriate to achieve different effects. Thereafter, $CO_2$ may be supplied at a rate of less than 3.0 standard liters/min to preferably remove any residual organic solvent. The cleaning step is preferably continued for about 3 hours (e.g., at a $CO_2$ flow rate of 1.8 standard liters/min) depending on the $CO_2$ flow rate and the temperature. However, the cleaning step may be continued for different durations as appropriate to achieve different effects. The higher the flushing velocity and the higher the temperature, the less flushing time is required. When the cleaning step is completed, the high-pressure vessel 30 may preferably be slowly depressurized and samples collected for characterization. The test conditions are summarized below.

| Experiment | Polymer Concentration (g/100 ml) | Ratio of Polymer to Nanoparticles (g/g) |
| --- | --- | --- |
| Coating of 16 nm hydrophobic silica | 0.8 | 1:2 |
| Coating of 20 nm hydrophilic silica | 0.8 | 1:1 |
| Coating of 600 nm hydrophilic silica | 0.4 | 1:4 |
| Coating of 600 nm hydrophilic silica | 0.4 | 1:5 |
| Coating of 600 nm hydrophilic silica | 0.4 | 1:6 |

A high-resolution field emission scanning electron microscope (FE-SEM) (Jeol, JSM-6700F) is preferably used for morphological observations since the primary particles are less than 100-nm. Specimens are preferably sputter coated with palladium (SPI Sputter) for 20 s to make the surface conductive without compromising fine surface microstructure. A nonconductive surface would produce a severe surface charge problem under the high intensity electron beam and accumulated surface charge would cause abnormal contrast, image deformation and distortion. A Leo 922 Omega Transmission Electron Microscope (TEM) may also be used to examine the structure of the encapsulated nanoparticles.

Fourier Transform-Infrared (FT-IR) spectroscopy measurements may be carried out using a Spectrum One FT-IR Spectrometer (Perkin Elmer Instruments) with PERKIN ELMER V3.02 Software Spectrum for control of the instrument, data acquisition and analysis. The spectra may be taken in the range of 400-4000/cm using a resolution of 8/cm and 25 scans. The spectra of the polymer, uncoated and coated silica nanoparticles may be measured as pellets. The pellets of uncoated and coated silica nanoparticles may be made by mixing them with ground KBr at a ratio of 0.85% (w/w) and may be pressed by a press kit (International Crystal Laboratories) and a 12-ton hydraulic Carver Laboratory Press (Fred S. Carver Inc.). KBr has no absorbance in the IR range, and preferably serves as a diluent for the solid samples. In preparing the polymer specimen, Eudragit RL-100 pellets may be ground into powder using a mortar and pestle. The ground Eudragit RL-100 may then be mixed with ground KBr at a ratio of 0.5% (w/w). Afterward, the mixture can be made into a pellet for characterization.

Figure 3:
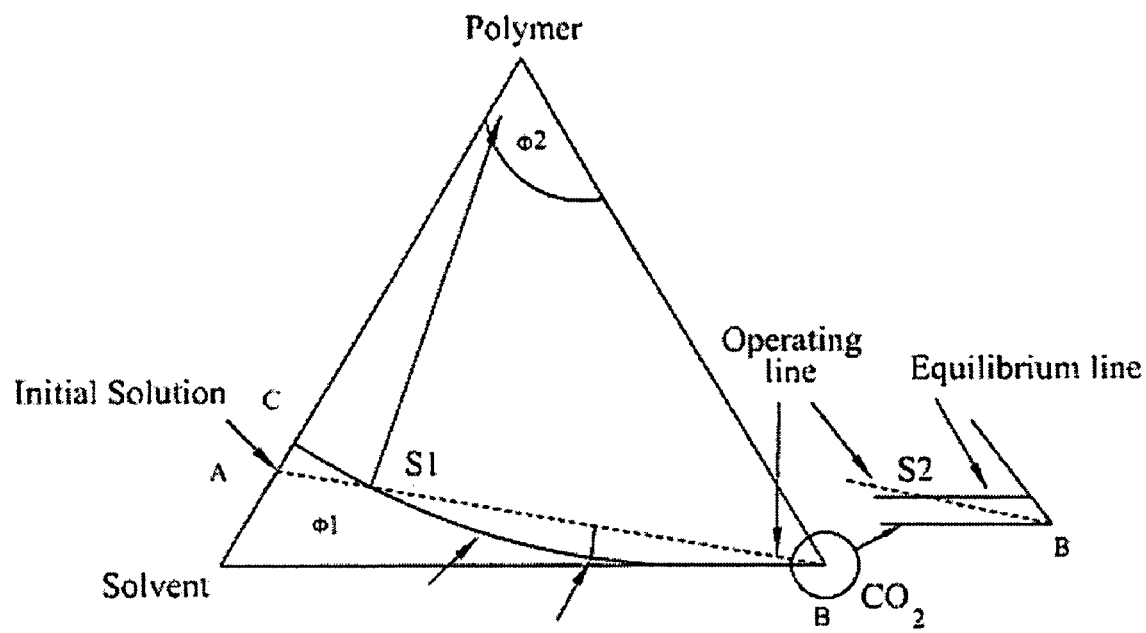
FIG. 3 is a typical ternary phase diagram for solvent-polymer-$CO_2$ at constant P and T.

In the SAS process, SC $CO_2$ preferably acts as an antisolvent, which is dissolved in an organic solvent, preferably reducing the solvent strength significantly leading to a high degree of super-saturation and nucleation of the solute. [See, C. J. Chang, A. D. Randolph, *Solvent expansion and solute solubility predictions in gas-expanded liquids*, AIChE J. 36 (1990) 939]. While the actual SAS process is complicated due to the interplay of thermodynamics, mass transfer, and hydrodynamic effects [D. J. Dixon, et al.], a schematic phase diagram of SC $CO_2$, solvent and solute at constant temperature and pressure is useful to understand the SAS process and is shown in FIG. 3. In this example, SC $CO_2$ is preferably completely miscible with the solvent, while the polymer solubility in SC $CO_2$ is preferably very limited. Generally, almost all polymers have very low solubility even at 323 K and 30 MPa [D. J. Dixon, et al.]. In the diagram of FIG. 3, the one-phase region $\Phi 1$ preferably represents the polymer dissolved in solvent, forming a polymer solution with some $CO_2$ dissolved in the solution. Region $\Phi 2$ is glassy region, a polymer-rich phase, with a small amount of $CO_2$ and solvent preferably absorbed in the polymer. In the two-phase region, solvent-rich phase $\Phi 1$ and polymer-rich phase $\Phi 2$ coexist and are in equilibrium.

The bold line (from C to B) in FIG. 3 preferably represents the polymer solubility in the mixture of solvent and SC $CO_2$. The dotted straight line is preferably an operating line that represents the addition of polymer solution into SC $CO_2$ (from A to B). During the addition of polymer solution into SC $CO_2$, an initial very small amount of solute will preferably be dissolved in SC $CO_2$ with the solvent preferably acting as co-solvent $\Phi 1$ region until the saturation of polymer in the mixture of SC $CO_2$ and solvent is reached (Sl, saturation point). Continued feeding of the solution into SC $CO_2$ preferably results in crossing over the equilibrium boundary and super-saturation of the polymer in the mixture of SC $CO_2$ and solvent. Subsequently, a phase transition will preferably take place, depending on the starting conditions. The phase transition will preferably occur initially either by nucleation, an activated process in which a free energy barrier must be surmounted, or by spinodal decomposition, a spontaneous process in which no free energy barrier must be overcome [E. Kiran, P. G. Debenedetti, C. J. Peters, *Supercritical Fluids: Fundamentals and Applications*, NATO Science Series, E 366, Kluwer Academic Publishers, 2000]. In either case nucleation and precipitation of polymer induced by the phase transition will preferably take place on the surface of the nanoparticles, preferably forming a thin layer of polymer coating.

In one aspect of nanoparticle coating or encapsulation with polymer using the SAS coating process in accordance with the present disclosure, the polymer solution with suspended nanoparticles is preferably sprayed through a nozzle. If the solvent and the SC $CO_2$ are completely miscible and the operating conditions are above the critical point of the mixture, distinct droplets will preferably never form as reported by Lengsfeld et al. [C. S. Lengsfeld, J. P. Delplangue, V. H. Barocas, T. W. Randolph, *Mechanism governing microparticle morphology during precipitation by a compressed antisolvent: atomization vs. nucleation and growth*, J. Phys. Chem. 104 (2000) 2725-2735] and Bristow et al. [S. Bristow, T. Shekunov, B. Yu. Shekunov, P. York, *Analysis of the supersaturation and precipitation process with supercritical $CO_2$*, J. Supercrit. Fluids 21 (2001) 257-271] and the polymer will preferably nucleate and grow within the expanding gas plume. However, results may differ depending on changes in temperature and/or pressure conditions. For example, at a temperature of 32.5° C. and a pressure of 8.27 MPa, which is preferably in the partially miscible region for a mixture having a critical point of 35.0° C. and 7.32 MPa, at least some droplets may exist. See, [J. J. Luo, F. Chavez, C. Zhu, R. Dave, R. Pfeffer, P. G. Debenedetti, *On jet behavior below and above the critical point of a solvent-antisolvent mixture*, submitted for publication], which illustrates that a transient jet and jet-induced droplets may exist even when the pressure is slightly above the mixture critical pressure. It was observed that only when the pressure is at least somewhat above the mixture critical pressure does the flow behave like a single-phase gaseous jet without any definable interfacial boundaries or the formation of droplets. Accordingly, droplets of polymer solution with entrapped nanoparticles may be generated due to jet break-up depending on temperature and/or pressure parameters.

When a droplet contacts the SC $CO_2$, since acetone, which is used by way of example, is highly miscible with SC $CO_2$, preferably a very fast mutual diffusion into and out of the droplet occurs. The polymer solution in the droplet preferably approaches saturation very rapidly due to the extraction of solvent from the droplet. The subsequent crossing over the equilibrium boundary preferably initiates the gelation of the polymer. Meanwhile, the SC $CO_2$ preferably continuously diffuses into the droplet and is preferably dissolved in the acetone solution. This process preferably leads to swelling of the droplet [T. W. Randolph, A. J. Randolph, M. Mebes, S. Young, *Sub-micrometer-sized biodegradable particles of poly(L-lactic acid) via the gas antisolvent spray precipitation process*, Biotechnol. Progress 9 (1993) 429].

Figure 4:
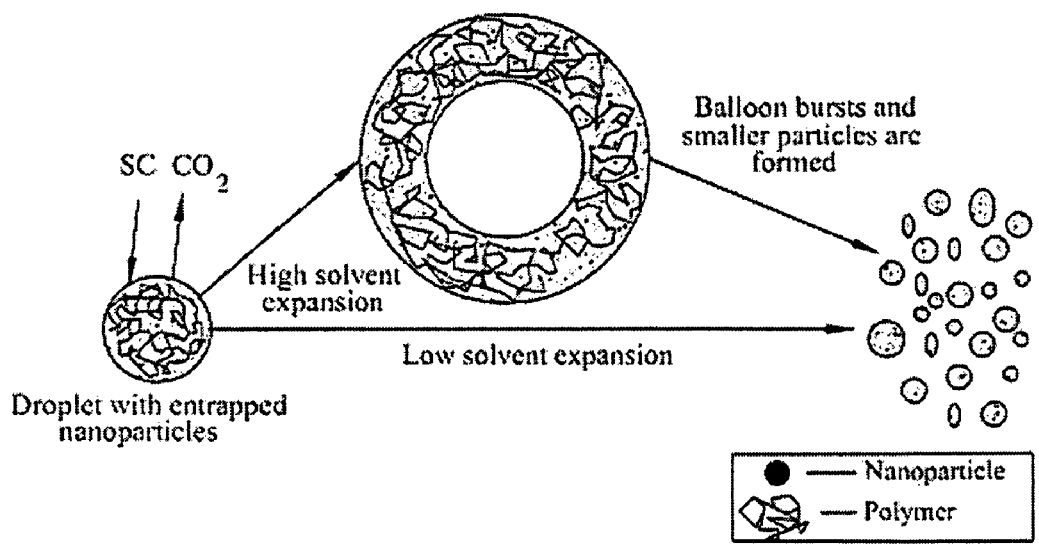
FIG. 4 is a schematic diagram of a possible mechanism for fine particle encapsulation using SAS in accordance with an exemplary aspect of the present disclosure.

When the solvent expansion is high, Reverchon [E. Reverchon, *Supercritical antisolvent precipitation of micro- and nana-particles*, J. Supercrit. Fluids 15 (1999) 1] proposed that an empty shell or balloon structure may be formed due to the interplay of mass transfer and the phase transition. This empty shell structure may be clearly observed in experiments using the SC $CO_2$ SAS process for particle formation (see FIG. 6 of E. Reverchon). The stability of the balloon structure preferably depends mainly on the expansion of the solvent by SC $CO_2$, which preferably depends on the miscibility of the solvent and SC $CO_2$. In one aspect of the present disclosure, acetone, which is preferably highly miscible with SC $CO_2$, may be used as the solvent for the polymer. Thus, it may be highly probable that a balloon structure was formed which then preferably burst into very fine viscous droplets containing nanoparticles and polymer as illustratively shown in the diagram of FIG. 4.

Preferably, further extraction of the solvent by SC $CO_2$ from the gelled droplets containing nanoparticles induces the glass transition of the polymer. Therefore, the nanoparticles may preferably be encapsulated, within a polymer film attributed to the nucleation and precipitation of polymer on the surface of the nanoparticles. However, the encapsulated nanoparticles within the polymer film may be aggregated and agglomeration may take place. Thus, a nanocomposite with a matrix structure may be formed with the nanoparticles as the host particles and the polymer as a coating. As described below, optimized process parameters are disclosed for control and/or modulation of the resultant matrix structure, for example, to generate less agglomeration of submicron particles that are coated or encapsulated according to the system and method of the present disclosure.

Coating of Hydrophobic Silica Nanoparticles

Figure 5A:
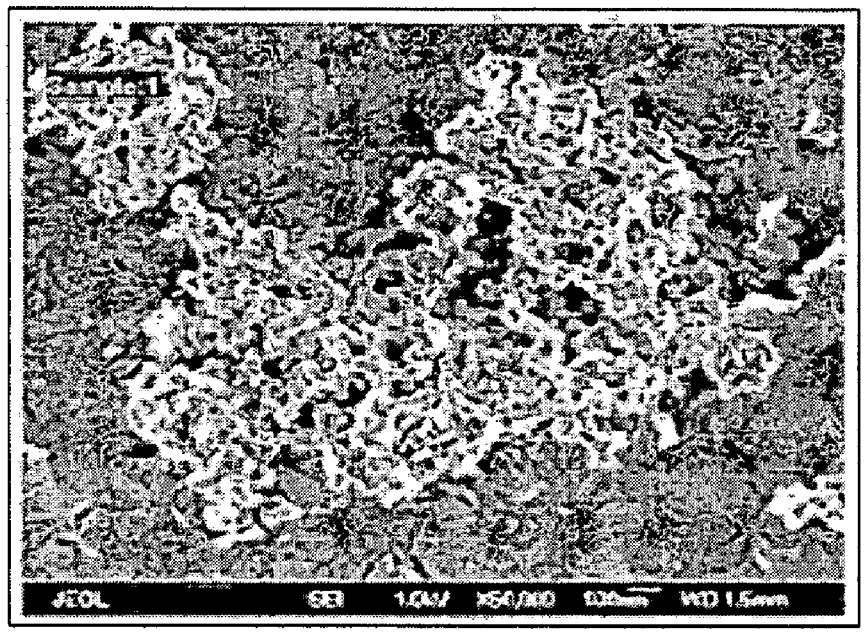
FIGS. 5(a) and 5(b) are exemplary scanning electron microscope (SEM) micrographs of uncoated hydrophobic silica nanoparticles, (a) ×100,000, (b) ×300,000.
Figure 5B:
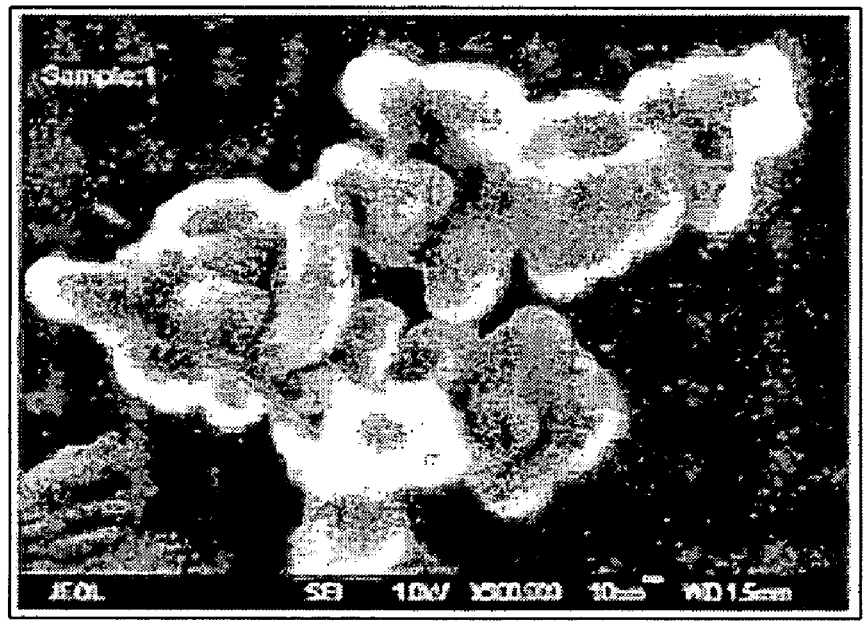

Hydrophobic silica nanoparticles R972 were chosen by way of example to evaluate the coating of nanoparticles with a hydrophobic surface. FIGS. 5(a) and 5(b) show exemplary morphology and size of the hydrophobic silica nanoparticles at two different magnifications. As can be observed, the hydrophobic silica nanoparticles exhibit the typical chained structure. From the scale bar of the higher magnification micrograph the primary particle size can be estimated to be in the range of about 16-30 nm.

Figure 6A:
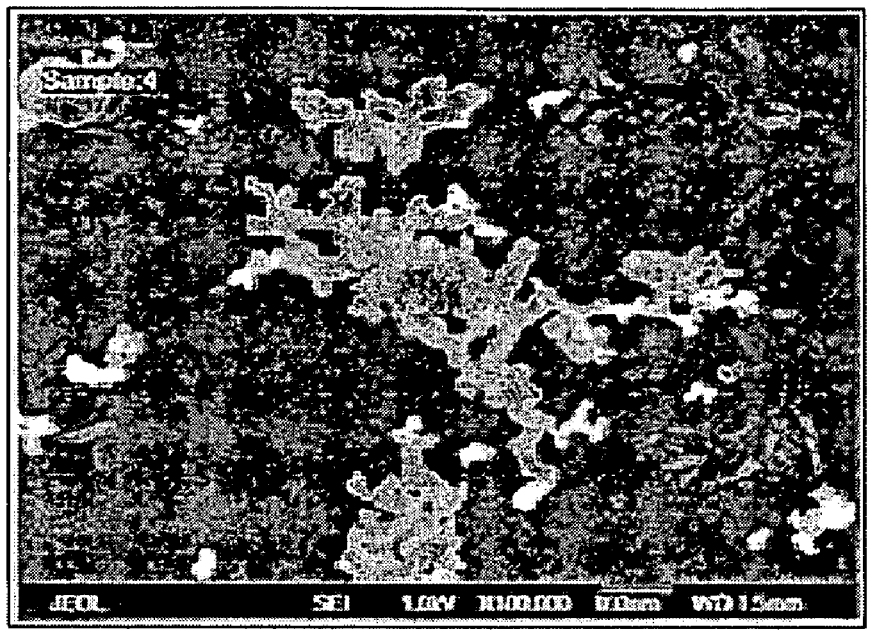
FIGS. 6(a) and 6(b) are further exemplary SEM micrographs of hydrophobic silica nanoparticles coated with Eudragit® (copolymer of acrylate and methacrylate; Rohm America LLC), (a) ×50,000, (b) ×300,000.
Figure 6B:
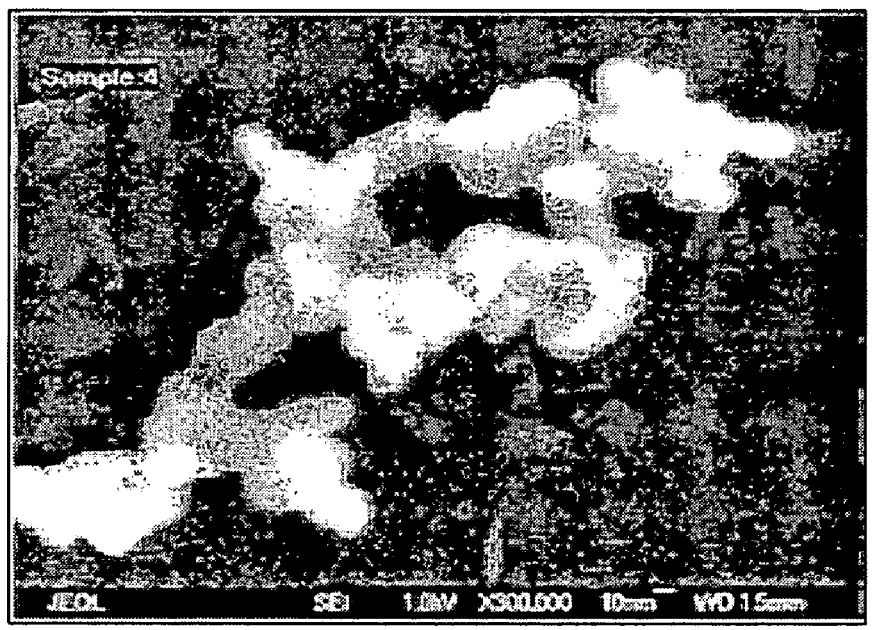

FIGS. 6(a) and 6(b) show exemplary SEM micrographs of the hydrophobic silica nanoparticles coated with Eudragit at two different magnifications. When compared with FIGS. 5(a) and 5(b), the morphology of the coated nanoparticles appears quite different from that of uncoated nanoparticles. Furthermore, the primary particle size of coated hydrophobic silica nanoparticles appears to have increased to about 50-100 nm. The morphological change and size enlargement may be attributed to polymer nucleation and subsequent growth on the surface of the nanoparticles during the SAS coating process, forming a thin film encapsulation. The thickness of the polymer film can be estimated to be around about 10-40 nm.

Figure 7A:
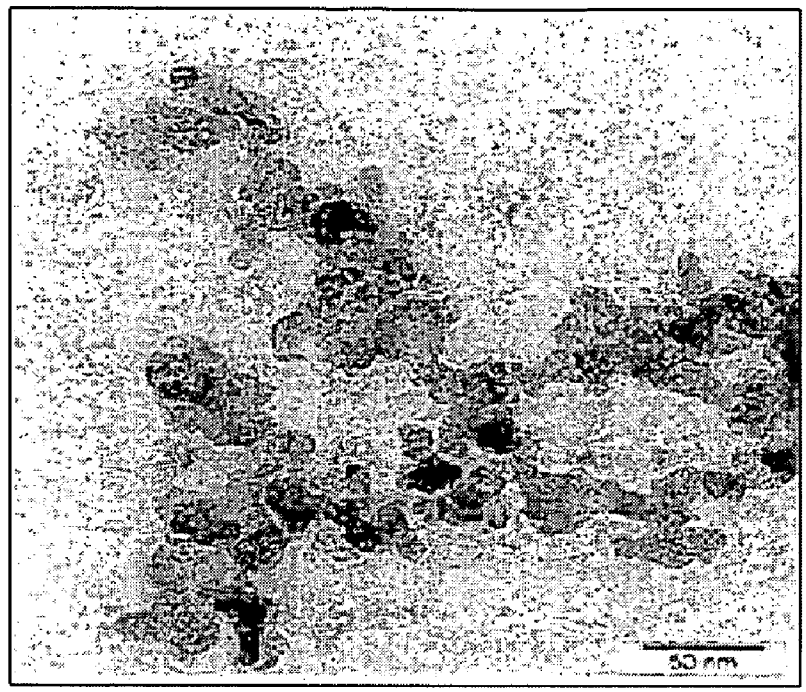
FIGS. 7(a) and 7(b) are exemplary transmission electron microscope micrographs using electron energy loss spectroscopy (TEM-EELS) of uncoated hydrophobic silica nanoparticles, (a) representing zero loss, (b) representing silicon mapping.
Figure 7B:
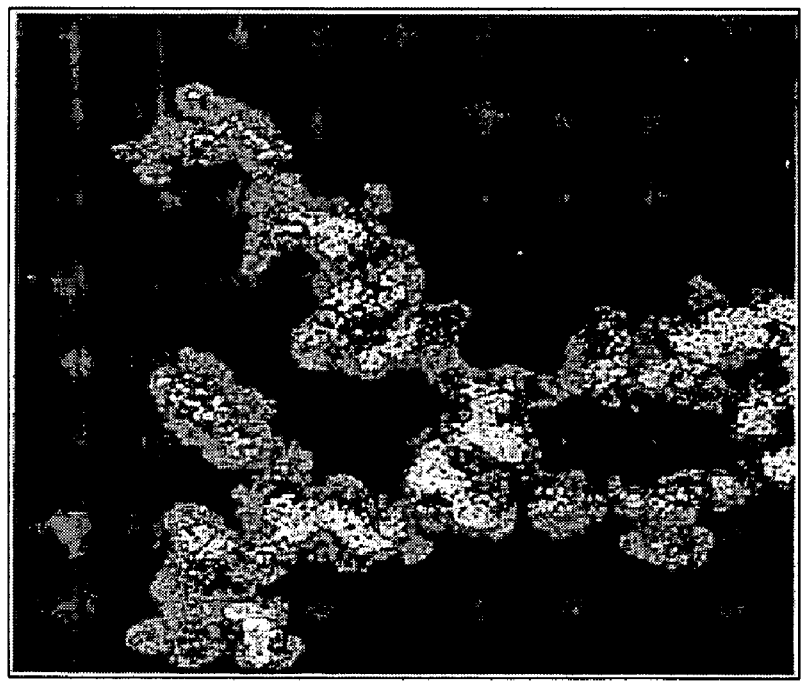
Figure 8A:
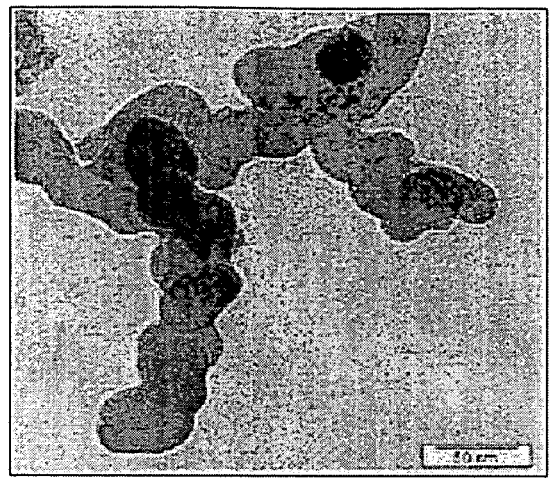
FIGS. 8(a)-8(c) are three exemplary TEM-EELS micrographs of coated hydrophobic silica nanoparticles, (a) representing zero loss, (b) representing silicon mapping, (c) representing carbon mapping.

A TEM-EELS, which is a powerful tool in multi-component material characterization, may be used to characterize the encapsulation of the nanoparticles. In TEM-EELS specimen preparation, a wet method may be employed to achieve a good dispersion. The encapsulated samples may be dispersed in very dilute alcohol, and then may be spread over an extremely thin carbon film (3 nm) supported by a copper grid. Exemplary zero-loss micrographs of uncoated and coated silica nanoparticles are shown in FIG. 7(a) and FIG. 8(a), respectively. Compared with FIG. 7(a), the coated primary particle size shown in FIG. 8(a) can be estimated to be about 50 nm from the scale bar. The silicon mapping illustrated by FIG. 8(b) exhibits the same shape and morphology of the silica nanoparticle agglomerate as the TEM Zero-Loss micrograph illustrated in FIG. 8(a). As one of the major components of the polymer, carbon shows up in a carbon mapping micrograph (FIG. 8(c)). The carbon signal may be generally weaker than the silicon signal because the amount of carbon may be much less than that of silicon. Furthermore, carbon is number six in the periodical table, while silicon is number fourteen, and the higher the atomic number, the stronger the signal response to electrons.

Figure 8B:
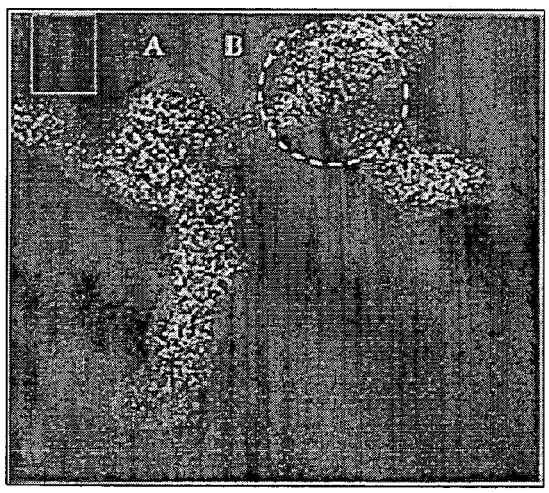
Figure 8C:
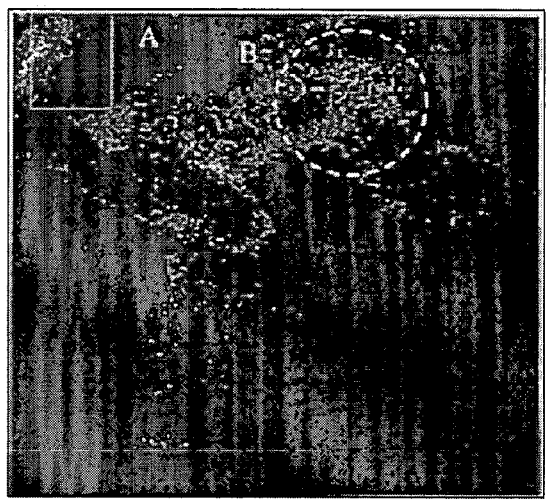

From the carbon mapping, it appears that silica nanoparticles are coated with a thin layer of polymer. Interestingly, the coating layer looks like a shell encapsulating the nanoparticle agglomerate. However, from the carbon mapping, it also appears that the polymer is not uniformly distributed on the surface of the silica nanoparticles. In general, the stronger the carbon signal, the more the polymer has precipitated on the surface of the silica nanoparticles. In region B, it appears that more polymer coating occurs. Another feature in carbon mapping micrograph may be seen at the upper-left corner where an amorphous region A appears, FIG. 8(a). The corresponding carbon signal shown in FIG. 8(c) appears strong, whereas there is practically no silicon signal in the same region as shown in FIG. 8(b). Therefore, it may be concluded that the amorphous region is heavily coated with polymer.

Figure 9:
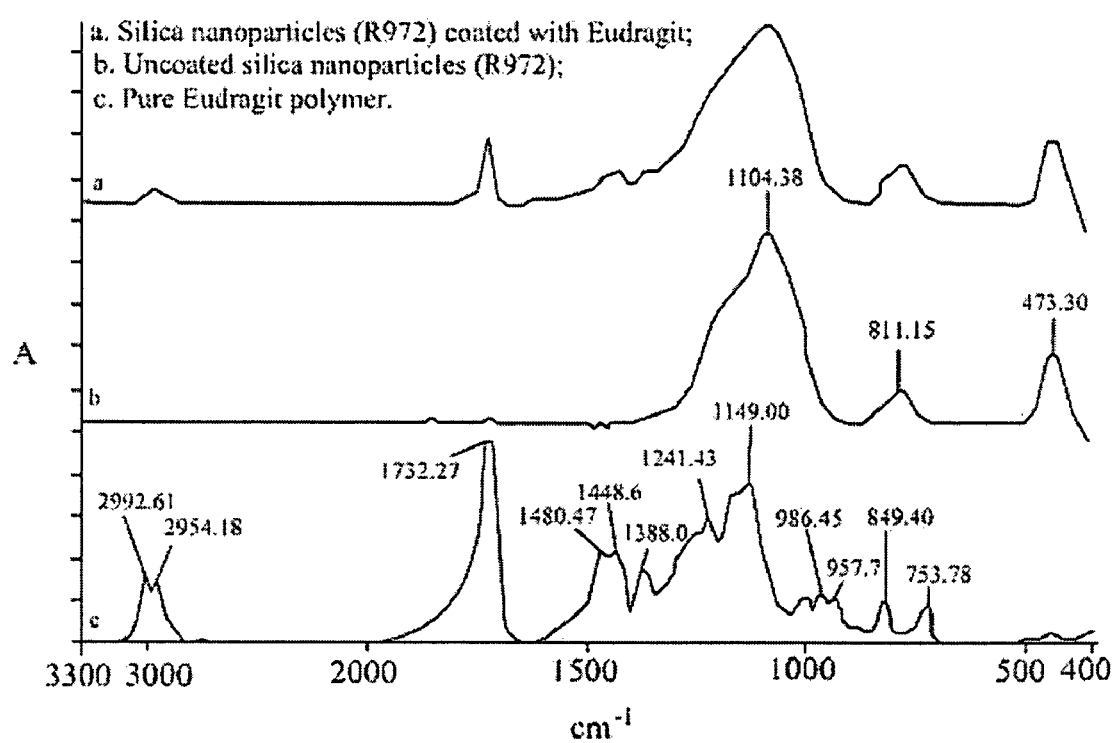
FIGS. 9(a)-9(c) are exemplary Fourier-transform infrared spectroscopic (FT-IR) spectra for hydrophobic silica nanoparticles, (a) representing coated nanoparticles, (b) representing uncoated nanoparticles (R972), (c) representing Eudragit® copolymer.

FT-IR spectrometry may be a valuable characterization tool to determine the chemical composition before and after a coating process. Three sets of FT-IR spectra of silica nanoparticles coated with polymer, uncoated silica nanoparticles, and of the Eudragit RL-100 powder are illustratively shown in FIGS. 9(a)-9(c). The spectrum of Eudragit RL-100, for example, which is a copolymer of acrylate and methacrylate, is shown in FIG. 9(c). The peaks at 2992.61 and 2954.18/cm are the absorbances of the alkyl groups ($-CH_3$ and $-CH_2$) stretching vibrations. The corresponding absorbances of bending vibrations occur at 1480.47, 1448.6 and 1388.0/cm. A major peak at 1732.27/cm may be attributed to the stretching vibration from the carbonyl group. The band between 1300 and 1000/cm may be assigned to the polymer's C—O double bond stretching mode. The peaks before 1000/cm may be fingerprint region of the polymer. The spectrum of silica nanoparticles in FIG. 9(b) shows a major peak at 1104.38/cm, this may be assigned to the Si—O stretching vibration.

When compared with FIG. 9(c), it can be observed in the spectrum of coated silica nanoparticles in FIG. 9(a) that the peaks at 2992.61 and 2954.18/cm associated with alkyl groups' stretching modes and peaks at 1480.47, 1448.6, and 1388.0/cm associated with their bending vibrations show up at exactly the same position as in the spectrum of polymer. The absorbance at 1732.27/cm assigned to carbonyl group stretching vibration can be found in FIG. 9(a). However, the Si—O stretching vibration and the C—O double bond stretching vibration have almost the same absorbance region from 1300 to 1000/cm. The absorbance of the Si—O stretching mode is much stronger than that the C—O, hiding the peaks attributed to C—O. Therefore, C—O double bond peaks do not show up in the spectrum of coated silica nanoparticles. From the FT-IR chemical analysis above, a conclusion can be reached that the surface of silica nanoparticles is coated with polymer, which strongly supports the TEM-EELS observations.

However, it may be observed that no new peak shows up in the spectrum of silica nanoparticles coated with Eudragit RL-100, indicating that there may be no chemical bond between the polymer and the surface of the silica nanoparticles during the process of nanoparticle coating with polymer using the SAS coating process of the present disclosure. The SAS coating process of the present disclosure is preferably a process of polymer nucleation and subsequent growth on the surface of a particle, typically a physical process. Thus, it may be desirable for pharmaceutical applications since any chemical interaction between the coating and the substrate may result in a change in the properties of the pharmaceutical component, which could change the effectiveness of the drug.

Coating of Hydrophilic Silica Nanoparticles

Figure 10A:
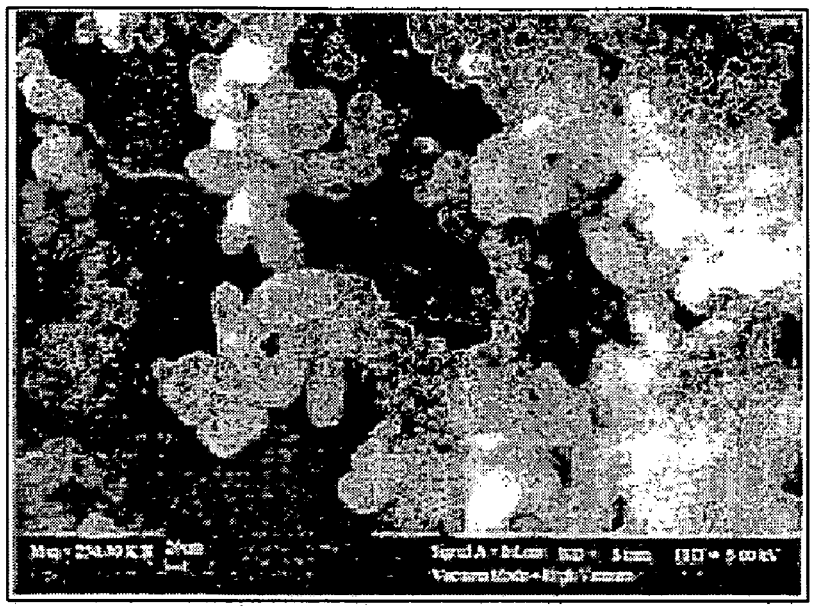
FIGS. 10(a) and 10(b) are exemplary SEM micrographs of hydrophilic silica nanoparticles, (a) representing uncoated ×250,000, (b) representing coated ×200,000.
Figure 10B:
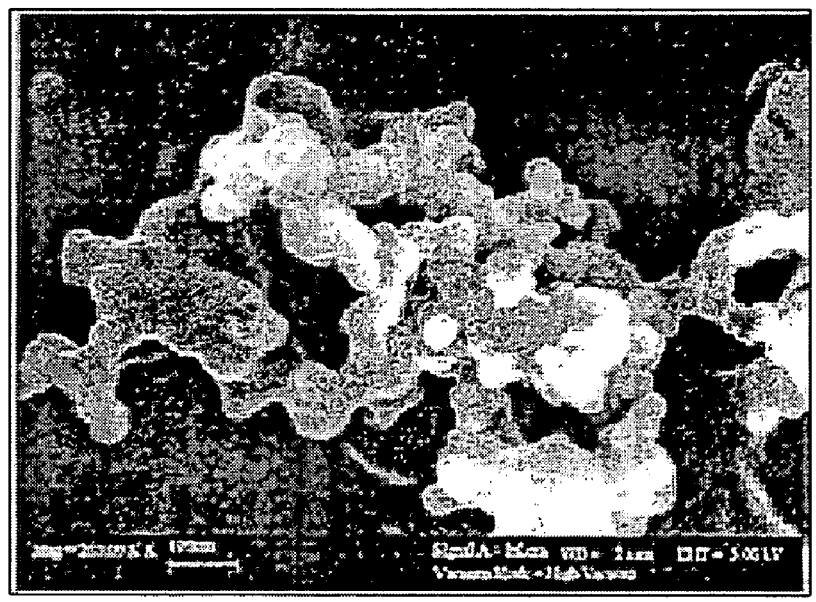

Hydrophilic silica nanoparticles were chosen by way of example to determine the effect of a hydrophilic surface (if any) on coating with polymer in accordance with the present disclosure. The uncoated and coated samples may be examined using the FE-SEM. FIGS. 10(a) and 10(b), for instance, show exemplary SEM micrographs of hydrophilic silica nanoparticles before and after coating. It is clear that morphological change occurred indicating that the hydrophilic silica nanoparticles may be coated with polymer.

Figure 11A:
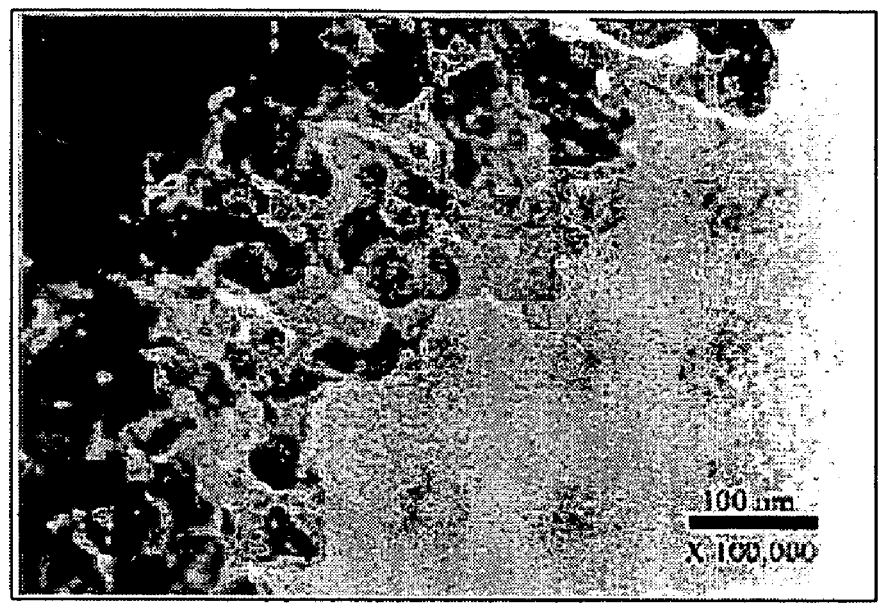
FIGS. 11(a) and 11(b) are exemplary TEM micrographs of hydrophilic silica nanoparticles, (a) representing uncoated ×100,000, (b) representing coated ×100,000.
Figure 11B:
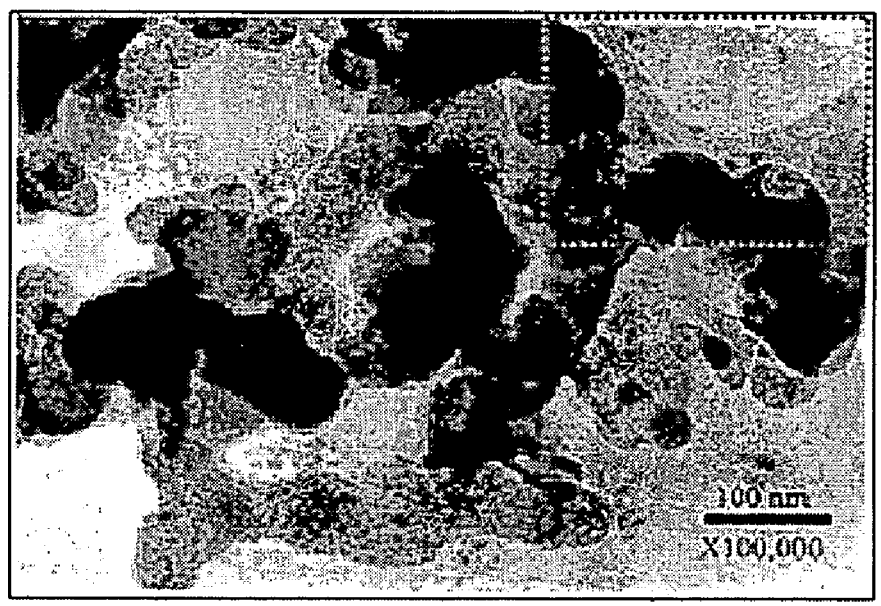

The coated hydrophilic silica nanoparticles may also be characterized using TEM. Exemplary TEM micrographs of hydrophilic silica nanoparticles before and after the SAS coating process of the present disclosure can be seen in FIGS. 11(a) and 11(b), respectively. The most important feature of FIG. 11(b) may be that an amorphous region shows up in the right-upper corner thereof, indicating the polymer phase formed with a matrix structure of embedded silica nanoparticles.

The TEM-EELS technique may be used to distinguish between the thin layer of polymer coating and the hydrophilic silica nanoparticles. Although the wet method may be used for the coated hydrophobic nanoparticles to produce a good dispersion of agglomerated nanoparticles as illustratively shown in FIGS. 8(a) and 8(b), a dry method may also be used for the analysis of the encapsulated hydrophilic silica nanoparticles. In the dry method, a copper grid preferably held by tweezers or the like may be ploughed through the coated silica nanoparticles. The very fine agglomerates of nanoparticles preferably become attached to the copper grid due to Van der Waals and electrostatic forces. This sampling method may be used to better preserve the integrity of the coated silica nanoparticles.

Figure 12A:
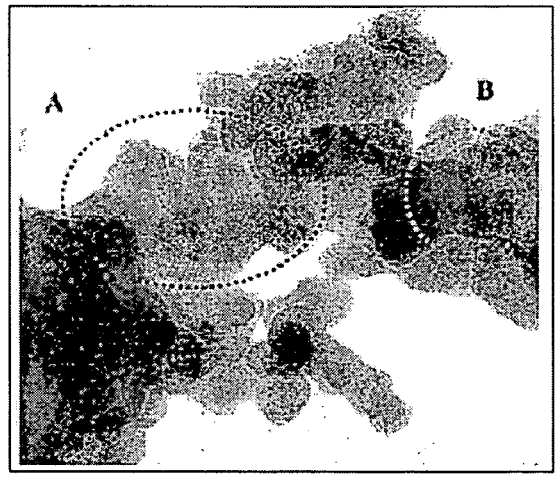
FIGS. 12(a)-12(c) are three exemplary TEM-EELS micrographs of coated hydrophilic nanoparticles, (a) representing zero loss, (b) representing silicon mapping, (c) representing carbon mapping.
Figure 12B:
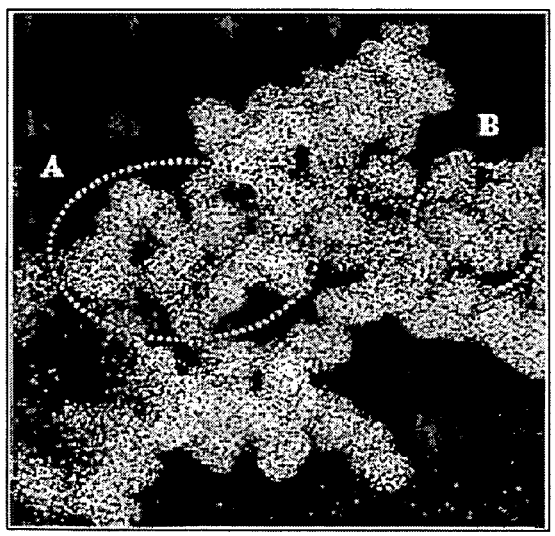
Figure 12C:
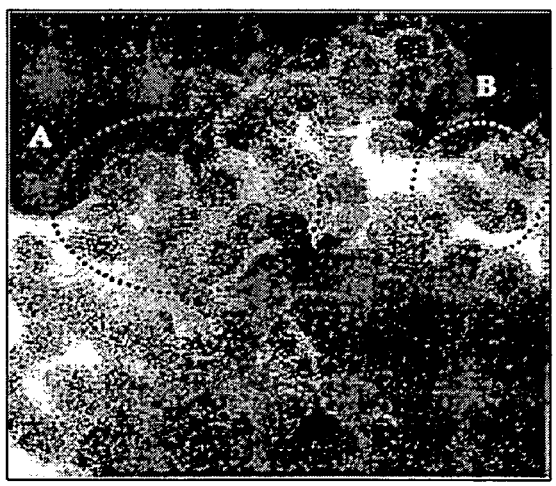

An exemplary zero-loss micrograph of the agglomerate of coated hydrophilic silica nanoparticles is shown in FIG. 12(a) and exemplary micrographs of silicon and carbon mapping are shown in FIGS. 12(b) and 12(c), respectively. When comparing the regions A and B in FIGS. 12(b) and 12(c), it is apparent that the carbon signal in the carbon mapping micrograph exactly outlines the configuration of the silica nanoparticles shown in the silicon mapping micrograph, and it appears that the hydrophilic silica nanoparticles were also completely encapsulated in a polymer matrix structure.

Figure 13:
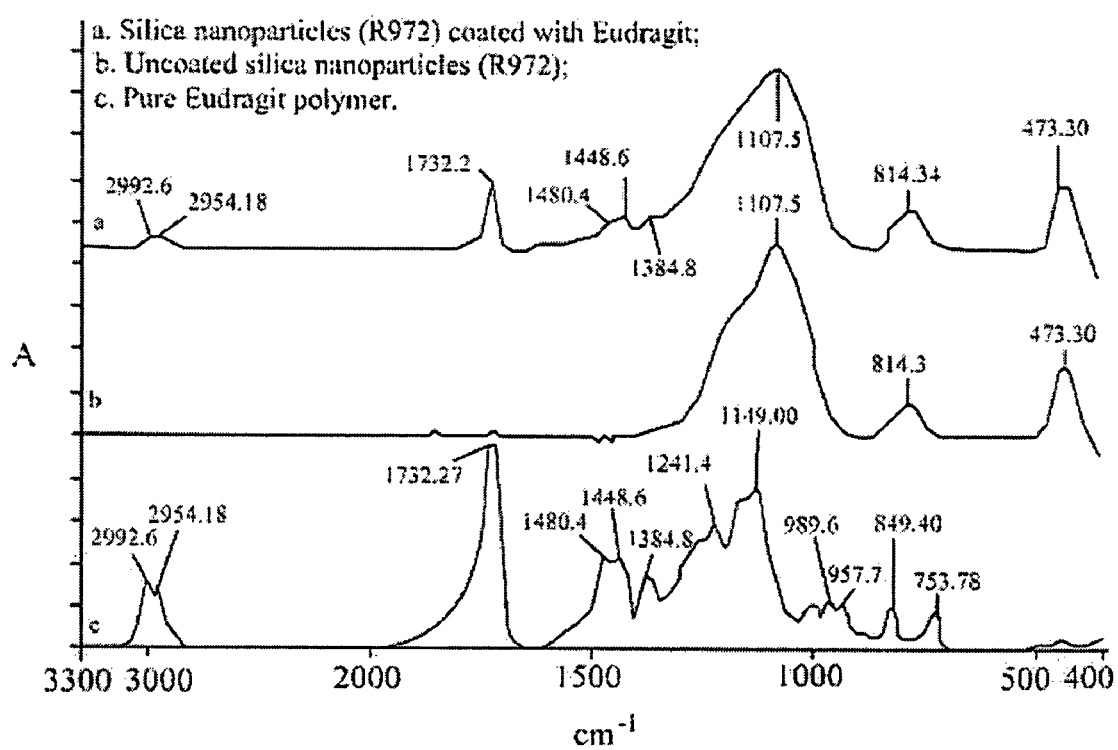
FIGS. 13(a)-13(c) are exemplary FT-IR spectra for hydrophilic silica nanoparticles, (a) representing coated nanoparticles, (b) representing uncoated nanoparticles, (c) representing Eudragit® copolymer.

The hydrophilic silica nanoparticles may also be tested using FT-IR, to identify any chemical changes after being coated with the polymer. FIG. 13 shows an exemplary spectra of uncoated silica nanoparticles, coated silica particles, and pure polymer powder, respectively. The results are practically the same as those found for the hydrophobic silica particles, again supporting the observations in the exemplary SEM and TEM micrographs (FIGS. 11(a)-(b) and FIGS. 12(a)-(b)) that the surface of the hydrophilic silica nanoparticles is preferably coated with polymer in a matrix structure.

The Degussa hydrophobic silica (Aerosil® R972) was manufactured by modifying the surface with dimethyldichlorosilane so that it exhibits a hydrophobic (water-repelling) property. It was surprising to find that the FT-IR spectra of the uncoated hydrophobic silica, FIG. 9(b), appears to be exactly the same as that of the uncoated hydrophilic silica, FIG. 13(b). The peaks from the methyl groups and from the C—Si bond were not observed in the FIG. 9(b). This is attributed to the very low concentration of methyl groups on the hydrophobic silica, which is below the detection limit of the Spectrum One FT-IR (0.1 wt. %). As observed in FIG. 9(a) and FIG. 13(a), the spectra of the coated hydrophobic and hydrophilic silica also appear to be the same. This result indicates that the SAS coating process of the present disclosure is preferably a purely physical deposition of precipitated polymer on the surface of particles and is therefore independent of the hydrophilicity or hydrophobicity of the surface of the silica nanoparticles.

However, the surface coverage of polymer on the hydrophobic silica particles appears to be somewhat less than that of the hydrophilic silica particles when comparing FIG. 8(c) to FIG. 12(c). This may be due to the fact that a somewhat larger polymer to silica ratio being used in the hydrophilic coating process.

Coating of 600 nm Silica Nanoparticles

Figure 14A:
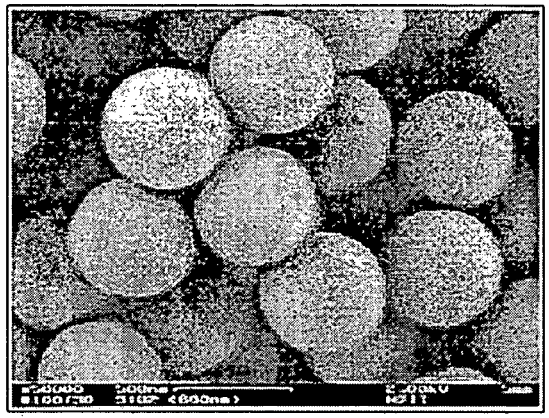
FIGS. 14(a)-14(d) are four exemplary SEM microphotographs, (a) representing uncoated 600 nm silica particles, (b) representing coated (polymer to silica, 1:4), (c) representing coated (with polymer to silica at a 1:5 ratio), (d) representing coated (with polymer to silica at a 1:6 ratio)
Figure 14C:
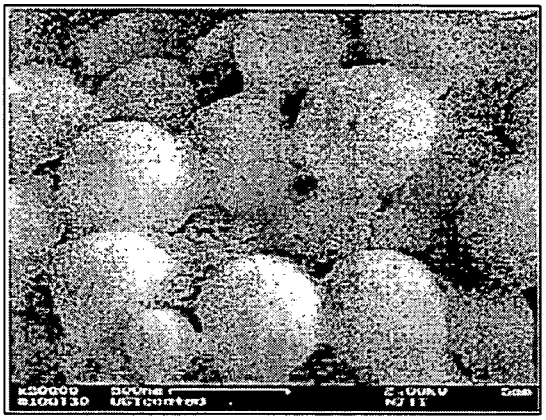
Figure 14B:
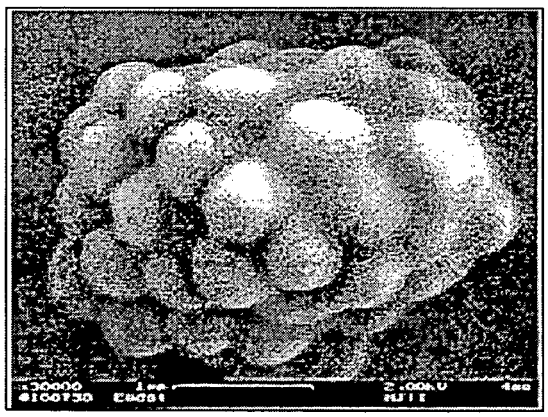
Figure 14D:
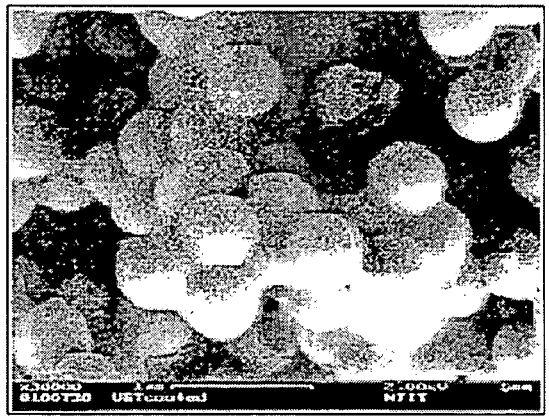

To further evaluate the SAS coating process of the present disclosure, a process to encapsulate 600 nm silica hydrophilic nanoparticles may be illustratively conducted. The exemplary SEM microphotograph in FIG. 14(a) shows the uncoated monodisperse spherical silica particles with a size of about 600 nm from the scale bar. After the SAS coating process of the present disclosure, it may be observed that silica particles were preferably coated with a polymer film on their surface, FIGS. 14(b)-14(d) for three exemplary weight ratios of polymer to silica investigated. When a ratio of polymer to nanoparticles (1:4 weight) is used, for example, a composite particle (agglomerate), containing many primary particles, of about 4 μm may be formed, FIG. 14(b). The formation of these large agglomerates may be due to the plasticization of the polymer by $CO_2$ [M. L. O'Neil, Q. Cao, M. Fang, K. P. Johnston, S. P. Wilkinson, C. Smith, J. L. Kerschner, S. H. Jureller, *Solubility of homopolymers and copolymers in carbon dioxide*, Ind. Eng. Chem. Res. 37 (1998) 3067] under high-pressure conditions since the glass transition temperature of the polymer is depressed by SC $CO_2$ [P. D. Condo, D. R. Paul, K. P. Johnston, *Glass transition of polymers with compressed fluid diluents: type II and III behavior*, Macromolecules 27 (1994) 365-371]. The agglomerates may also be formed when using a lower ratio of polymer to nanoparticles by weight, FIGS. 14(c) and 14(d). However, it appears that less agglomeration occurs when less polymer is used.

Figure 15:
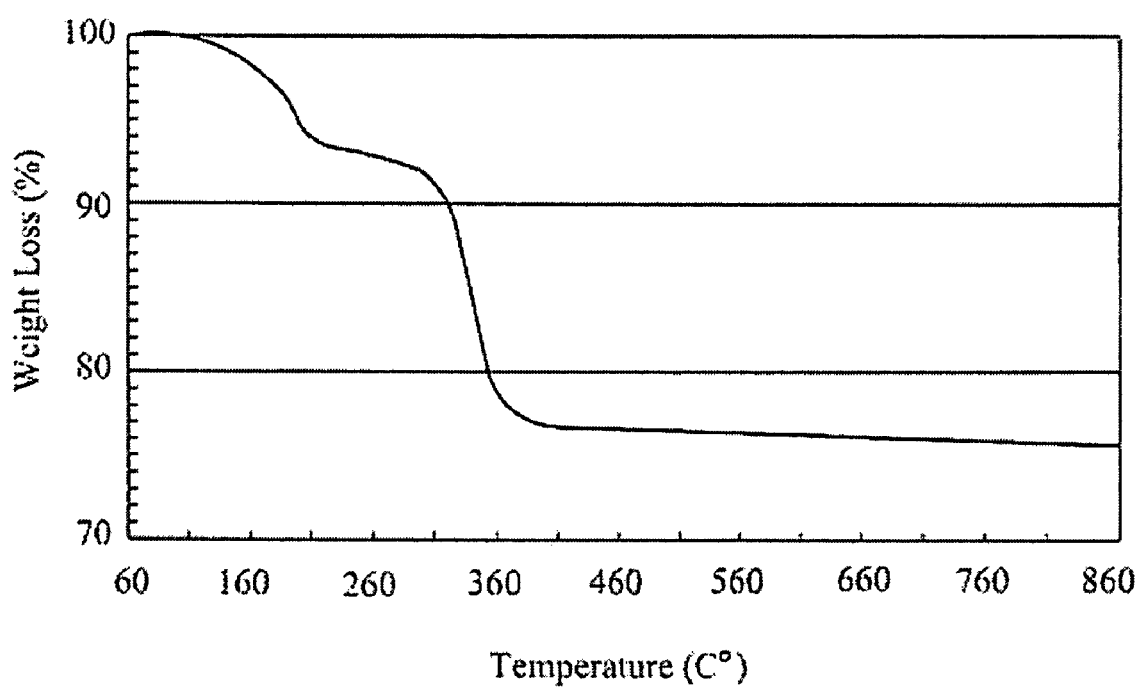
FIG. 15 is a chart of an exemplary TGA experiment to estimate the thickness of the coating layer on the surface of 600 nm silica particles coated with Eudragit® copolymer (1:4 ratio)

To estimate the thickness of the coating layer on the surface of the 600 nm particles the Eugragit coated nanoparticles (1:4 weight) may be heated in a Perkin Elmer thermo gravimetric analyzer (TGA), for example, to a temperature of 1073 K, which is preferably suitable to burn off the polymer coating. If it is assumed that the coating forms a spherical layer of constant thickness, h, then $$t = R(1 + \rho_H m_C / \rho_C m_H)^{1/3} - R \quad (1)$$

where R is the radius of the uncoated particle, $\rho_H$ and $\rho_C$ are the density of the host particles and polymer, and $m_H$ and $m_C$ are the weight of the host and polymer, respectively. From FIG. 15 and Eq. (1), h may be estimated to be 75 nm.

Having identified and described, by way of various examples, some of the preferred aspects of the present disclosure, it is noted that nanoparticle coating or encapsulation with a polymer using the SC $CO_2$ SAS coating process was investigated to reveal that 16-20 nm nanoparticles may be successfully coated or encapsulated in polymer by the SAS coating process. Further, the coating or encapsulation of nanoparticles using SC $CO_2$ SAS coating process appears to be independent of surface hydrophilicity. The mechanism of the SC $CO_2$ SAS coating process appears to be a heterogeneous polymer nucleation with nanoparticles serving as nuclei with a subsequent growth of polymer on the surface of the nanoparticles induced by mass transfer and phase transition. A polymer matrix structure of encapsulated nanoparticles was formed by agglomeration of the coated nanoparticles. For larger 600 nm particles the thickness of the polymer coating can be controlled by adjusting the ratio of polymer to host particles.

A TEM-EELS was found to be the best approach for the characterization of the coated nanoparticles since different elements can be detected at the nanoscale. FT-IR analysis is another valuable qualitative analysis method for material characterization. While silica has been given as an example of a material that may be coated as a nanoparticle, the similar procedures may be used to coat nanoparticle sized aluminum and magnesium powders for the purpose of passivating these materials for use as energetic materials.

If desired, a surfactant such as one that has an affinity for the supercritical fluid and for the polymer may be added. Fluoroalkyl acrylate homopolymers may be used. Active pharmaceuticals such as calcium channel blockers e.g. diltiazem, antihypertensives e.g. amlodipine, antidepressants e.g. amitryptline, anticholesterol agents, such as, for example, lovastatin and the like may be made into active nanoparticles that may be placed into gelatin capsules to prepare pharmaceutical dosage forms using the nanoparticles of the disclosure.

Controlled Drug Delivery System Applications

To further illustrate the efficiency and efficacy of the SC $CO_2$ SAS coating process in accordance with the present disclosure, application of the supercritical antisolvent coating process for controlled drug release design was experimentally demonstrated. Hydrocortisone as host particles and poly (lactide-co-glycolide) (PLGA) as polymer carrier were selected as an exemplary model system for this purpose. The drug particles were suspended in the polymer solution in dichloromethane. The suspension was then sprayed into supercritical $CO_2$ as an antisolvent. A parallel study of co-precipitation using the same supercritical antisolvent process running at the same conditions was performed for comparison. An SEM was used to characterize the drug particles before and after coating. The assay analysis was carried out using HPLC. The coated particles and co-precipitated particles were evaluated in terms of encapsulation efficiency and drug release profiles and it was found that higher polymer to drug ratio produced higher encapsulation efficiency. Indeed, at higher polymer to drug ratios, the coated drug particles demonstrated advantageous sustained release behavior.

As noted above, the incorporation of a pharmaceutical ingredient into a polymer carrier is of great interest for controlled drug delivery systems. Polymer based drug delivery carriers are desirable for many reasons. Each drug has a concentration range that provides optimal therapeutic effects. When the drug concentration falls out of this range, either higher or lower, it may cause toxic effects or become therapeutically ineffective. Therefore, it is desirable to release the drug content from a polymer carrier in a sustained or a controlled manner so as to eliminate the potential of either underdosing or overdosing. A polymer carrier can also provide protection for fragile drugs, such as proteins and peptides, from hydrolysis and degradation. For highly toxic drugs, a polymer carrier for target release is required to shield them until they are released at the target tissue. In addition, a drug controlled release system can improve patient compliance by reducing the drug administration frequency.

Polymer-based microsphere controlled drug release has attracted significant attention recently because of flexibility of administration. Microspheres less than 100 µm are suitable for intravenous injection. When the particle size is less than 5 µm, the microspheres can be administered via inhalation drug delivery. Submicron microspheres can even be injected directly into a circulation system. In controlled drug release, polymer-based microspheres usually have either a matrix or a microcapsule structure. In a matrix structure, the drug is uniformly dispersed in a polymer matrix whereas a microcapsule is generally composed of drug particles as core particles surrounded by a polymer coating film.

For both the matrix and the microcapsule structure, drug release occurs by one (or both) of two primary mechanisms: diffusion release or degradation release. Diffusion release takes place when an incorporated drug passes through the polymer pores or through polymer chains. This drug controlled release system can be designed by using a "smart polymer" having a permeability that is dependent on the environmental conditions, such as pH, temperature, and ionic strength, etc. (See, e.g., Dorski et al., "Preparation and characterization of glucose-sensitive P(MMA-g-EG) hydrogel", *Polym. Mater. Sci. Eng. Proceed.*, 76, 1997, 281-282). For example, pH is the stimulant for an acidic or basic hydrogel, and temperature is the stimulant for a thermoresponsive hydrogel (e.g., poly N-isopropylacrylamide). Degradation release occurs when a polymer degrades within the body as a result of natural biological processes, such as hydrolysis. In this type of controlled release system, the selection of the polymer is critical since the degradation is strongly dependent on the polymer's chemical structure and molecular weight. The most popular biodegradable polymers for drug controlled release systems include poly (lactic acid), poly (glycolic acid) and their copolymers [See, e.g., Brannon-Peppas, "Recent advances on the use of biodegradable microparticles and nanoparticles in the controlled drug delivery," *Intl. J Pharm.*, 11 6, 1995, 1-9].

According to the present disclosure, an advantageous antisolvent process for particle coating or encapsulation is disclosed for drug delivery applications. In the disclosed process, the host particles of interest are suspended in a coating polymer solution instead of being dissolved as in the co-precipitation process. The prepared suspension is either sprayed into a supercritical fluid, e.g., SC $CO_2$, or the supercritical fluid, e.g., SC $CO_2$, is injected into the suspension. As a result of the mutual diffusion between the SC $CO_2$ and the organic solvent, the polymer becomes supersaturated, is driven out of solution and deposits on the surface of the host particles, thereby producing a film coating. Thus, according to the present disclosure, an SAS process is employed to coat or encapsulate drug particles to achieve controlled drug release.

According to an exemplary embodiment of the disclosed method, drug particles less than 30 µm in size were used as hosts and a biopolymer of PLGA (poly lactice-co-glycolide at 50:50 ratio) was used as the coating polymer. The SAS process requires good miscibility of the solvent and SC $CO_2$. Once the polymer solution containing host particles in suspension contacts SC $CO_2$, very rapid mass transfer from the organic solvent to the bulk SC $CO_2$ (and vice versa) takes place so that a high degree of supersaturation is achieved. The polymer nucleates and precipitates out of solution and deposits on the surface of the host particles, and a film coating is generally formed if sufficient polymer is deposited on the surface of the host particles.

Figure 16:
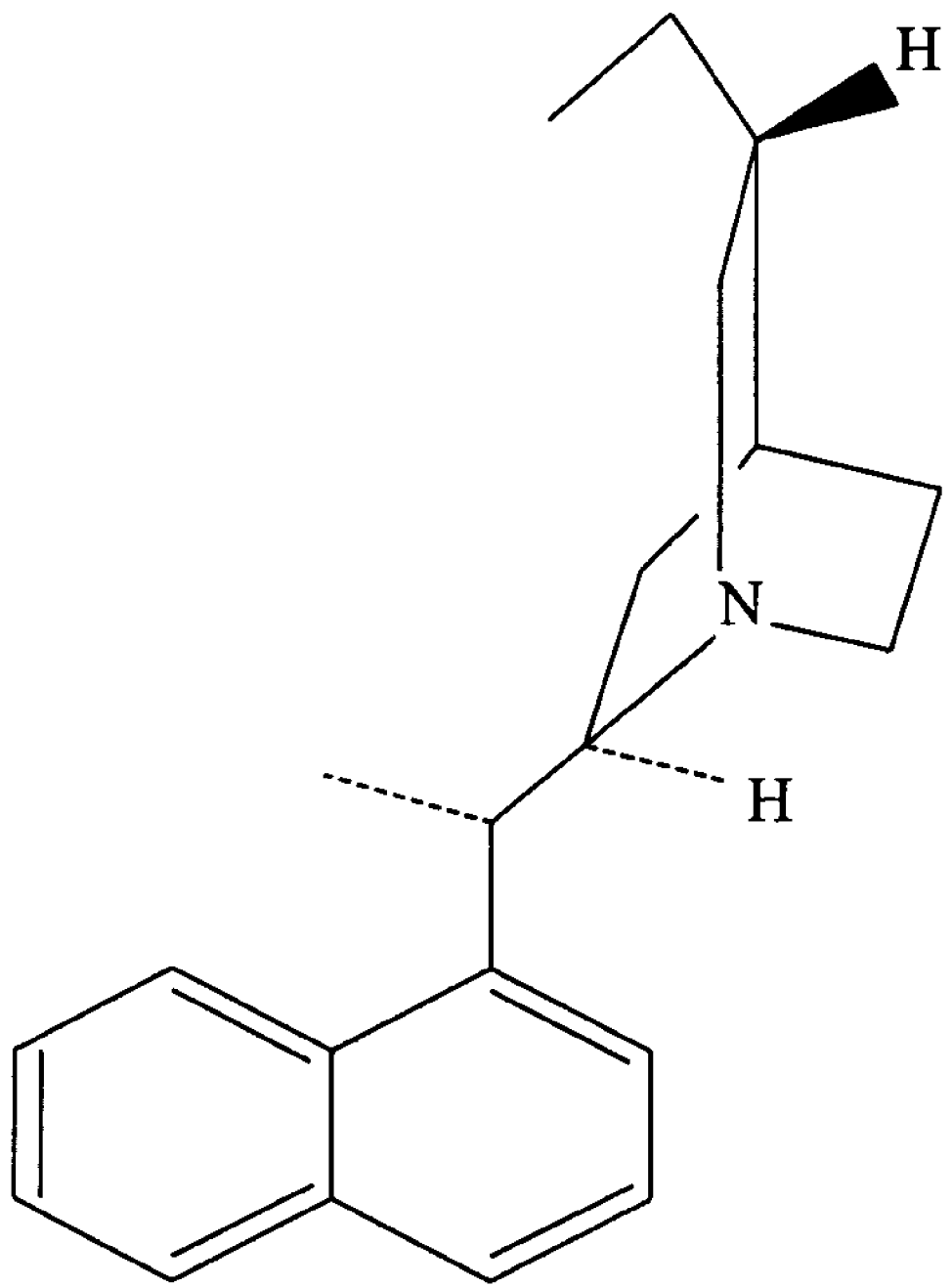
FIG. 16 is a schematic diagram of the chemical structure for hydrocortisone in accordance with an exemplary aspect of the present disclosure.

Thus, in an exemplary embodiment, the coating material was poly lactide-co-glycolide (PLGA) (Resomerg® 502, Boehringer Ingelheim Chemicals, Inc., USA, MW 12,000, 50/50, $T_g$ 40-550° C.). Acetone was purchased from Aldrich and used as received. Bone-dry liquid $CO_2$ was obtained from the Matheson Company, USA. Hydrocortisone (HC) (mean size less than 30 µm) was supplied by ICN Biomedical Inc., USA. It was used as received without further treatment. The molecular structure of hydrocortisone is shown in FIG. 16. An exemplary system for hydrocortisone processing is schematically shown in FIG. 2 hereto and generally described above. Thus, the processing system generally consists of three major systems: a suspension delivery system, a $CO_2$ supply system, and a stainless steel high pressure chamber with a volume of 1000 ml (Parr Instruments, USA).

A water bath is used to keep the temperature at a desired value. A metering valve (Swagelok, SS-31RS4, R.S. Crum & Company, USA) was utilized to control the system pressure (the $CO_2$ inlet and outlet) and a pressure gauge was located on the lid of the high pressure chamber. A capillary nozzle (254 µm ID) is used to spray the suspension into the high pressure chamber and a metering pump (Model EL-1A, American Lewa®, USA) is used to deliver liquid $CO_2$ into the chamber from a $CO_2$ cylinder. The liquid $CO_2$ is chilled to around 0° C. by a refrigerator (Neslab, RTE-111) to avoid cavitation. A heating tape (Berstead Thermolyne, BIH 171-100) is used to preheat the liquid $CO_2$ before it enters into the high-pressure chamber.

An exemplary processing protocol according to the present disclosure is as follows. The precipitation chamber is first charged with SC $CO_2$. After the predetermined operating conditions (temperature and pressure) are reached, a steady flow of $CO_2$ is established by adjusting the metering valve and the metering pump. The flow rate of $CO_2$ was usually less than 3.0 standard liters per minute (SLPM). PLGA and hydrocortisone (HC) are then weighed and mixed into dichloromethane (DCM) to produce a suspension with the desired polymer concentration and PLGA to HC ratio. The suspension-so-produced is then injected at a flow rate of 0.8 ml/min into the high pressure chamber through the capillary nozzle by using an HPLC pump (Beckman, 110B) for about 10 minutes. After spraying, fresh $CO_2$ is supplied continuously to purge the chamber with about 1 equivalent volume of $CO_2$ in order to remove any remaining dichloromethane. After purging, the precipitation chamber is slowly depressurized and the coated drug particles collected for characterization.

In addition, a parallel study of co-precipitation of hydrocortisone and PLGA was performed for comparison purposes. In the co-precipitation experiment, PLGA and hydrocortisone are dissolved in either acetone or a mixture of methanol and dichloromethane (volume ratio of 1:1) to make a homogeneous solution. The solution is then sprayed into the high-pressure chamber at the same operating conditions as was used in the SAS coating process described above. The operating conditions of the SAS coating and co-precipitation processes are set forth in FIG. 17.

Field emission scanning electron microscopy (FE-SEM) (Leo, 1530VP) was used to observe any morphological changes before and after the coating treatment. The samples were spread on carbon tape for observation under SEM. HPLC assay analysis of hydrocortisone was performed using a Hewlett Packard 1100 equipped with a reverse phase C-18 column (Microsorb-MV 100, 150×4.6 mm, 5 µm, Varian). The mobile phase was made at a composition of acetonitrile and purified water (40:60, v/v) and the injection volume was 10 µl. The flow rate was 1.0 ml/min and hydrocortisone was detected at 242 nm by a UV detector. The run time for the assay was 4.0 minutes and the retention time for hydrocortisone was 2.9 minutes.

Based on the foregoing experimental work, a determination of encapsulation efficiency was possible. A known amount of coated drug samples was washed with ethanol, which is a good solvent for hydrocortisone but a poor solvent for PLGA, to dissolve the uncoated or partially coated drug particles. The suspension was centrifuged at 1500 rpm for 5 minutes. The supernatant fluid was sampled to determine the un-encapsulated drug content using HPLC. The sediment was then dissolved with a mixture of acetone and ethanol (50:50) and the drug content was determined using HPLC assay analysis. Each sample was analyzed in triplicate. The encapsulation efficiency (EE) was calculated using the following equation:

$$\% \, EE = \frac{\text{encapsulated drug}}{\text{unencapsulated drug} + \text{encapsulated drug}} \times 100\%$$

In vitro drug release tests were also conducted. The coated or encapsulated drug was weighed and put into a test tube along with 30 ml of pH buffer solution (PBS, pH 7.4) with 0.05% Brij 58. A small magnetic stirrer bar was used to improve the mixing. All samples were incubated at 37° C. while being agitated. At given time intervals the test tubes were centrifuged at 1500 rpm for 5 minutes and 200 µl of supernatant fluid was transferred into small vials for HPLC assay analysis. The removed supernatant was replaced with the same volume of fresh PBS. Dissolution tests of each sample were performed in three replicates. The results associated with the disclosed process for drug encapsulation (as exemplified in the processing of hydrocortisone) are readily discussed below.

Figure 18A:
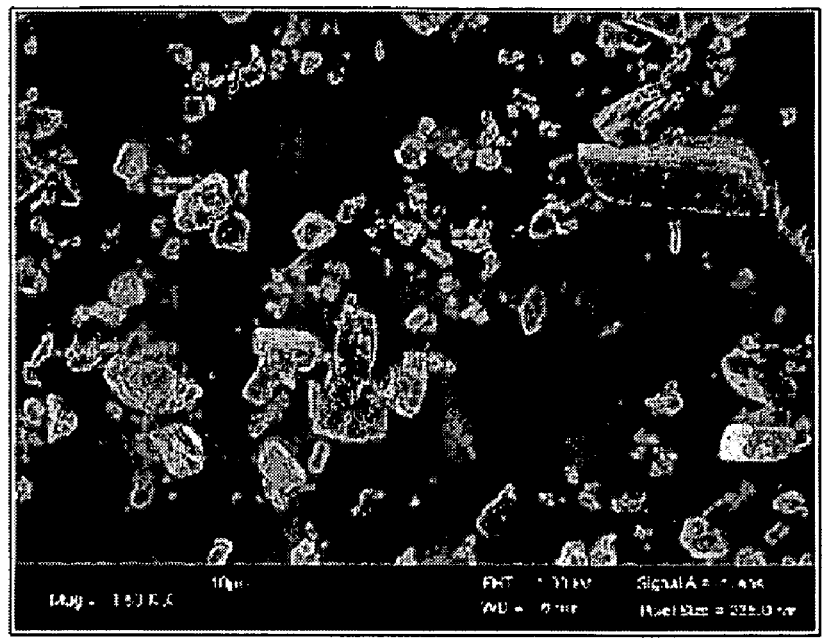
FIGS. 18(a) and 18(b) are exemplary scanning electron microscope (SEM) micrographs of uncoated hydrocortisone particles, (a) ×1500, (b) ×2940.
Figure 18B:
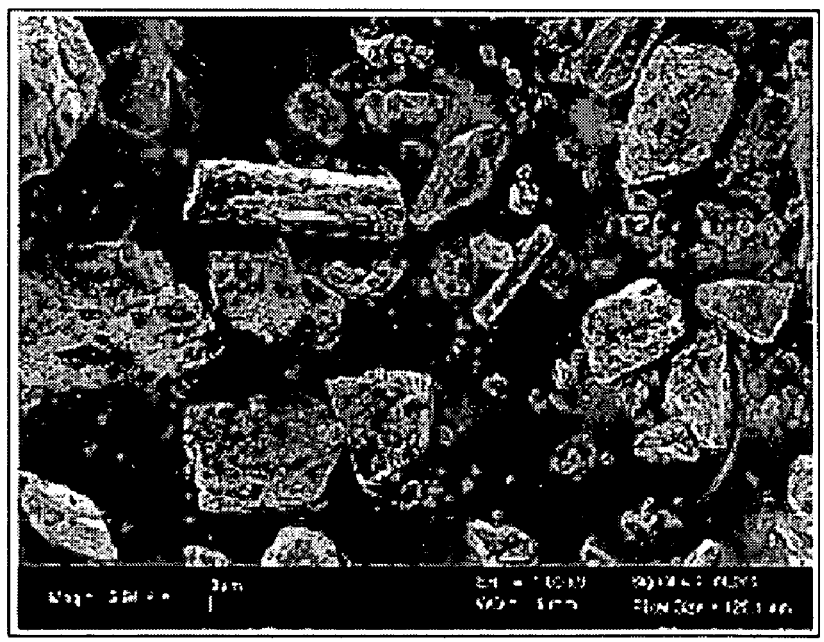
Figure 19A:
FIGS. 19(a) and 19(b) are exemplary scanning SEM micrographs of processed hydrocortisone particles at a polymer to particle ratio of 1:4, (a) ×5210, (b) ×10,000.
Figure 19B:
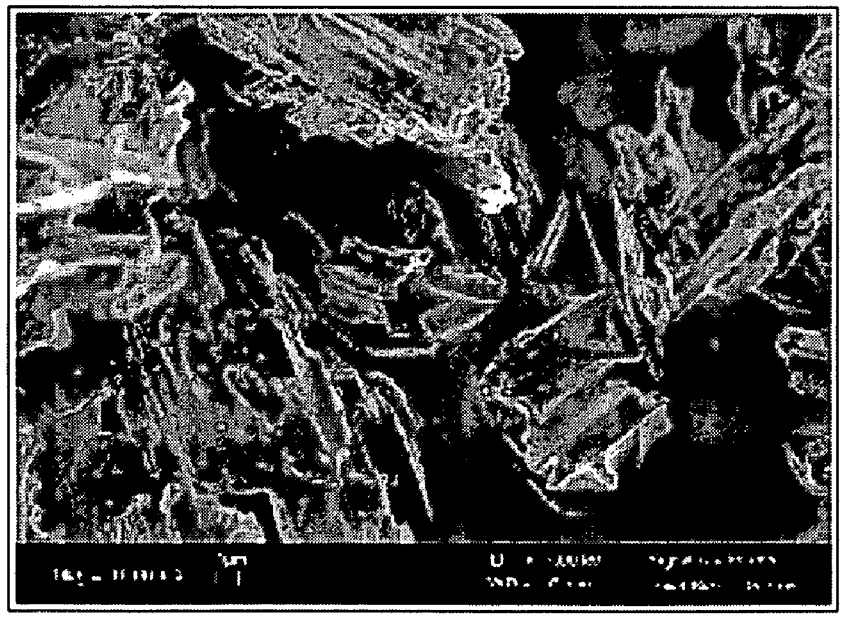

Initially, reference is made to FIG. 18 wherein SEM images of the untreated hydrocortisone particles employed in the experimental studies are shown. Hydrocortisone is seen to be in crystal form with defined facets and sharp edges. The average particle size is less than 30 µm as seen from the scale bar. The coated hydrocortisone particles, at a polymer to hydrocortisone weight ratio of 1:4, are shown in FIG. 19. The coated particles have a different shape (morphology) and no clear sharp edges when compared with the uncoated drug particles. This indicates that some of the drug particles were partially coated with polymer during the SAS process but no film coating or encapsulation seemed to have occurred. The difference in shape between the coated and uncoated drug particles may be attributed to the fact that some hydrocortisone (about 17% of the total) dissolved in DCM, although DCM is not a good solvent for hydrocortisone. The dissolved drug may undergo nucleation and re-crystallization during the SAS process. Therefore, the re-crystallized drug particles formed during the SAS process may have a different shape than the original particles.

Figure 20A:
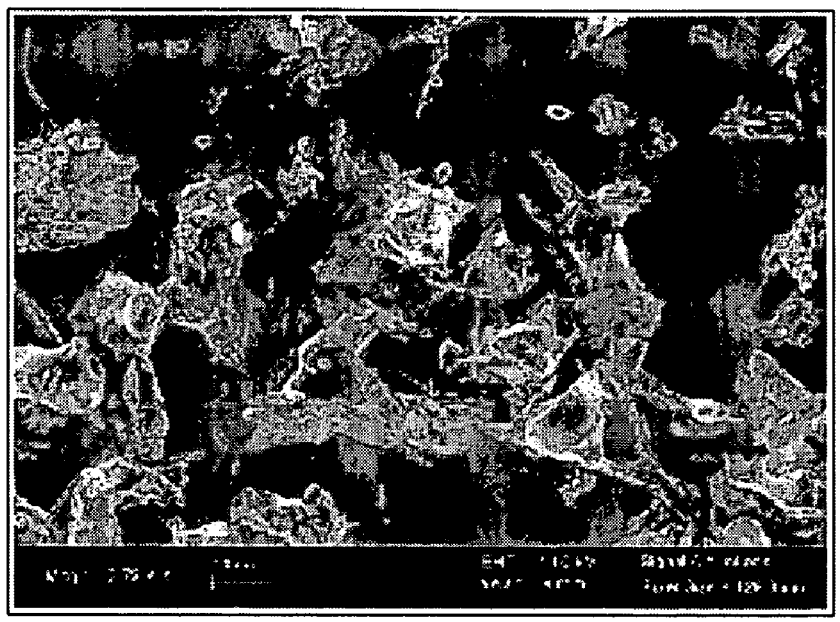
FIGS. 20(a) and 20(b) are exemplary scanning SEM micrographs of coated hydrocortisone particles at a polymer to particle ratio of 1:2, (a)×2730, (b)×10,610.
Figure 20B:
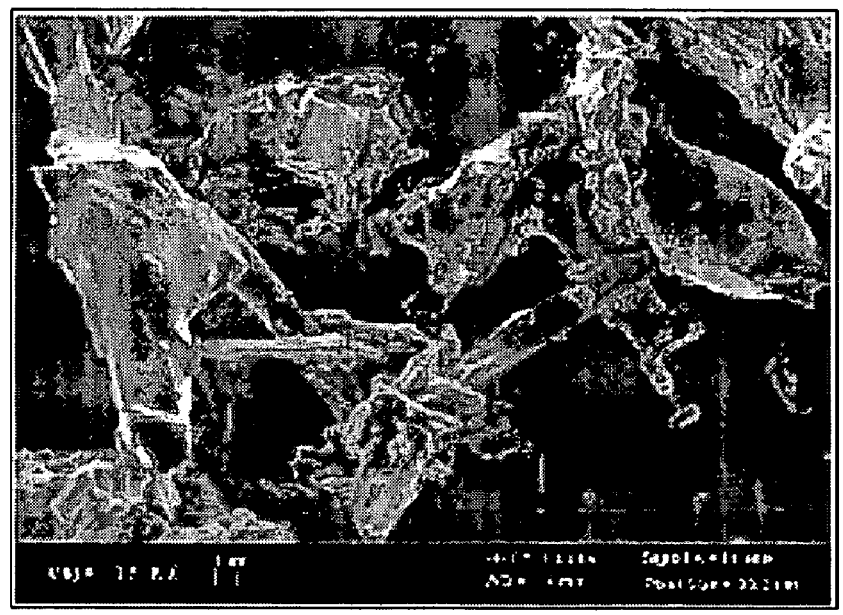

When the polymer to drug ratio was increased to 1:2, more polymer precipitated out and deposited on the surface of the drug particles, as seen in FIG. 20. The smaller drug particles seemed to be embedded or entrapped in the coating polymer. However, the larger drug particles appeared to have been left uncoated, indicating that large, irregular shaped particles may require even more polymer to encapsulate them.

Figure 21A:
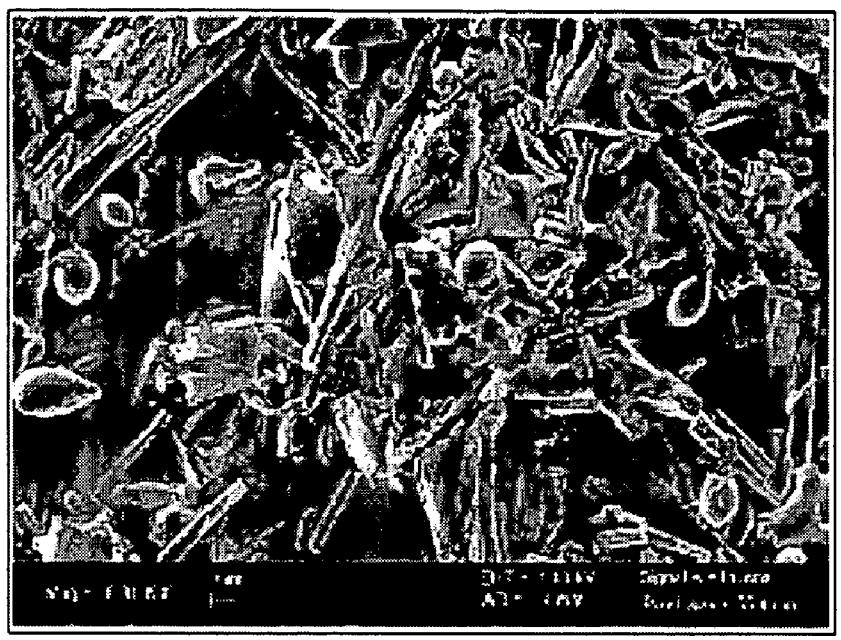
FIGS. 21(a) and 21(b) are exemplary scanning SEM micrographs of coated hydrocortisone particles at a polymer to particle ratio of 1:1, (a) ×6310, (b) ×9630.
Figure 21B:

In order to encapsulate the larger particles, the polymer loading was increased to a polymer to drug ratio of 1:1. SEM images of the coated drug particles at the 1:1 ratio are shown in FIG. 21. As observed in FIG. 21, more polymer coating took place on the surface of the drug particles as compared with drug particles coated at a 1:4 ratio (FIG. 19) and a 1:2 ratio (FIG. 20). Some of the smaller drug particles were even encapsulated in polymer microspheres. However, it was found that the polymer coating on the surface of the drug particles was still unevenly distributed due to the irregularity of the drug particles. Thus, it appears that uniformly coating or encapsulating irregular particles by SAS presents a major challenge.

A parallel study was performed to compare drug particle coating and co-precipitation using the SAS process. In the co-precipitation experiments, hydrocortisone and PLGA were dissolved in acetone or a mixture of methanol and DCM. A clear solution instead of a suspension was sprayed into SC $CO_2$ in the SAS process.

Figure 22A:
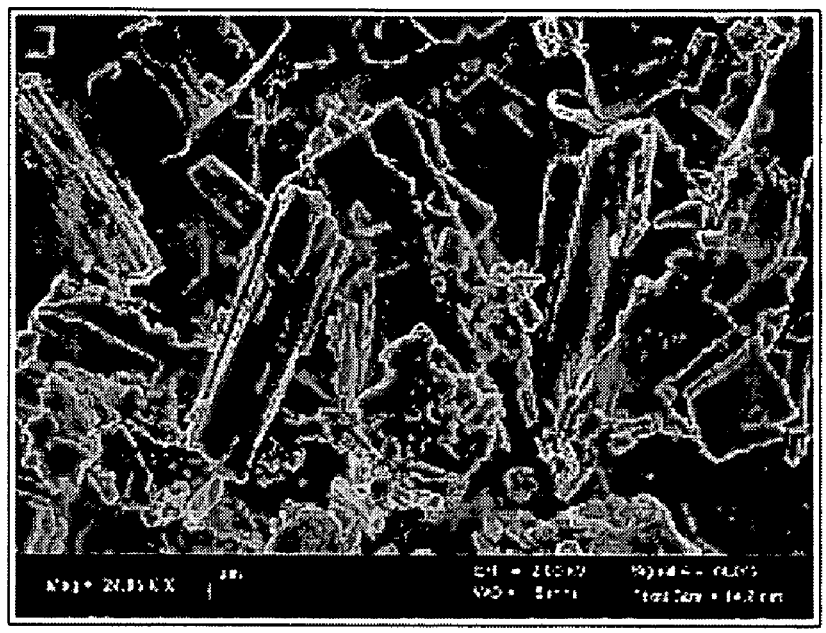
FIGS. 22(a) and 22(b) are exemplary scanning SEM micrographs of co-precipitated hydrocortisone particles at a polymer to drug ratio of 1:1, (a) methanol and DCM mixture; ×24,850, (b) acetone; ×25,990.
Figure 22B:
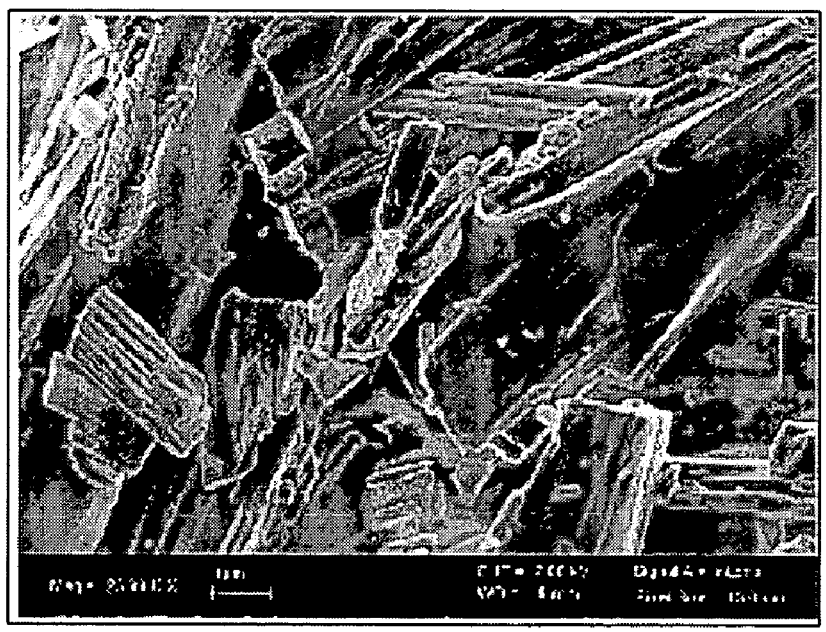

SEM photographs of the co-precipitated particles of drug and polymer in FIG. 22 clearly show that the co-precipitated particles have a very different morphology and shape from the original particles. The re-crystallized drug particles have defined facets and the polymer appeared to be simply attached to (rather than coating) the surface of the re-crystallized drug particles. It was apparent that there was a phase separation during the precipitation of polymer and drug from the acetone or DCM/methanol solutions. Therefore, it appears that no coating or encapsulation occurred in the SAS co-precipitation process.

The coated drug particles and co-precipitated drugs were analyzed to determine the encapsulation efficiency. The results are listed in the table of FIG. 23. The coated drug particles at a polymer to drug ratio of 1:4 showed that drug particles were not encapsulated within the polymer. This supported the conclusion that the drug particles were only partially coated by polymer as shown in FIG. 19. In the encapsulation efficiency test, if an uncoated part of the surface of a drug particle is exposed to ethanol, the whole drug particle would be dissolved gradually. Therefore, partially coated drug particles did not show any encapsulation efficiency. When the polymer loading was increased to a ratio of 1:2, more polymer coating occurred on the surface of drug particles and the average encapsulation efficiency increased to 6.7%. When more polymer was used, the smaller drug particles were probably completely encapsulated by the polymer. Consequently, these encapsulated drug particles were not washed away by ethanol in the encapsulation efficiency test and they contributed to the encapsulation efficiency. However, the encapsulation rate was not improved considerably even though the polymer loading was doubled. This was probably due to the fact that the larger, irregular-shaped drug particles left some sharp edges or corners uncoated and therefore were completely dissolved by the ethanol treatment.

When the polymer to particle ratio was further raised to 1:1, more drug particles were encapsulated and the encapsulation efficiency increased to 22.6%. This supported the observation in FIG. 21 that more of the drug particles were completely encapsulated or trapped in polymer microspheres. This suggests that the encapsulation efficiency could be further improved by either increasing the amount of polymer or reducing the size of host particles.

The co-precipitated drug and polymer particles from either acetone or methanol/DCM mixture showed no encapsulation of drug particles even at a polymer to drug ratio of 1:1. This is in good agreement with what was observed in FIG. 22 that the re-crystallized drug was not encapsulated with polymer and that the polymer was simply attached on the surface of the drug particles.

Figure 24:
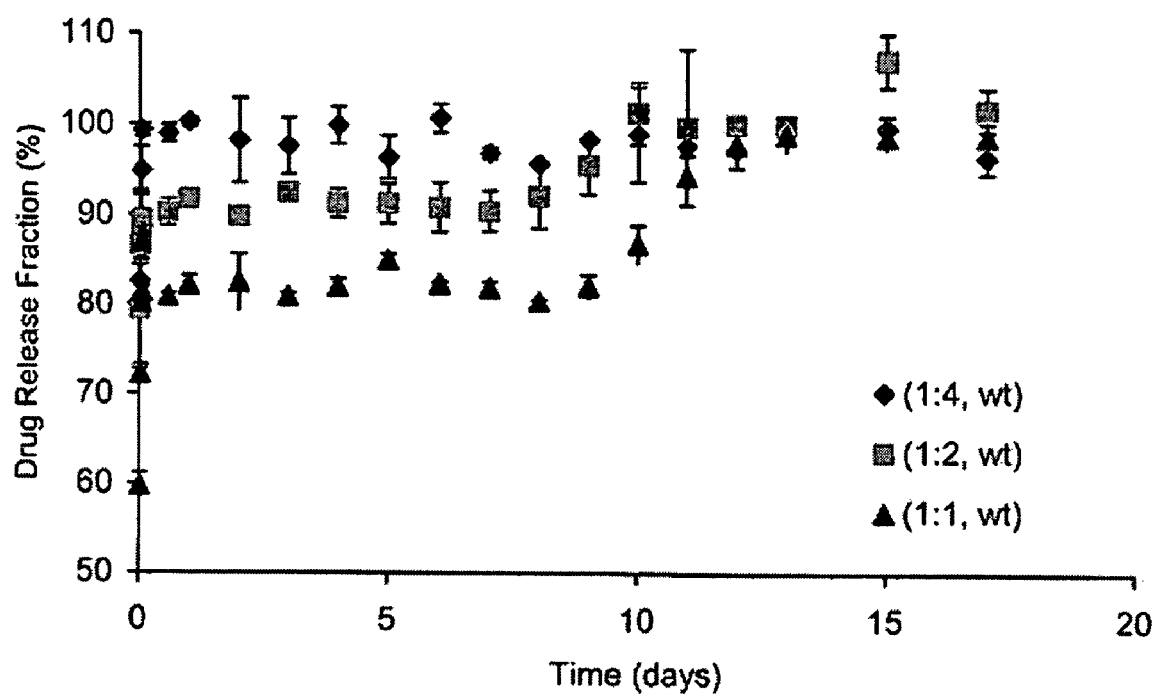
FIG. 24 is a plot of overall hydrocortisone release profiles of coated drug particles at different polymer to drug ratios according to exemplary implementations of the present disclosure.

As noted above, in vitro drug release tests were carried out to determine the release behavior of coated drug particles at different polymer to drug ratios. The release profiles are plotted in FIG. 24. The drug particles coated at a 1:4 ratio showed a fast release behavior; almost all of the drug content was released in about 1.5 hours. This rapid release rate was attributed to the fast dissolution of the drug particles. The release behavior confirmed the encapsulation test results for the coated particles at a 1:4 polymer to drug ratio, i.e., that no drug particles were entirely encapsulated.

The coated particles at a 1:2 ratio showed an initial release of about 90% of the drug content in about 1.5 hours. As further shown in FIG. 24, after the initial burst, a second phase of much slower drug release occurred. At day 9, the PLGA started to degrade and the rest of the encapsulated drug was released in about 1 day. This behavior suggests that about 10% of the drug particles were completely encapsulated, which is close to the encapsulation efficiency test result. The uncoated or partially coated drug particles were quickly dissolved in the release medium and this accounted for the burst release.

The drug particles coated at a 1:1 ratio showed a lower amount of fast release of drug than those coated at the 1:2 ratio. About 80% of drug was released during this phase. After this initial burst stage, a period of much slower drug release occurred before the onset of the polymer degradation stage. In about 9 days, PLGA started to degrade and the encapsulated drug was continuously released for about 3 days. This release behavior again supported the results of the encapsulation efficiency test on the coated drug particles at a 1:1 ratio. The sigmoidal release profile exhibited by the drug particles coated at a 1:1 polymer to drug ratio was typical of polymer degradation controlled drug release [See, e.g., Gallagher et al., "Gas anti-solvent recrystallization of RDX: Formation of ultrafine particles of a difficult-to-comminute explosive," *J. Supercrit. Fluids*, 5, 1992, 130-142.] By increasing the amount of polymer used for coating or reducing the size of the drug particles, a larger fraction of drug particles would be incorporated into polymer microspheres. Thus, the initial burst release would be reduced and the release of drug would last longer.

Figure 25:
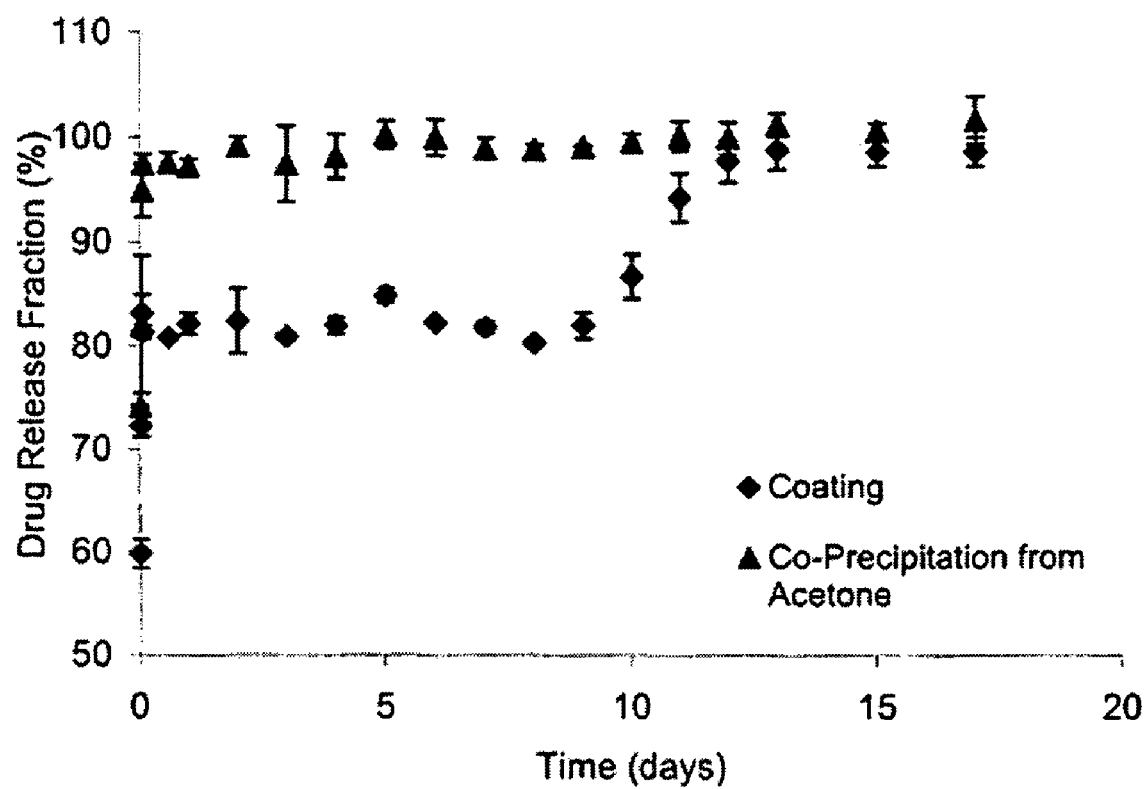
FIG. 25 is a plot of overall hydrocortisone release profiles of coated drug particles and co-precipitated drug and PLGA from acetone.

To compare the SAS coating and co-precipitation processes, a drug release test of the co-precipitated sample from acetone was performed following the same procedure. The release profile is shown in FIG. 25. It is clear from plot of FIG. 25 that the re-crystallized drug and PLGA from the co-precipitation process exhibited a very fast release of the drug throughout the entire duration of the test. This suggests that no encapsulation occurred during the co-precipitation of drug and PLGA, even at a polymer to drug ratio of 1:1. This release test result confirmed the encapsulation test result.

Based on the foregoing test results, it is apparent that hydrocortisone particles were shown to be successfully coated with PLGA in the SAS coating process of the present disclosure. At a low 1:4 polymer to drug weight ratio, the drug surface was only partially coated and no encapsulation (encapsulation efficiency of zero) occurred. The encapsulation efficiency improved with an increase in polymer to drug ratio, increasing to 22.6% when the polymer to drug ratio was 1:1. At polymer to drug ratios of 1:2 and 1:1, the coated drug particles exhibited an advantageous sustained release behavior. By comparison, co-precipitations of drug and polymer (both in solution) failed to achieve encapsulation; rather, the polymer appeared to be simply attached in chunks on to the surface of the drug particles.

Although the encapsulation efficiency achieved was relatively low in the experimental studies described herein and an initial burst stage was observed, sustained drug release was achieved according to the present disclosure and could likely be further improved by increasing the polymer loading or reducing the size of the drug particles because smaller particles have a greater chance to be encapsulated or entrapped. Indeed, based on the test results and analysis set forth herein, it is readily apparent that desired levels of coating/encapsulation efficiency may be achieved using the disclosed system and process, e.g., through control and/or manipulation of processing parameters and material properties in the manner described and/or suggested. Thus, the disclosed SAS coating process is an advantageous technique for the design of drug delivery systems and may offer particularly advantageous utility for inhalation drugs where the particle size cannot be larger than a few microns.

Process Parameter Evaluation and Optimization

Additional studies have been conducted to investigate the effects of various process parameters, such as the polymer weight fraction, polymer concentration, temperature, pressure, and flow rate, on the coating of particles and the agglomeration of the coated particles in the SAS coating process of the present disclosure. The potential effect of $CO_2$-soluble surfactants was also evaluated to determine whether such surfactants are effective in reducing and/or minimizing agglomeration. Based on these additional studies, enhanced and/or optimized processing of nanoparticles and other ultrafine particles is facilitated. These additional studies also permit an attempt at proposing a mechanism for the SAS coating process of the present disclosure.

1. Materials

The exemplary host particles that were used-in this additional SAS coating study were spherical silica particles with size of approximately 0.5 μm which were synthesized using the classic StÖber process [See, StÖber et al., *Controlled Growth of Monodisperse Silica Spheres in the Micron Size Range*, J. Colloid & Interface Sci. 26 (1968) 62-69.]. Tetraethyl orthosilicate (TEOS) (MW 208, 98 %) was purchased from Sigma-Aldrirch Colo., USA. Ammonia hydroxide (28.87 %) was purchased from Fisher Scientific, USA, and anhydrous ethyl alcohol from Aaper Alcohol, USA. Each of the foregoing chemicals was used without further treatment.

Figure 26:
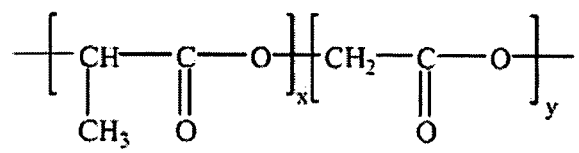
FIG. 26 includes schematic diagrams of the chemical structures for compounds utilized in exemplary embodiments of the present disclosure.
Figure 26:
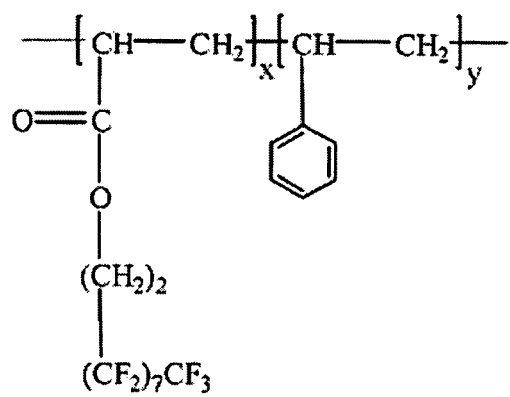
Figure 26:
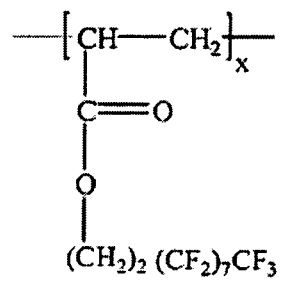
Figure 26:
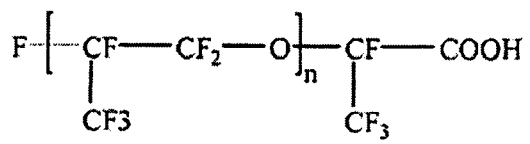

The coating material was poly lactide-co-glycolide (PLGA) (Resomer® 502, MW 12,000, 50/50, $T_g$ 40-55° C.) and was supplied from Boehringer Ingelheim Chemicals, Inc., USA. Acetone was purchased from Aldrich (Milwaukee, Wis.) and used as received. Liquid $CO_2$ was obtained from the Matheson Company, USA. Surfactants of random poly (fluoroalkylacrylate-styrene) (PFS) (29 mol % styrene) and poly (fluoroacrylate) homopolymer (PFA) were synthesized at the University of Pittsburgh. The surfactant Krytox 157 FSL, a perfluoropolyether terminated with a carboxylic acid at one end (i.e., a monofunctional perfluoropolyether carboxylic acid) was supplied by DuPont Chemicals (Deepwater, N.J.). These surfactants were used as received without further treatment. The chemical structures of the coating polymer and the surfactants are schematically depicted in FIG. 26 hereto.

2. Methods

In the preparation of spherical silica particles, pure alcohol, ammonia hydroxide, and deionized water were mixed in an Erlenmeyer flask at pre-determined concentrations. TEOS was then added into the mixture that was stirred by a magnetic bar. TEOS underwent hydrolysis in water and grew into spherical silica particles, with ammonia acting as a morphological catalyst. After 24 hours of reaction, the solution turned into a milky suspension. The resulting suspension was centrifuged at 3000 rpm for 5 minutes. The supernatant liquid was then drained and the particulate sediment was re-dispersed in pure alcohol. This washing step was employed to remove unreacted TEOS and water, and was repeated twice. Finally, the sediment of silica particles was re-dispersed in acetone to produce a suspension for further use in the SAS coating procedures described below.

FIG. 2 is a schematic diagram of the system used to process particles, and as described previously, consists of three major components: a suspension delivery system, a $CO_2$ supply system, and a stainless steel precipitation chamber equipped with a pressure gauge (Parr Instruments, USA). The precipitation chamber has a volume of 1000 ml. Its temperature was kept at the desired value using a water bath. The stainless steel capillary nozzle used to atomize the suspension, the $CO_2$ inlet, and the $CO_2$ outlet were all located on the lid of the precipitation chamber. The system pressure was controlled by a downstream metering valve (Swagelok, SS-31RS4, R.S. Crum & Company, USA) and was monitored by a pressure gauge. Liquid $CO_2$ was supplied from a $CO_2$ cylinder by a metering pump (Model EL-1A, American Lewa®, USA). A refrigerator (Neslab, RTE-111) was used to chill the liquefied $CO_2$ to around 0° C. to avoid cavitation. The temperature of the liquefied $CO_2$ was then raised using a heating tape (Berstead Thermolyne, BIH 171-100).

According to an exemplary process of the present disclosure, the precipitation chamber was first charged with SC $CO_2$. When the desired operating conditions (temperature and pressure) were reached, a steady flow of $CO_2$ was established by adjusting the metering valve and the metering pump. The flow rate of $CO_2$ ranged from 1.0 to 5.0 standard liters per minute (SLPM). The coating material, PLGA, was then weighed and dissolved into the acetone-silica suspension to produce the desired polymer concentration and polymer to silica ratio. The prepared suspension was delivered into the precipitation chamber through a capillary nozzle (ID 254 μm) using an HPLC pump (Beckman, 110B) for about 15 minutes. The flow rate varied from 0.4 to 1.3 ml/min.

After spraying, fresh $CO_2$ continued to flush the chamber in order to get rid of residual organic solvent. The temperature and pressure were maintained unchanged during this washing step, which was employed to prevent any condensed organic solvent due to phase separation between the organic solvent and SC $CO_2$ from redissolving the polymer on the surface of particles during depressurization. The washing step lasted about 3 hours, with variations depending on the process conditions. After the washing process, the precipitation chamber was slowly depressurized and the coated particles were harvested for characterization. The experimental operating conditions for these processing runs that did not include a surfactant are listed in the table set forth in FIG. 27 hereto.

In a second set of SAS coating runs, a surfactant was added to the system. In this second set, a predetermined amount of surfactant was charged into the precipitation chamber before the process was commenced. Once the desired processing conditions were achieved, the magnetic stirrer was turned on (600 rpm) to assist in the dissolution of the surfactant in SC $CO_2$. Thereafter, the procedure followed the sequence of steps described above with respect to the non-surfactant runs. The operating conditions for the SAS coating experiments that included surfactants are set froth in FIG. 28 hereto.

3. Characterization

The silica particles were photographed using a field emission scanning electron microscope (FE-SEM) (Leo, JSM-6700F) to observe any morphological changes before and after the coating treatment. The samples were either spread on a carbon tape or on an aluminum stub support device after dispersing in alcohol and evaporating. Particle size (PS) and particle size distribution (PSD) were analyzed using a LS Particle Size Analyzer (Beckman Coulter). Before particle size analysis, the coated and uncoated particles were dispersed in ethyl alcohol, in which the PLGA was not dissolved, and the resulting suspension was sonicated for 3 minutes. The sonicated suspension was then added into the Beckman Coulter sample cell one drop at a time.

4. Results and Discussion

According to the present disclosure, the solubility of the solute and solvent in SC $CO_2$ are important considerations in the efficiency and efficacy of the disclosed process. Successful applications of the disclosed process benefit from good miscibility of the solvent and the SC $CO_2$, with the solute having negligible solubility in the SC $CO_2$. There is also a volumetric expansion when $CO_2$ is dissolved in the solvent, which is important for precipitation of the solute.

The volumetric expansion $\Delta V \%$ may be defined as:

$$\Delta V\% = \frac{V(P, T) - V_0}{V_0} \times 100\% \quad (2)$$

where $V(P, T)$ is the volume of solvent expanded by $CO_2$ and $V_0$ is the volume of pure solvent.

Acetone was used as the solvent and PLGA as the solute in the exemplary processing runs described herein. The Peng-Robinson equation of state (PREoS) can be used to predict the expansion behavior of the binary system of $CO_2$-acetone. The PREoS can be written as:

$$P = \frac{RT}{v-b} - \frac{a(T)}{v(v+b) + b(v-b)} \quad (3)$$

where "a" and "b" are parameters of the mixture in the binary system.

Originally, the PREoS had only one interaction coefficient, $k_{ij}$. However, as suggested by Kordikowski, it is necessary to have a second interaction parameter $l_{ij}$ to account for a polar compound in the binary system. In the presently disclosed system, $k_{ij}$ is −0.007 and $l_{ij}$ is −0.002, which are regressed from reported experimental data. The mixing rules are given as:

$$a = \sum_i \sum_j x_i x_j a_{ij} \quad (4)$$

$$b = \sum_i x_i x_j b_{ij} \quad (5)$$

$$a_{ij} = (1 - k_{ij})\sqrt{a_i a_j} \quad (6)$$

$$b_{ij} = \frac{(b_i + b_j)}{2}(1 - l_{ij}) \quad (7)$$

where the pure component values can be determined as:

$$b_{ii} = 0.07780 \frac{RT_{ci}}{P_{ci}} \quad (8)$$

$$a = 0.45724 \quad (9)$$
$$\frac{R^2 T_{ci}^2}{P}\left[1 + (0.37464 + 1.54226\omega_i - 0.26992\omega_i^2) \times \left(1 - \sqrt{\frac{T}{T_{ci}}}\right)\right]^2$$

and $P_{ci}$, $T_{ci}$, and $\omega_i$ are the critical pressure, critical temperature, and accentric, respectively.

Figure 29:
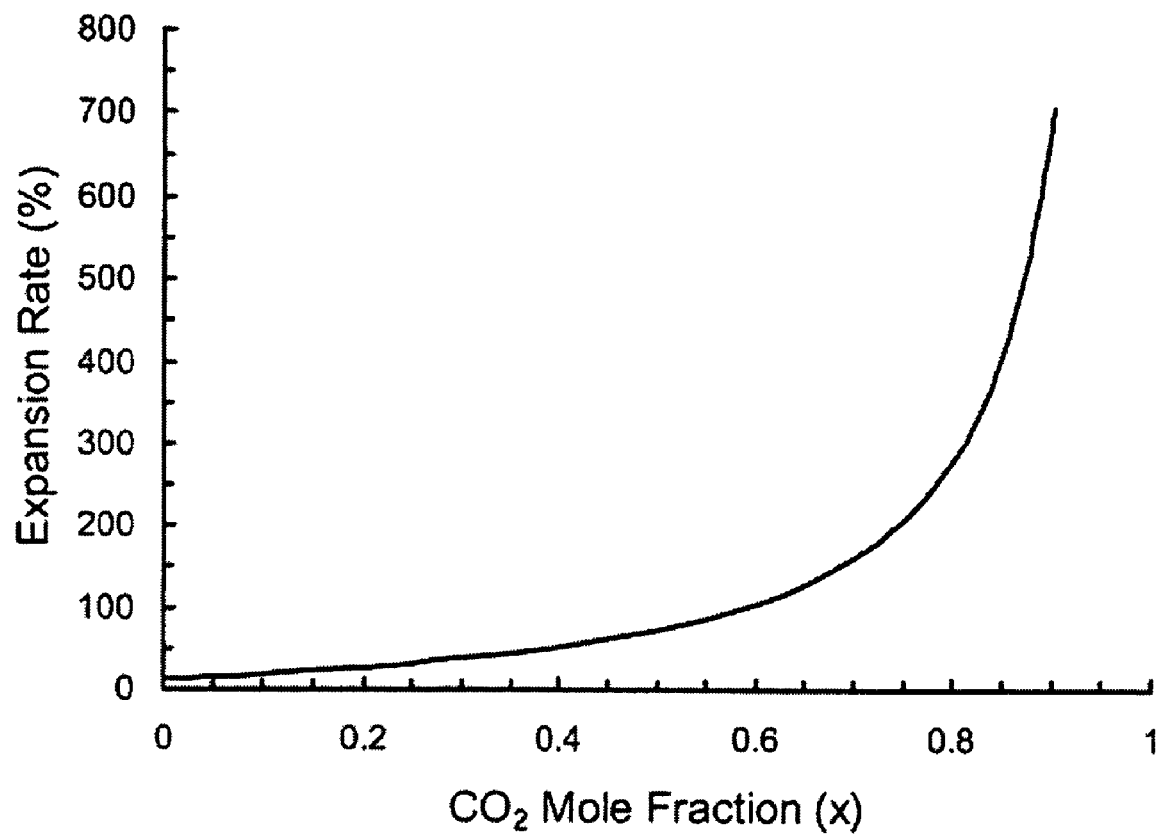
FIG. 29 is a plot depicting volume expansion ratio of acetone as function of carbon dioxide.

The calculated volume expansion rate as a function of the $CO_2$ mole fraction is shown in FIG. 29. The volume of acetone increases slowly with $CO_2$ mole fraction from 0 to 0.8. However, the volume expands significantly at higher $CO_2$ mole fraction. When the mole fraction is greater than 0.85, the acetone is fully expanded. The expansion behavior of acetone results in a decrease in the partial molar volume of the solvent so that the solvent strength is reduced. In order to predict the solubility of PLGA in expanded acetone by $CO_2$, the partial molar volumes of each component $\bar{v}_i$ in the liquid phase are needed. These volumes are obtained by differentiating the PREoS:

$$\bar{v}_i = \frac{RT}{P}\left(Z + (1 - x_i)\left(\frac{\delta Z}{\delta x_i}\right)_{T,P}\right), i = 1, 2 \quad (10)$$

where $Z$ is the compressibility factor. The solubility of a solute in the liquid phase of the expanded solvent, $S_3 (T, P)$, is expressed as:

$$S_3(T, P) = \frac{\bar{v}_2(T, P, x)}{\bar{v}_2(T, 1, 0)} S_3(T, 1) \quad (11)$$

where $S_3 (T,1)$ is the solubility at 1 atm, $\bar{v}_2 (T, P, x)$ is the partial molar volume of solvent at T, P, and x, and $\bar{v}_2 (T,1,0)$ is the partial molar volume of solvent at 1 atm and at the same temperature with no $CO_2$ dissolved.

Figure 30:
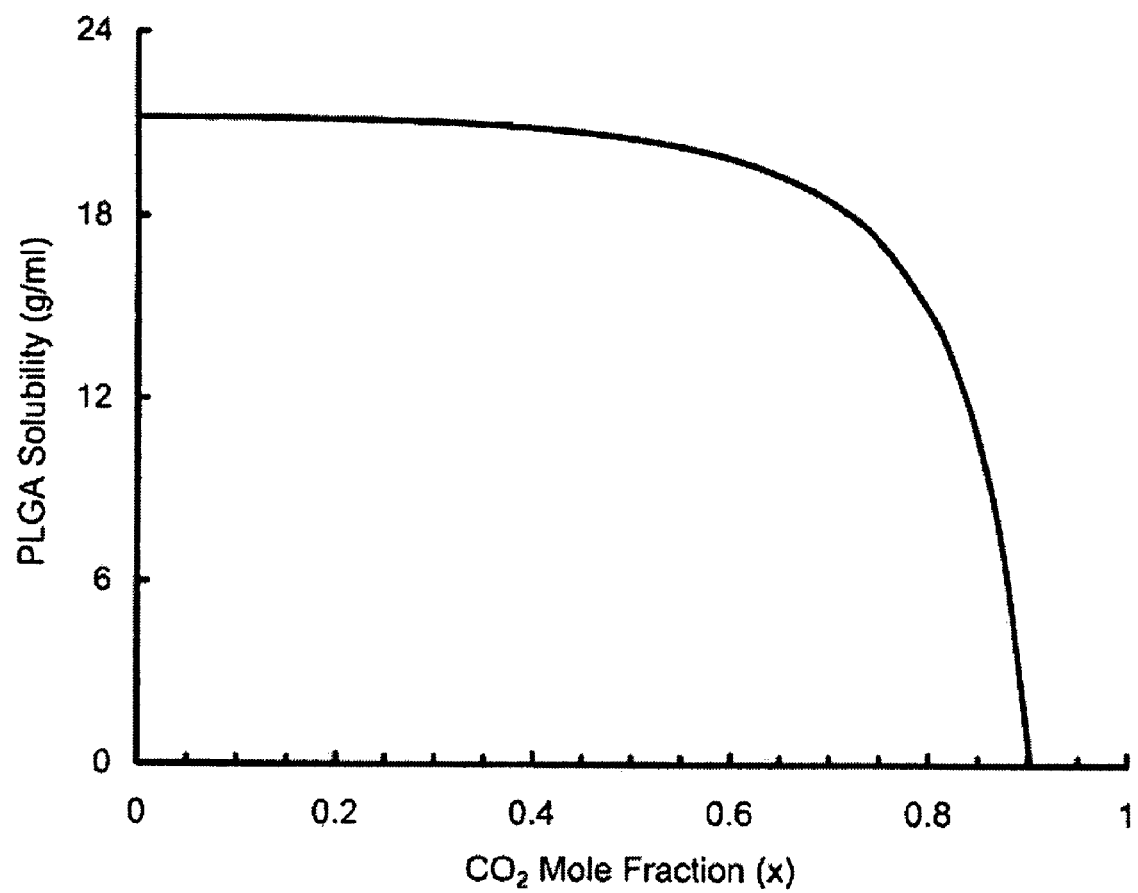
FIG. 30 is a plot depicting solubility of PLGA in expanded acetone as a function of carbon dioxide.

The predicted solubility of PLGA in acetone expanded by $CO_2$ is depicted in FIG. 30, which shows that the solubility of PLGA in the liquid phase drops as the $CO_2$ mole fraction is increased. When the $CO_2$ mole fraction is above 0.7, the solubility decreases considerably. Above 0.85, the solubility of PLGA in acetone is negligible. The $CO_2$ molecules tend to surround the solvent molecules and reduce the partial molar volume of the solvent, causing the decreased solvent strength.

A phase diagram helps to explain the SAS polymer coating process of the present disclosure, although the overall process is complicated by multiple effects, including hydrodynamics, kinetics, thermodynamics, and mass transfer which all need to be considered. Thus, with reference to FIG. 3, a schematic ternary phase diagram for the solvent-antisolvent-polymer is provided. The regions in the diagram represent: ($S_1$)—a single phase region of polymer dissolved in acetone with some $CO_2$ absorbed; ($S_2$)—a single phase region of mostly polymer with some acetone and $CO_2$ absorbed; and ($S_3$)—a two-phase region made up of the polymer-rich phase and the polymer-lean phase. The arcuate line shown in FIG. 3 corresponds to the solubility curve, representing the solubility of PLGA in the mixture of acetone and $CO_2$. The dotted line depicts the effect of the addition of a polymer solution into SC $CO_2$.

When the acetone-polymer solution (suspended with silica particles) is pumped through a nozzle to form small droplets and contacts SC $CO_2$, a mutual diffusion between the SC $CO_2$ and the polymer solution occurs instantaneously. The SC $CO_2$ is dissolved in acetone, leading to swelling of the droplets. With the continuing diffusion of SC $CO_2$ into the polymer solution and acetone into SC $CO_2$, the polymer solution very quickly reaches saturation in the mixture of acetone and $CO_2$ as shown in FIG. 3 (See point D, saturation point). Subsequently, the polymer solution forms two phases, a viscous polymer-rich phase with particles entrapped and a dilute polymer-lean phase (from D to C). Since the solubility of most polymers is very limited, the polymer-lean phase composition consists primarily of acetone and SC $CO_2$. As the mutual diffusion continues, the polymer-rich phase becomes more concentrated and more viscous. Further removal of solvent from the polymer-rich phase induces a phase transition to the glassy region ($S_2$) (from L to L', M to M', and N to N'). Eventually, the polymer vitrifies, forming a polymer film on the surface of particles. A schematic depiction illustrating this aspect of the disclosed SAS process for fine particle encapsulation (as described above) is shown in FIG. 4.

5. Coating of Fine Silica Particles

Figure 31:
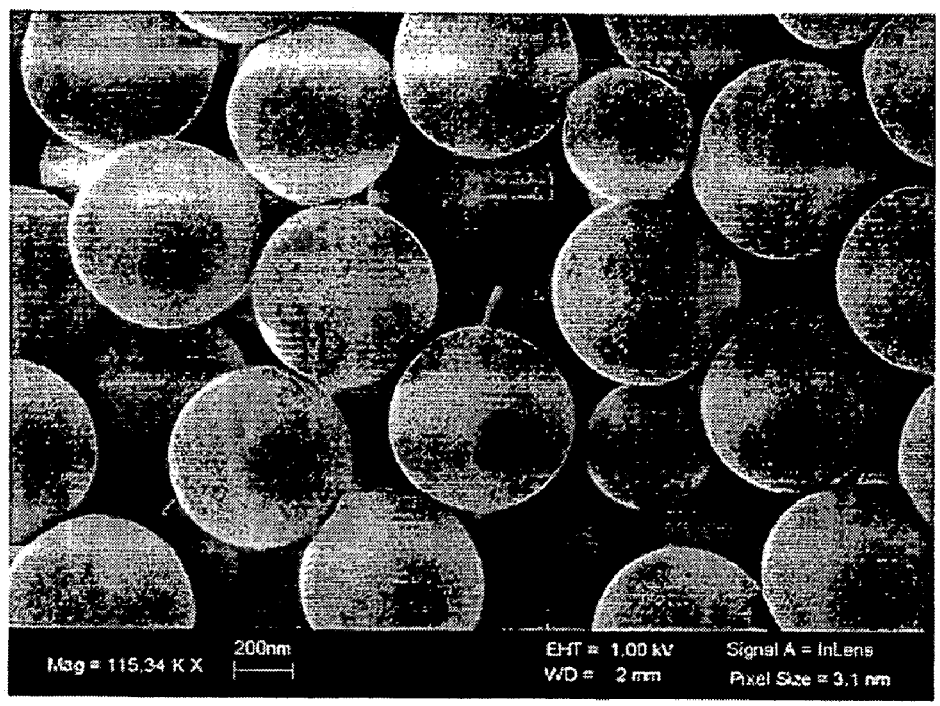
FIG. 31 is an exemplary SEM micrograph showing spherical uncoated silica particles.
Figure 32:
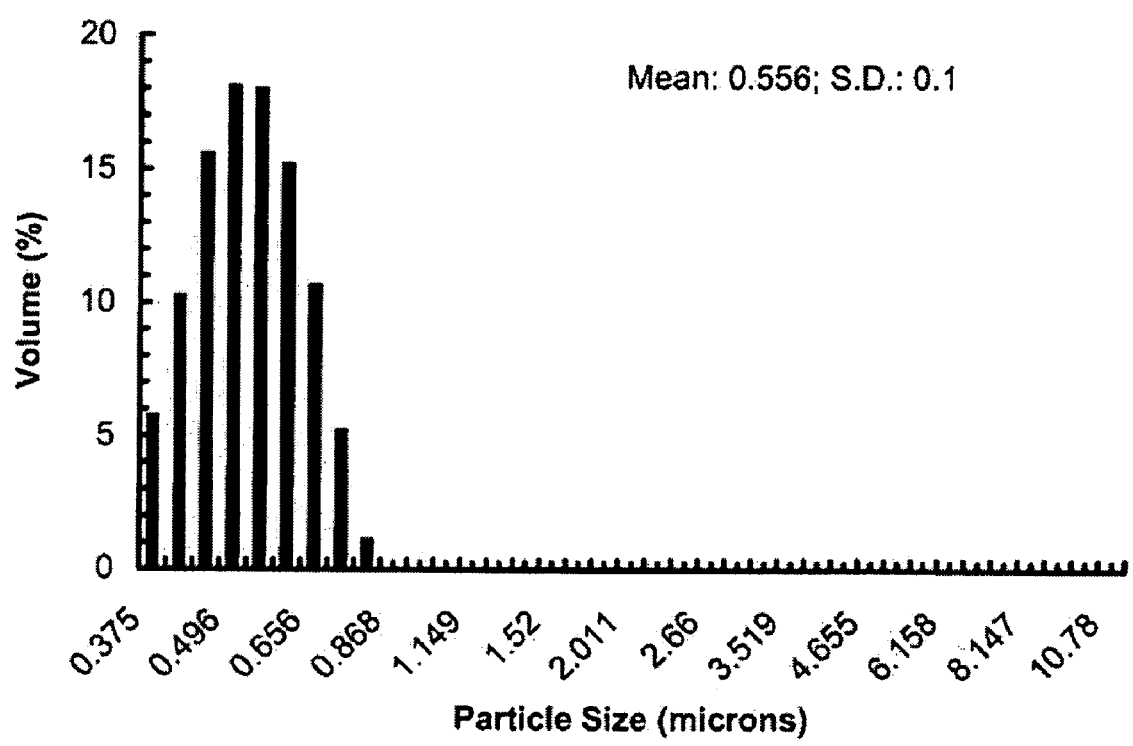
FIG. 32 is a plot depicting particle size and particle size distribution of uncoated silica particles.

High resolution SEM pictures were taken to illustrate morphological changes before and after polymer coating. As seen in FIG. 31, the synthesized silica particles are spherical and smooth on the surface. The particle size and particle size distribution of uncoated silica particles were determined using the LS Particle Size Analyzer. As shown in FIG. 32, the average particle size of uncoated silica particles is 0.556 micron with a standard deviation of 0.1 micron.

Figure 33A:
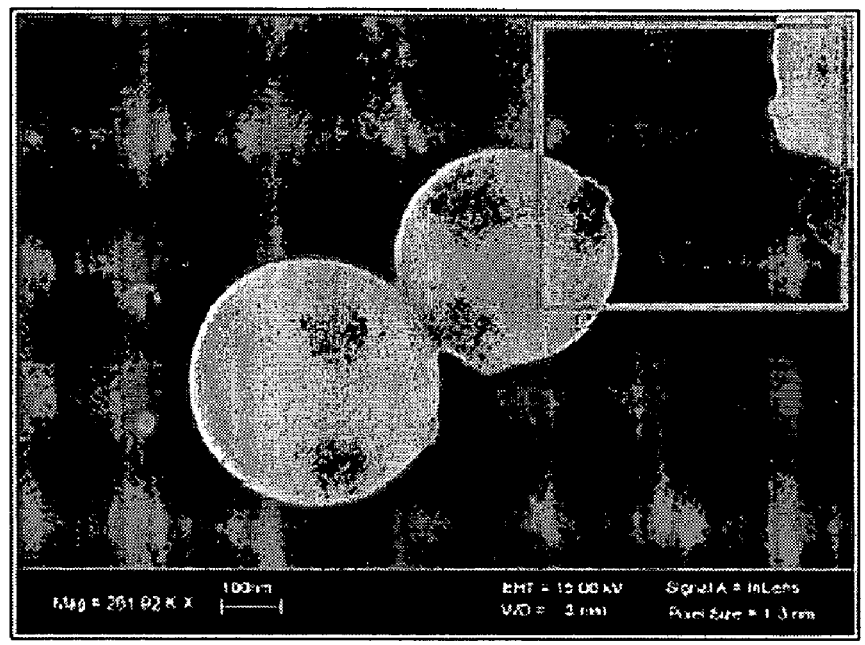
FIGS. 33(a) and 33(b) are exemplary SEM micrographs of: (a) coated silica particles (×261,920) fragmented from an agglomerate after sonication and (b) same coated silica particles after bombardment with an electron beam (×261,920)

FIG. 34a shows the silica particles coated with polymer at a polymer fraction of 25.0% of the total coated particle mass of the total coated particle mass. Compared with FIG. 31, the coated silica particles shown in FIG. 34a exhibit a different morphology and surface feature. The coated particles are heavily agglomerated due to the polymer coating, which acts as a binder. During the precipitation of the polymer, the entanglement of polymer chains between neighboring particles binds them together, forming agglomerates. However, after sonication in alcohol for 3 minutes, the solid polymer bridges between the coated particles appeared to be broken, as shown in the outlined area in FIG. 33a.

Figure 33B:
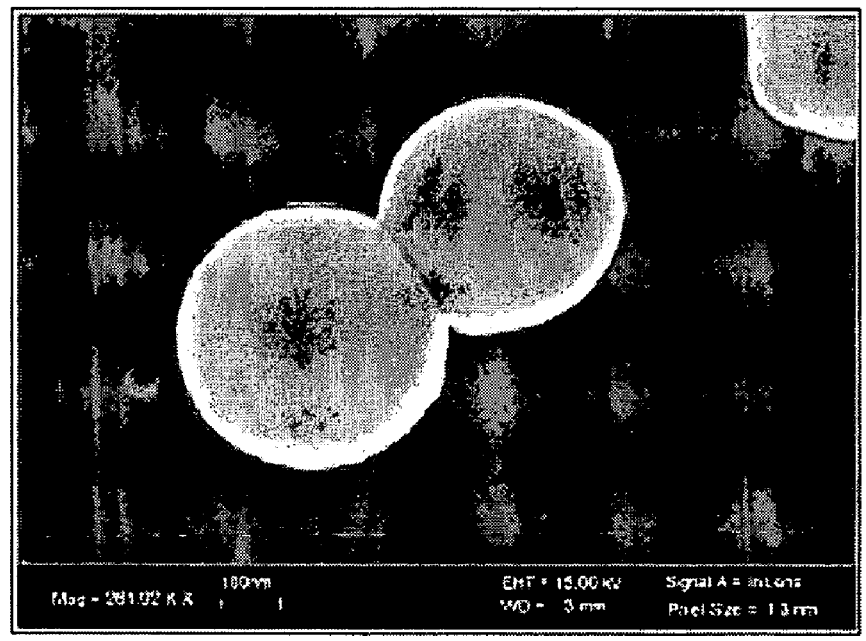

Of note, in capturing SEM images, a high intensity electron beam is used to scan the surface of the particles. Since some of the kinetic energy of the electron beam is absorbed by the particles, the local temperature of the area that is scanned increases. Therefore, after the coated silica particles are exposed to the high intensity electron beam for 15 minutes, the coating polymer becomes soft and spreads over the surface of particles (FIG. 33b) due to the low glass transition temperature of the polymer (40-55° C.).

The quality of the coating and the degree of agglomeration were found to be affected by several operating parameters, including the polymer weight fraction, polymer concentration in acetone, temperature, pressure, flow rate, and the addition of surfactants. Each of these parameters will be described in detail below.

i. Effect of Polymer Weight Fraction

According to the present disclosure, the amount of polymer applied in the coating of particles is important in controlling the coating thickness and agglomeration of the coated particles. In the exemplary processing runs described herein, the disclosed SAS coating process was operated at 33° C. and 8.96 MPa, and the polymer weight fraction was varied from 12.5% to 25.0% (runs 1, 2 and 3). SEM photographs of the coated particles at different polymer weight fractions are shown in FIG. 34. At a high polymer weight fraction of 25.0%, the coated particles were seriously agglomerated (FIG. 34a). When the polymer weight fraction was lowered to 16.7%, the agglomeration became much less pronounced (FIG. 34b). When the polymer weight fraction was lowered even further to 12.5%, the agglomeration between the coated particles appeared to further decrease (FIG. 34c).

Figure 35A:
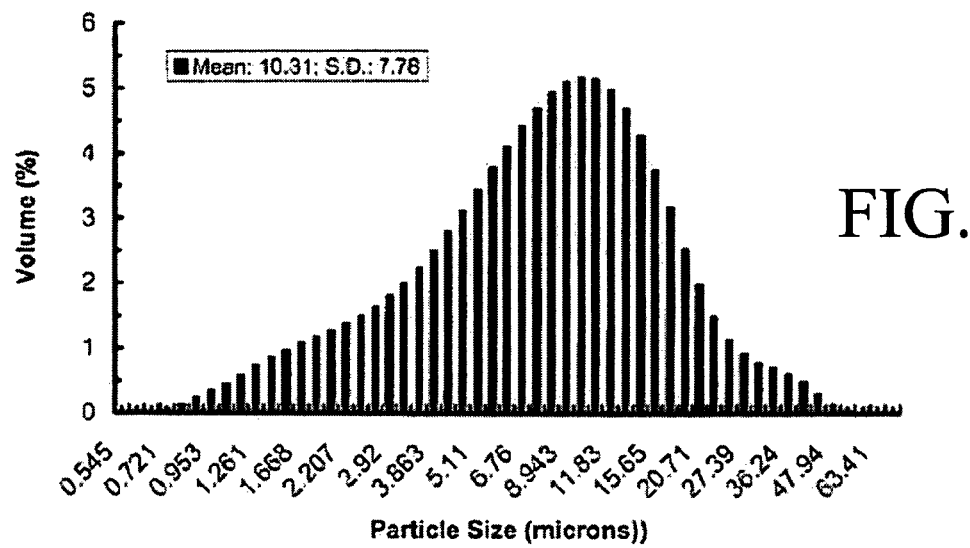
FIGS. 35(a), 35(b) and 35(c) are plots of particle size and particle size distribution.

The coated particles were analyzed in terms of particle size and particle size distribution to determine the degree of agglomeration. In measuring the particle size and particle size distribution, the coated particles were dispersed in ethyl alcohol. The resulting suspension was sonicated for 3 minutes. FIG. 35 shows the results of the particle size and particle size distribution at different polymer weight fractions. The average size of agglomerates of coated particles at the fraction of 25.0% is 10.31 microns with a standard deviation of 7.78 microns as shown in FIG. 35a.

Figure 35B:
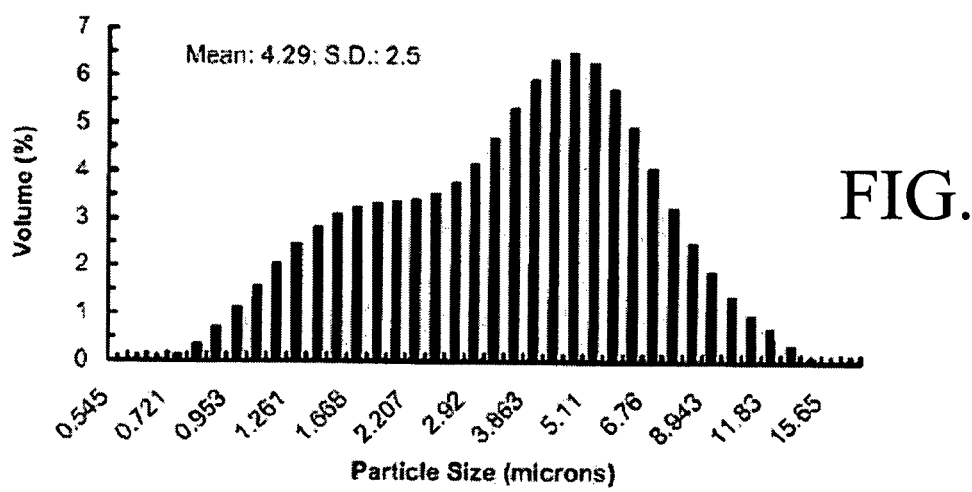
Figure 35C:
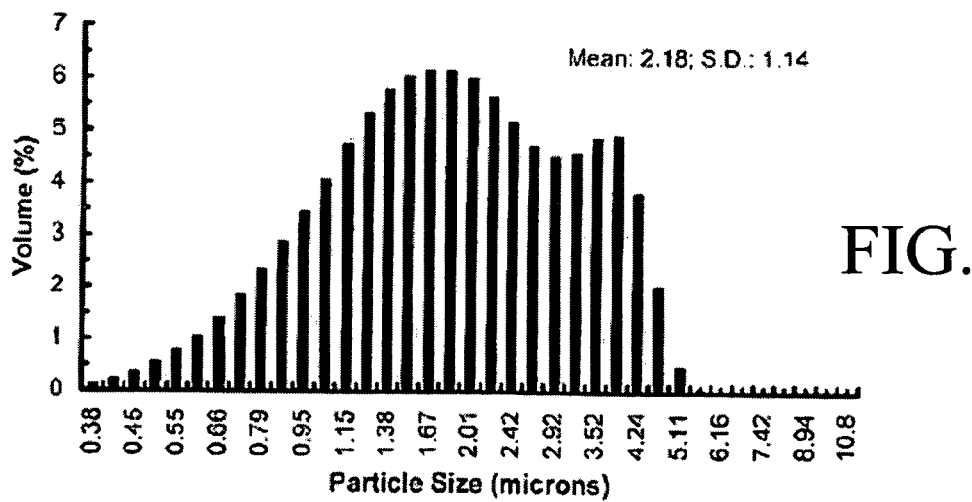

It is readily apparent that agglomeration among the coated particles occurred because the average size of the uncoated particles is 0.556 microns with a narrow size distribution of 0.1 micron. This is consistent with the SEM images depicted in FIG. 34a. The average size of agglomerates of coated particles decreased considerably, namely to 4.29 microns with a distribution of 2.5 microns, when the particles were coated at the polymer weight fraction of 16.7% (FIG. 35b). When the weight fraction was reduced to 12.5%, the average size of agglomerates of coated particles decreased to 2.18 microns with a distribution of 1.14 microns (FIG. 35c). There is a good agreement between the SEM photographs in FIG. 34 and the results of particle size and particle size distribution analysis using the Beckman Coulter LS Particle Size Analyzer in FIG. 35.

ii. Effect of Polymer Concentration

Figure 36A:
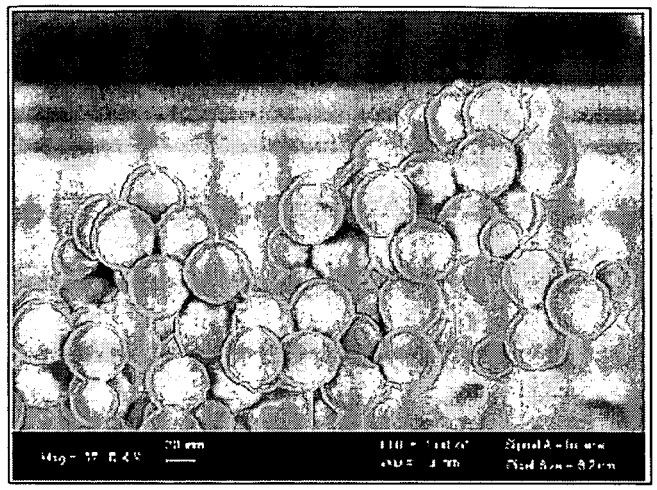
FIGS. 36(a), 36(b) and 36(c) are exemplary SEM micrographs of coated particles at different polymer concentrations: (a) 13.0 mg/ml (Run 8; ×57,100), (b) 10.0 mg/ml (Run 2; ×62,900), and (c) 4.0 mg/ml (Run 7, ×79,230)
Figure 36B:
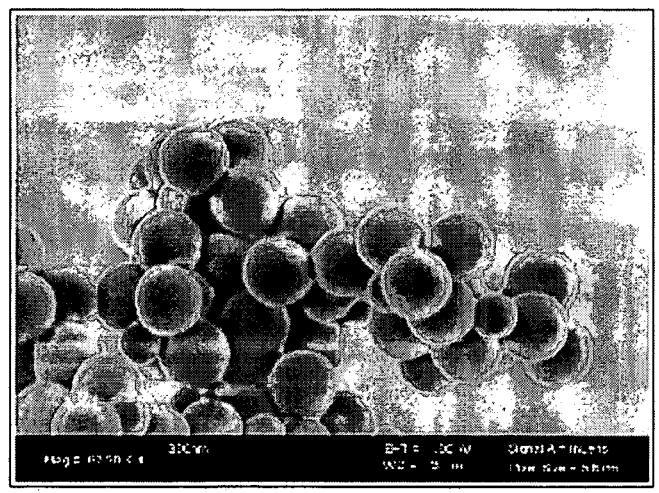
Figure 36C:
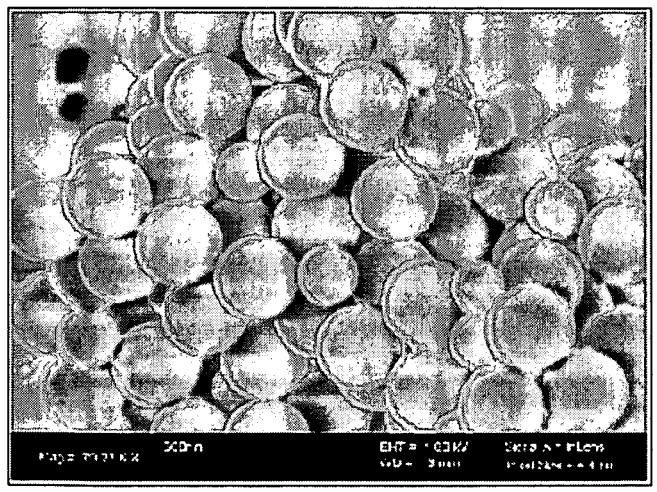

Polymer concentration was found to be important in controlling the agglomeration of coated particles in the disclosed SAS process. The polymer concentration was varied from 4.0 to 13.0 mg/ml while keeping all other operating parameters constant (runs 2, 7 and 8). SEM photographs of coated particles at different concentrations are shown in FIG. 36. At high polymer concentration of 13 mg/ml, the coated particles were heavily agglomerated. In addition, the polymer coating on the surface of particles was found to be unevenly distributed (FIG. 36a). When the polymer concentration decreased to 10.0 mg/ml, the polymer coating on the surface of particles appeared smoother. Nevertheless, agglomeration of coated particles can be seen in FIG. 36b. A further decrease in the polymer concentration to 4.0 mg/ml showed smooth particle coating with minimal agglomeration, as seen in FIG. 36c.

Figures 37A, 37B, 37C:
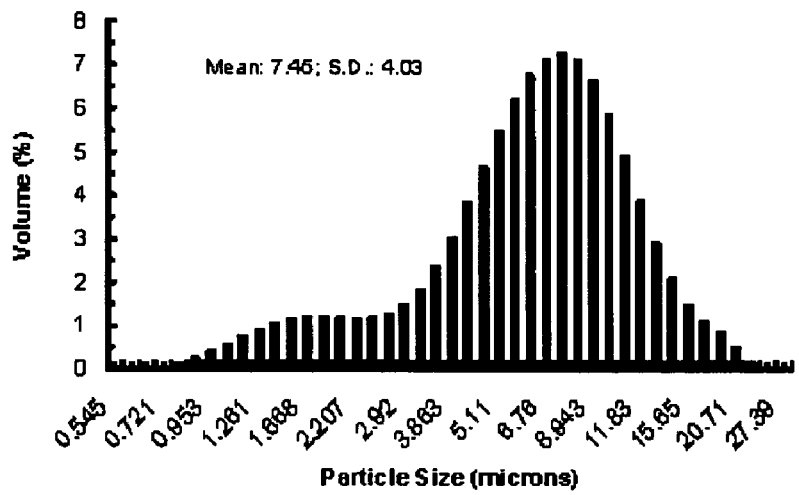
FIGS. 37(a), 37(b) and 37(c) are plots of particle size and particle size distribution for different polymer concentrations: (a) 13.0 mg/ml (Run 8), (b) 10.0 mg/ml (Run 2), and (c) 4.0 mg/ml (Run 7)

The results of the particle size analysis of the coated particles at different polymer concentrations are shown in FIG. 37. Although the polymer weight fraction was kept at 16.7%, a higher polymer concentration results in larger agglomerates. When particles were coated at polymer concentration of 13.0 mg/ml, the average size of agglomerates is 7.45 microns with a distribution of 4.03 microns (FIG. 37a). However, the average size of agglomerates decreased to 4.29 microns when the polymer concentration was reduced to 10.0 mg/ml (FIG. 37b). When polymer concentration was lowered further to 4.0 mg/ml, the average size of agglomerates decreased significantly to 0.613 microns with a distribution of 0.135 microns (FIG. 37c). Indeed, it appears that no agglomeration occurred and that the increase in average particle size is simply due to the polymer coating on the surface of the particles. The coating thickness is estimated to be 28.5 nanometers based on the measurements of uncoated particles and coated particles at a polymer concentration of 4.0 mg/ml.

The thickness of the coating layer on the surface of the particles can also be estimated from the polymer weight fraction. If it is assumed that no agglomeration occurs, that the PLGA only coats the silica particles and the coating is uniform on the surface of a particle with a thickness, t, then, utilizing Equation (1) previously discussed (i.e., $t = R(1 + \rho_H m_C / \rho_C m_H)^{1/3} - R$ where R is the radius of the uncoated particle, $\rho_H$ and $\rho_C$ are the density of the host particles and PLGA, and $m_H$ and $m_C$ are the weight of the host particles and polymer). Knowing the polymer weight fraction and using Equation (1), t is estimated to be 29 nanometers, which is very close to the value obtained from the size measurements of the uncoated particles and coated particles. This calculation strongly supports the conclusion drawn above that no agglomeration among coated particles occurs when using a polymer concentration of 4.0 mg/ml.

iii. Effect of Temperature

Figure 38A:
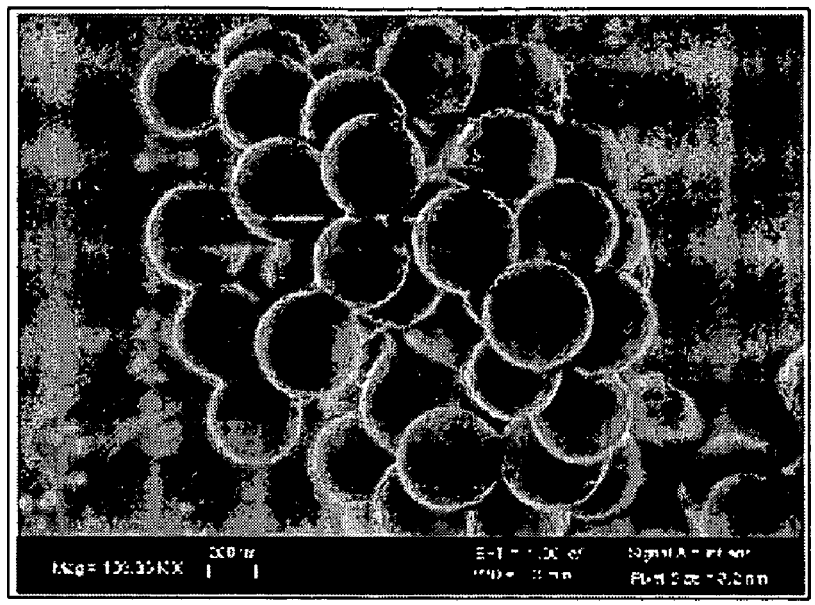
FIGS. 38(a) and 38(b) are SEM micrographs of coated particles at different temperatures: (a) 38° C. (Run 5; ×109, 360), and (b) 42.5° C. (Run 6; ×60,540)
Figure 38B:
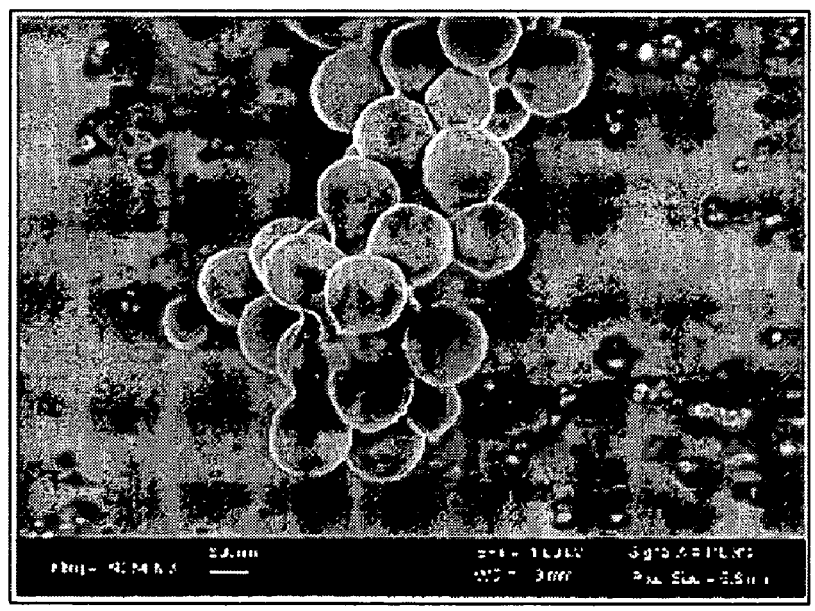
Figure 39A:
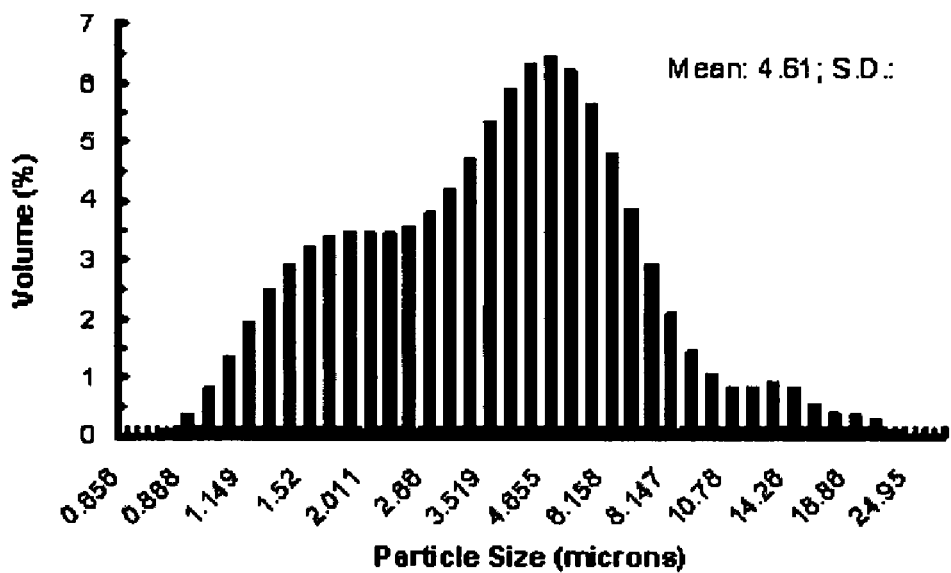
FIGS. 39(a) and 39(b) are plots of particle size and particle size distribution for coated particles at different temperatures: (a) 38° C. (Run 5), and (b) 42.5° C. (Run 6)

In previous studies using the SAS process for particle formation, the operating temperature was found to affect both the particle size and morphology of the final product. Since the SAS processes for particle formation and for particle coating are similar (except that in coating applications the host particles are suspended in the polymer solution before being delivered into SC $CO_2$), it is likely that temperature will have an effect on the coating and agglomeration of the coated particles. To confirm the presence and determine the nature of the temperature effect for the disclosed coating process, experiments were carried out at different temperatures from 33 to 42.5° C., while the other operating parameters were kept constant (runs 2, 5, and 6). FIG. 34b and FIG. 38 show SEM photographs of coated particles processed at different temperatures. Below the glass transition temperature of PLGA ($T_g$=40-55° C.), the coated particles at 33 and 38° C. appear to be very similar. The average size of the agglomerates at 33° C. is 4.29 microns with a distribution of 2.5 microns (FIG. 37b), and at 36° C., the average agglomerate size is 4.61 microns with a distribution of 3.25 microns (FIG. 39a).

Figure 39B:
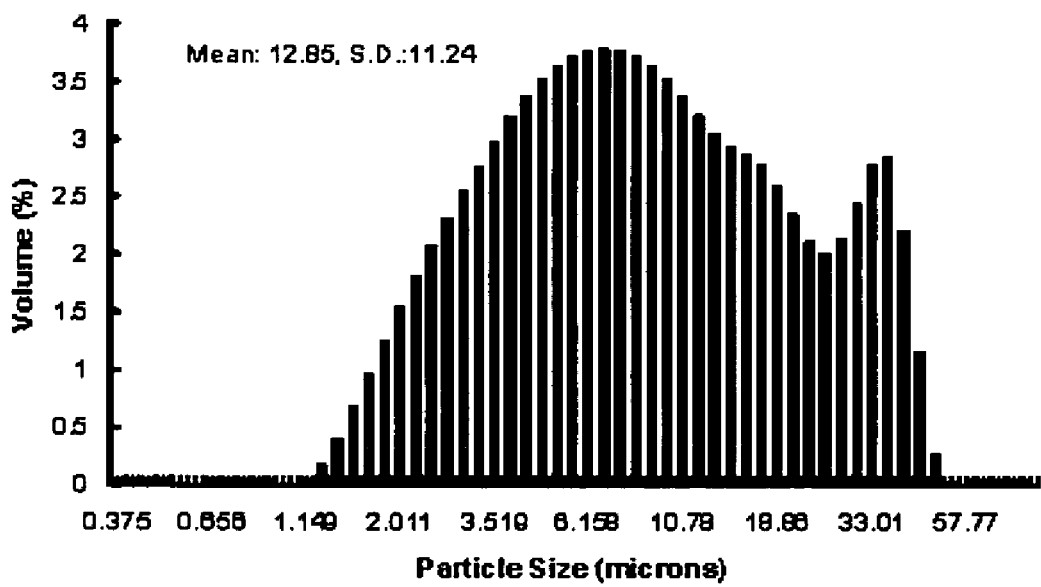

Based on these test results, there is only a very slight increase in agglomerate size with temperature below the glass transition temperature. However, when the operating temperature is increased to 42.5° C., i.e., above the glass transition temperature of PLGA, the coated particles were heavily agglomerated (FIG. 38b) due to sintering. In addition, the polymer coating is very unevenly distributed on the surfaces of the host particles. A particle size measurement of the coated particles at 42.5° C. shows that the average size of the agglomerates increases significantly from about 4.5 to 12.9 microns (FIG. 39b).

iv. Effect of Pressure

The pressure of the system is an important variable in the SAS process of the present disclosure because it affects the density of SC $CO_2$. Thus, the rate of mutual diffusion between SC $CO_2$ and the polymer solution will be influenced. Furthermore, Mawson et al. and Condo et al [24] found that the glass transition temperature of polymers could be depressed by compressed $CO_2$. [See, Mawson et al., *Stabilized Polymer Microparticles by Precipitation with a Compressed Fluid Antisolvent: 1. Poly (Fluoro Acrylates)*, Macromolecules 30 (1997) 71-77; Condo et al., *Glass Transition of Polymers with Compressed Fluid Diluents: Type II and III Behavior*, Macromolecules, 27 (1994) 365-371.]

Figure 40A:
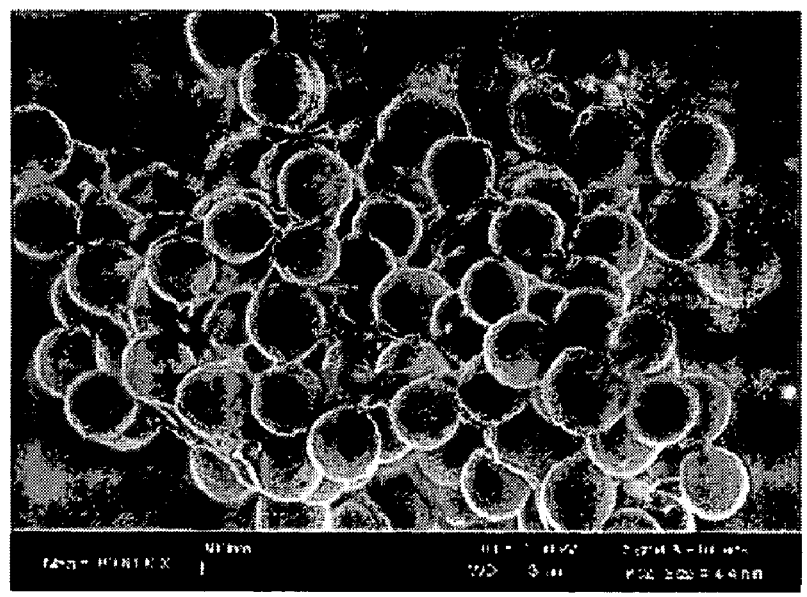
FIG. 40(a) is an exemplary SEM micrograph of agglomerates of coated particles at a pressure of 11.03 MPa (Run 4; ×80,610)
Figure 40B:
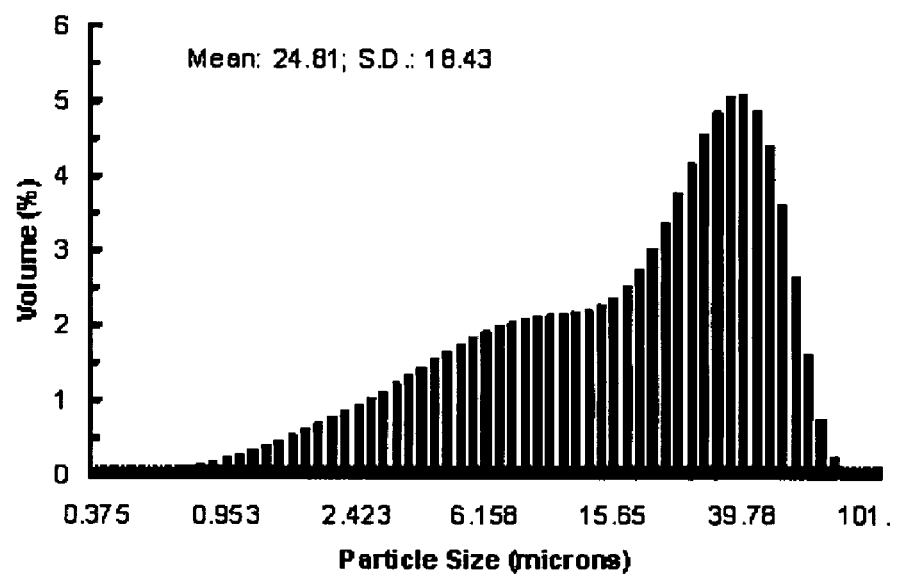
FIG. 40(b) is a plot of particle size and particle size distribution for such agglomerates.

Experimental runs were carried out at two different operating pressures of 8.96 and 11.03 MPa while the temperature was kept constant at 33° C. (runs 1 and 4). FIG. 40a shows a SEM photograph of coated particles processed at an operating pressure of 11.03 MPa. The coated particles were heavily agglomerated compared with the coated particles seen in FIG. 34a which were processed at an operating pressure of 8.96 MPa. In addition, it was found that the polymer coating was unevenly distributed when processed at the higher pressure. The average size of the agglomerates increased to 24.8 microns with a distribution of 18.4 microns as shown in the plot of FIG. 40b. The uneven coating distribution may be due to a depression in $T_g$ of the polymer in pressurized $CO_2$. The agglomeration of coated particles appears to be enhanced by plasticization of coating polymer under high pressure. The degree of plasticization of polymer is proportional to the amount of $CO_2$ absorbed into the polymer matrix, that is, proportional to the operating pressure. This explains why the agglomeration of coated particles at 11.03 MPa is significantly greater than at 8.96 MPa. Also, $T_g$ depression appears to favor a redistribution of polymer coating on the surface of particles, as seen in FIG. 40a.

v. Effect of Flow Rate

In SAS particle formation, the flow rate of the solution has been reported to have an effect on the particle size and morphology of final products. [See, e.g., Randolph et al., *Sub-Micrometer-Sized Biodegradable Particles of Poly (L-Lactic Acid) via the Gas Antisolvent Spray Precipitation Process* Biotechnol. Progress 9 (1993) 429; Chattopadhyay et al., *Supercritical CO2 based Production of Fullerence Nanoparticles*, Ind. Eng. Chem. Res. 39 (2000) 2281-2289; Tu et al., *Micronisation and Microencapsulation of Pharmaceuticals Using a Carbon Dioxide Antisolvent*, Powder Technol.126 (2002) 134-149.]

Figure 41A:
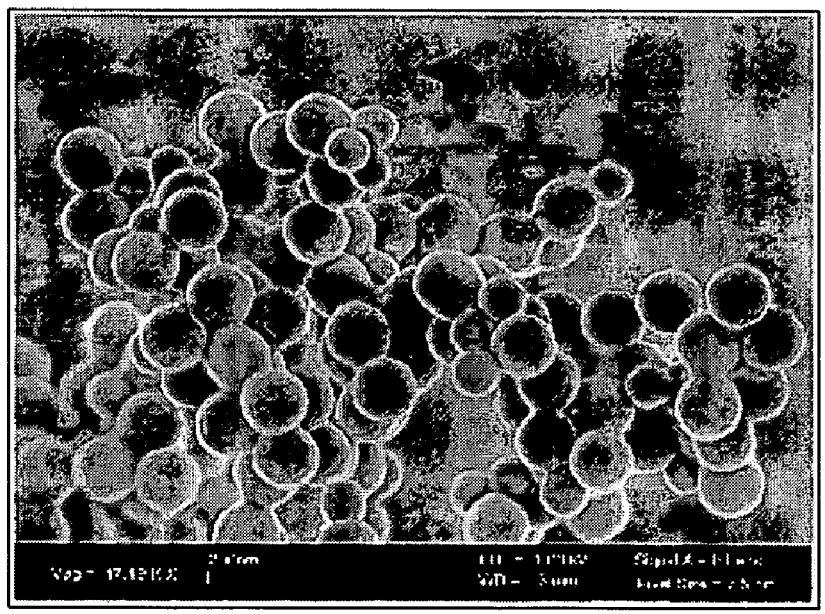
FIGS. 41(a) and 41(b) are exemplary SEM micrographs of coated particles at different flow rates: (a) 1.8 ml/min (Run 9; ×47,190), and 2.8 ml/min (Run 10; ×50,060)
Figure 41B:
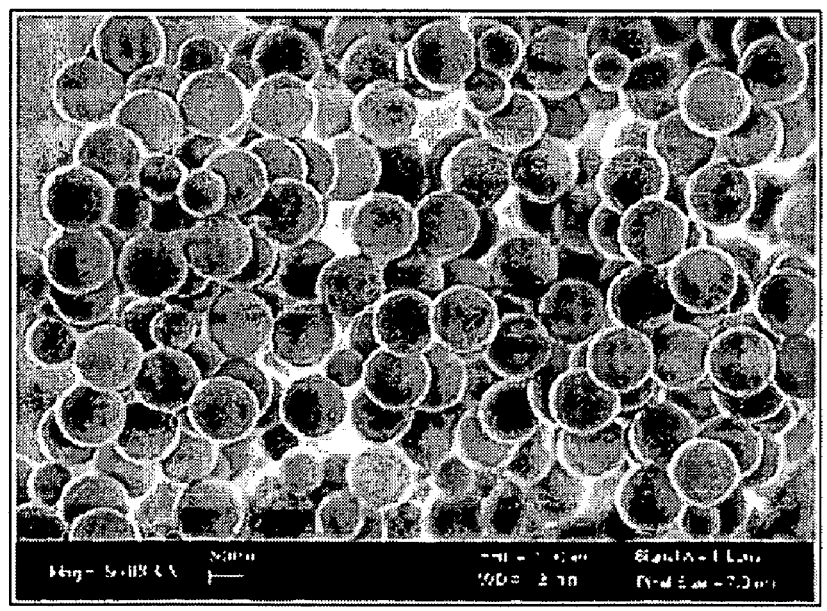
Figure 42A:
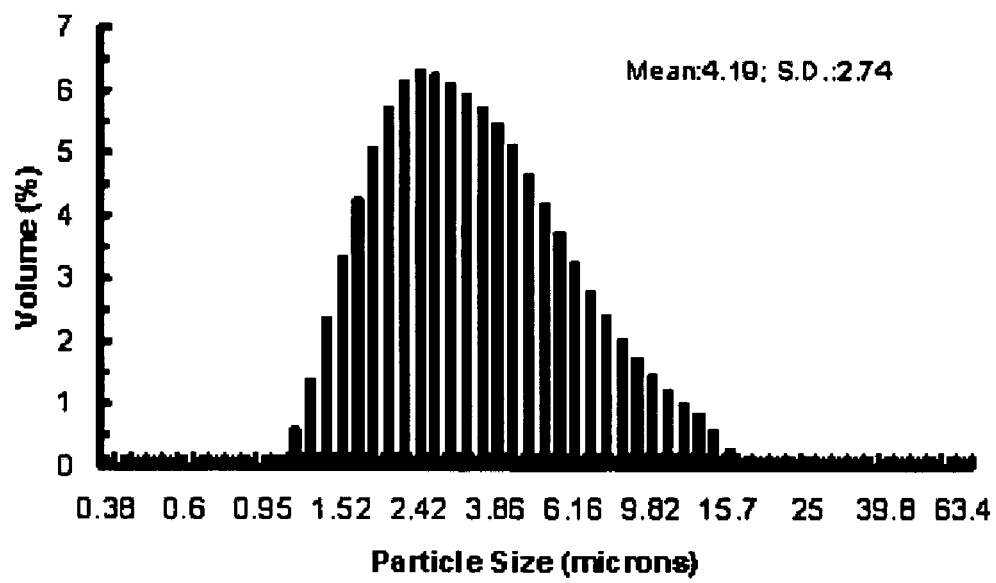
FIGS. 42 are plots of particle size and particle size distribution of coated particles at different flow rates: : (a) 1.8 ml/min (Run 9), and 2.8 ml/min (Run 10)
Figure 42B:
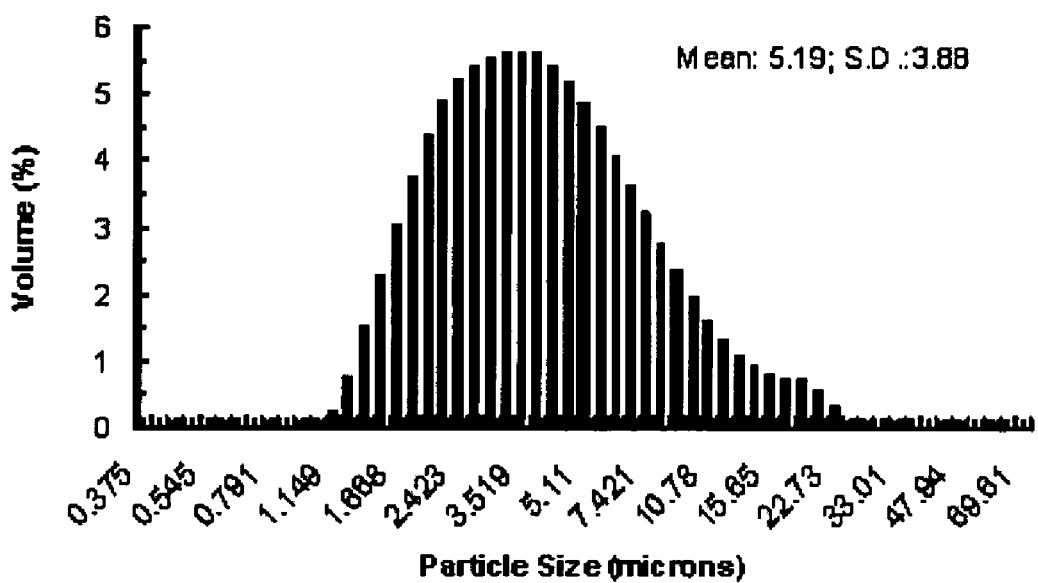

Experimental runs were performed at different flow rates varying from 0.8 to 2.8 ml/min (runs 2, 9, and 10). The SEM photographs of the coated particles are shown in FIGS. 34b and 41. The surface of the coated particles at all three different flow rates is fairly smooth and there does not appear to be any difference in the degree of agglomeration due to changes in flow rate. The particle size measurements are shown in FIGS. 35b and 42. No clearly defined trend can be observed from these measurements, except that the average size of the agglomerates at a flow rate of 2.8 ml/min is slightly increased. Thus, it appears that flow rate plays a less critical role in the coating of particles in the disclosed SAS process compared to other operating parameters, such as polymer concentration, polymer weight fraction, temperature, and pressure. However, the concentration of the organic solvent in the suspension droplets extracted by SC $CO_2$ should be sufficiently low so that the polymer coating on the surface of the silica particles solidifies before contacting other coated particles or the surface of the vessel. Otherwise, agglomeration would take place when the viscous liquid polymer coatings on the surfaces of particles contact each other. Based on the foregoing, the flow rate should be lower than a certain limiting value to prevent agglomeration.

vi. Effect of Surfactants

To evaluate the effect of surfactants in the disclosed SAS coating process, various surfactants that are fully soluble in SC $CO_2$ were tested at the concentration, temperature and pressure of interest. The fluoroalkyl side chains of the perfluoroalkoxy polymer (PFA) and perfluoroacrylate-styrene polymer (PFS) and the polyfluoroether tail of the Krytox 157 FS [E.I. du Pont de Nemours and Company, Wilmington, Del.] are known to be $CO_2$-philic and were expected to interact favorably with the SC $CO_2$. [See, Blasig et al., *Effect of Concentration and Degree of Saturation on RESS of a $CO_2$-soluble Fluoropolymer*, Ind. Eng. Chem. Res., 41 (20), (2002), 4976-4983; Xu et al., *Thickening Carbon Dioxide with the Fluoroacrylate-Styrene Copolymer*, SPE J. 8 (2) (2003), 85-91; Hoefling et al., *Design and Synthesis of Highly $CO_2$-soluble Surfactants and Chelating Agents*, Fluid Phase Equilibria, 83 (1993) 203-212.] According to the present disclosure and with respect to the foregoing polymeric materials, coating of the PLGA surface was believed to be associated with the $CO_2$-phobic backbone of PFA, the backbone and pendant aromatic groups of the PFS, and the carboxylic acid of the Krytox 157 FS coating and/or adhering to the PLGA surface.

In commencing the surfactant-related experimental runs, a pre-determined amount of surfactant was put into the high-pressure chamber. When the desired experimental conditions were reached, the magnetic stirrer was turned on (300-600 rpm) to facilitate dissolution of the surfactant. After about 30 minutes agitation, the surfactant was believed to be completely dissolved in SC $CO_2$. The suspension of particles in polymer solution was then supplied by the HPLC pump through the nozzle into SC $CO_2$ with the surfactant presumed to be dissolved. The subsequent steps of flushing with fresh $CO_2$ and depressurization were conducted in the same manner as described above for the SAS coating experiments without surfactants.

Since the pressure in the disclosed SAS coating process is in the range of 8.96 MPa, which is much lower than the pressures in dispersion polymerization and impregnation work involving SC $CO_2$, a level of 0.1% PFS surfactant in SC $CO_2$ was employed in the initial experimental run. However, the surfactant, which was known to dissolve very slowly in SC $CO_2$ even when agitated, was found not to have been completely dissolved based on the presence of surfactant chunks inside the vessel after disassembly of the high-pressure chamber. In a PCA microparticle formation study done by Mawson et al., the effective surfactant concentrations to stabilize polymer microparticles were in the range of 0.01% to 0.05% depending on the surfactants used when the surfactants were introduced in $CO_2$ phase at the operating conditions of 23° C. and 14.9 MPa. [See, Mawson et al., *Stabilized Polymer Microparticles by Precipitation with a Compressed Fluid Antisolvent. 2. Poly (propylene oxide)- and Poly (butylene oxide)-Based Copolymers*, Langmuir, 13 (6), 1997, 1519-1528.] Therefore, the amount of surfactant was reduced to 0.0185% for subsequent experimental runs.

To facilitate comparison with non-surfactant experimental run #1, the same experimental conditions were used except that a higher pressure of 9.65 MPa (instead of 8.96 MPa) was used in the surfactant study because the surfactants were not completely dissolved in SC $CO_2$ even at the concentration of 0.0185%. When the experiment was completed, surprisingly no free flowing particles or agglomerates were observed inside the chamber. Instead, a film coating occurred on the surface of the chamber, and on the surface of the stirrer as well. The film coating was scraped from the surface and was observed underneath the SEM.

Figure 43A:
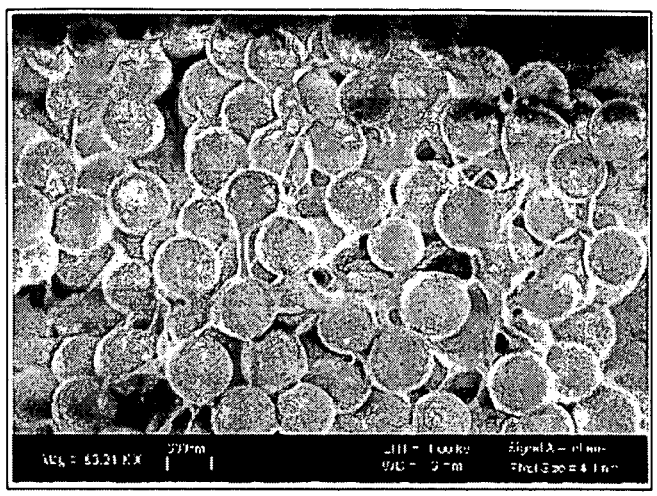
FIGS. 43(a), 43(b) and 43(c) are exemplary SEM micrographs of coated particles using surfactants in which the polymer weight fraction was 25.0%, the polymer concentration was 10 mg/ml, and the flow rate was 0.8 ml/min: (a) PFS, (b) PFA, and (c) Krytox.

FIG. 43a shows the coated particles scraped from the surface of the vessel in the SAS coating experiment with the addition of PFS surfactant. It can be seen that the coated particles are very heavily agglomerated. Furthermore, the coating is found to be very different in nature as compared with the coating shown in FIG. 34a, even though the polymer weight fraction is the same. This might be attributed to the molecular interaction between PLGA and PFS, since they both have —COO— groups. Under supercritical pressure, molecular attraction may cause the backbone of PFS to stick to PLGA while the pendent $CO_2$-philic fluoroalkyl groups extend into the SC $CO_2$ phase. After depressurization, the $CO_2$-philic fluoroalkyl chains may intertwine and collapse, forming a network and binding the coated particles together. In this case, PFS acts more likely as a plasticizer for PLGA instead of a stabilizing agent.

As an alternate explanation for the relatively poor performance of the PFS surfactant, it is noted that the other tested surfactants were $CO_2$ soluble and acetone soluble and appeared to make no significant difference. In contrast, the fluorosurfactant is $CO_2$ soluble and acetone insoluble. It is possible that the addition of acetone to the $CO_2$ caused the fluorosurfactant to precipitate because acetone is an antisolvent for the fluorosurfactant. Therefore, the surfactant could have come out of solution upon introduction of the acetone. Since each of the three fluorosurfactants liquefy in liquid or dense $CO_2$, the PLGA particles could have fallen into the wet film of surfactant which then solidified when the cell was depressurized, causing agglomeration of the PLGA coated silica.

Figure 43B:
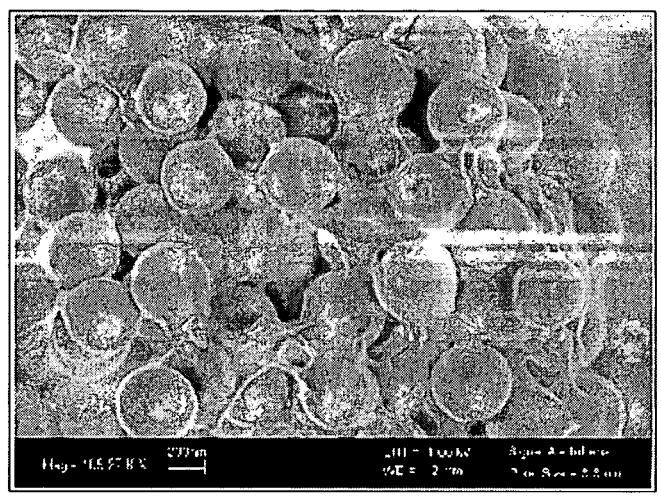
Figure 43C:
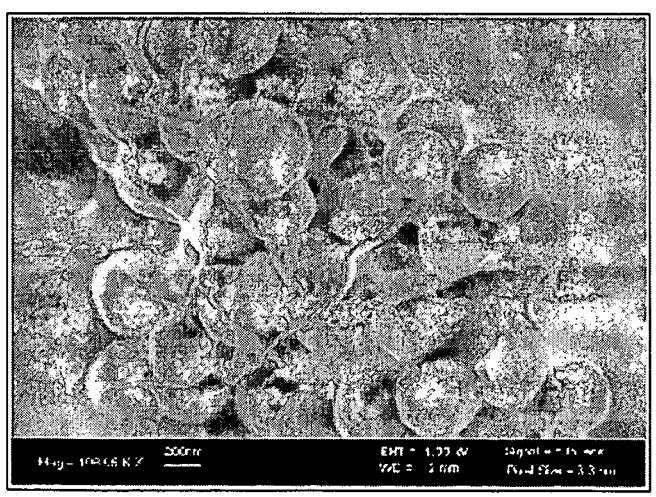

Two other surfactants soluble in SC $CO_2$, namely PFA and Krytox™, were also used following the same experimental procedure as with the PFS surfactant. Again, particle coating on the surface of the vessel and stirrer was found in both experimental runs. SEM photographs of the coated products from these experimental runs are shown in FIGS. 43b and 43c, respectively. Clearly, the coated particles are very heavily agglomerated in both cases due to interactions between the surfactants and the PLGA.

Two other SC $CO_2$ soluble surfactants, poly (dimethylsiloxane) (PDMS) and block co-polymer poly (propylene oxide)-poly (ethylene oxide)-poly (propylene oxide) (PPO-PEO-PPO) [Pluronic 25R2], were also tested. These two surfactants were dissolved in the coating polymer solution and were sprayed into SC $CO_2$ with the solution, since these two surfactants are soluble in acetone. However, the results showed that the coating with these two surfactants as compared to experimental runs without surfactants were similar, no clear effect on the minimization of the agglomeration of coated particles was observed.

Thus, in the foregoing experimental tests, particle coating with polymer using the disclosed SAS process with SC $CO_2$ was systematically studied. Our results show that submicron silica particles were successfully coated or encapsulated by PLGA in the form of loose agglomerates. It was found that the polymer weight fraction and the polymer concentration play a critical role in the agglomeration of the coated particles. A high polymer weight fraction favors agglomeration of the coated particles and an uneven distribution of the polymer coating. A low polymer concentration of 4.0 mg/ml appears to prevent and/or minimize agglomeration among the coated particles. The operating pressure and temperature were also found to influence agglomeration. A higher pressure facilitates the agglomeration of coated particles due to sintering because the glass transition temperature of the polymer, $T_g$, is depressed. The operating temperature appeared to have little effect on the agglomeration of the coated particles when the temperature is below the glass transition temperature; however, when the operating temperature is above $T_g$, the polymer coating on the surface of particle appears to be sintered causing strong agglomeration. The flow rate of the polymer suspension was found to have little effect on agglomeration. The inclusion of a surfactant (PFA, PFS, Krytox, PDMS, and Pluronic 25R2) did not function to suppress agglomeration and, in the case of PFA, PFS, and Krytox surfactants, agglomeration of the coated nanoparticles/ultrafine particles was promoted.

Although the foregoing studies were performed with exemplary host particles (spherical silica particles), coating material (PLGA), solvent (acetone) and supercritical fluid (SC $CO_2$), the system and method of the present disclosure is not limited to the exemplary materials, processing equipment and/or processing parameters disclosed herein. Indeed, the test parameters are merely illustrative of exemplary implementations of the present disclosure, and alternative implementations (in whole or in part) may be undertaken, as will be readily apparent to persons skilled in the art. Moreover, the advantageous coating/encapsulation results achieved through the preferred processing parameters described herein may be achieved in a variety of fields and applications, e.g., pharmaceutical applications, food-related applications, chemical-related applications, pesticide-related applications, polymer-related applications, coating-related applications, catalyst-related applications, conductive ink-related applications and energetic materials applications.

In summary, although the systems and methods of the present disclosure have been described with reference to exemplary embodiments and/or implementations thereof, the present disclosure is not limited to such disclosed exemplary embodiments and/or implementations. Rather, the present disclosure embodies changes, modifications and/or enhancements that would be apparent to persons of ordinary skill in the art, based on the detailed description provided herein. For example, the present disclosure extends to the implementation of the disclosed systems/methods across a wide range of coating applications. The disclosed systems and methods may be advantageously employed to tailor the physical, optical, electronic, chemical and/or biochemical/biomedical properties and/or functionalities of the coated substrates in a variety of ways, as will be apparent to persons skilled in the art. Moreover, it is specifically contemplated that a variety of polymeric systems, solvent systems, supercritical fluid systems and operating conditions may be employed that are consistent with and/or expressly embodied within the teachings set forth herein, without departing from the spirit or scope of the disclosed invention.

What is claimed is:

1. A method for coating ultrafine particles with a polymer, comprising:
   preparing a solution of a polymer in an organic solvent;
   suspending a quantity of insoluble ultrafine particles in said solution to form a suspension; and
   combining a supercritical fluid as an antisolvent with said suspension in a high pressure vessel to cause the polymer to precipitate from said solution and coat the surface of at least a portion of said quantity of suspended ultrafine particles to produce polymer-coated ultrafine particles;
   providing a suspension delivery system and an antisolvent supply system;
   wherein no vibrational force is applied to the high pressure vessel while the antisolvent and suspension are combined in the high pressure vessel;
   wherein said insoluble ultrafine particles are nanoparticles or submicron particles having a particle size of about 16 nm to about 500 nm;
   wherein the polymer concentration of said polymer with respect to said solvent in said solution is less than about 4.0 mg/ml so as to minimize agglomeration of said polymer-coated ultrafine particles;
   wherein the insoluble ultrafine particles are substantially insoluble in the organic solvent;
   wherein the polymer-coated ultrafine particles are in the form of loose agglomerates or individual particles;
   wherein the thickness of the polymer coating on the surface of the polymer-coated ultrafine particles is less than about 75 nm; and
   wherein the antisolvent is combined with the suspension by:
   (i) supplying the antisolvent to the high pressure vessel using the antisolvent supply system; and
   (ii) delivering the suspension into the antisolvent using the suspension delivery system.

2. The method of claim 1, wherein said insoluble ultrafine particles comprise an active pharmaceutical compound and said supercritical fluid is carbon dioxide.

3. The method of claim 1, wherein said polymer content of said polymer-coated ultrafine particles is up to about 25 weight percent based on the total weight of the polymer-coated ultrafine particles.

4. The method of claim 1, wherein said polymer is selected from the group consisting of:
   an acrylic polymer, a polylactic acid polymer, a polylactic acid-glycolic acid polymer, and combinations thereof.

5. The method of claim 1, wherein said ultrafine particles include at least one drug, gene or bioactive agent, and wherein the polymer-coated ultrafine particles function to provide controlled release of said at least one drug, gene or bioactive agent.

6. The method of claim 1, further comprising:
   flushing the polymer-coated ultrafine particles to remove any residual organic solvent therefrom.

7. The method of claim 6, wherein said supercritical fluid is supercritical carbon dioxide and wherein said flushing involves contacting said polymer-coated ultrafine particles with substantially pure carbon dioxide.

8. The method of claim 1, wherein the suspension delivery system includes a capillary tube or nozzle.

9. The method of claim 8, wherein the suspension is delivered into the antisolvent by spraying the suspension though the capillary tube or nozzle into the high pressure vessel.

10. The method of claim 1, wherein said method is effected at a pressure selected to minimize agglomeration of said polymer-coated ultrafine particles.

11. The method of claim 10, wherein said selected pressure does not function to depress the glass transition temperature of said polymer by compressing the supercritical fluid.

12. The method of claim 1, wherein said method is effected at a temperature selected to minimize agglomeration of said polymer-coated ultrafine particles.

13. The method of claim 12, wherein said selected temperature is less than the glass transition temperature of the polymer.

14. The method of claim 1, wherein said antisolvent is supercritical carbon dioxide.

15. The method of claim 1, wherein said antisolvent is supercritical ammonia.

16. The method of claim 1, wherein said antisolvent is a composite supercritical fluid.

17. The method of claim 1, wherein said organic solvent is acetone.

18. The method of claim 1, wherein the antisolvent is combined with said suspension by:
   (i) delivering the suspension into the antisolvent until saturation of said polymer in said suspension is reached, and
   (ii) delivering the suspension into the antisolvent until super-saturation of said polymer in said suspension is reached or a phase transition via nucleation and precipitation of said polymer takes place on a surface of said ultrafine particles to form a polymer coating thereon.

19. The method of claim 1, wherein said ultrafine particles include at least one active pharmaceutical compound and at least one diluent or filler.

20. The method of claim 19, wherein said diluent or filler comprises from 1 to 50 weight percent of said ultrafine particles.

21. The method of claim 19, wherein said diluent or filler is selected from the group consisting of lactose, dextrose, cellulose and combinations thereof 22. The method of claim 1, further comprising applying a force to said solution after the insoluble ultrafine particles are suspended therein and before the suspension is delivered into the high pressure vessel so as to break up agglomerates of the insoluble ultrafine particles formed within said suspension.

23. The method of claim 22, wherein said force is applied by a sonicator or ultrasonicator.

24. The method of claim 1, wherein said polymer-coated ultrafine particles have application in at least one of the following applications: a pharmaceutical application, a food application, a chemical application, a pesticide application, a polymer application, coating application, a catalyst application, a conductive ink application and an energetic materials application.

* * * * *